US010759794B2

(12) United States Patent
Delbeck et al.

(10) Patent No.: US 10,759,794 B2
(45) Date of Patent: Sep. 1, 2020

(54) 2-PHENYL-3-(PIPERAZINOMETHYL) IMIDAZO[1,2-A]PYRIDINE DERIVATIVES AS BLOCKERS OF TASK-1 AND TASK-2 CHANNELS, FOR THE TREATMENT OF SLEEP-RELATED BREATHING DISORDERS

(71) Applicant: BAYER PHARMA AKTIENGESELLSCHAFT, Berlin (DE)

(72) Inventors: Martina Delbeck, Heiligenhaus (DE); Michael Hahn, Langenfeld (DE); Thomas Müller, Langenfeld (DE); Heinrich Meier, Wuppertal (DE); Klemens Lustig, Wuppertal (DE); Johanna Mosig, Dortmund (DE); Luisella Toschi, Berlin (DE); Udo Albus, Florstadt (DE); Doris Gehring, Kelkheim (DE); Björn Rosenstein, Bad Soden-Salmünster (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 15/756,867

(22) PCT Filed: Dec. 7, 2016

(86) PCT No.: PCT/EP2016/079973
§ 371 (c)(1),
(2) Date: Mar. 1, 2018

(87) PCT Pub. No.: WO2017/097792
PCT Pub. Date: Jun. 15, 2017

(65) Prior Publication Data
US 2019/0062326 A1 Feb. 28, 2019

(30) Foreign Application Priority Data

Dec. 10, 2015 (EP) .................................... 15199270
Nov. 2, 2016 (EP) .................................... 16196836

(51) Int. Cl.
*C07D 471/04* (2006.01)
*A61K 31/496* (2006.01)
*A61K 45/06* (2006.01)
*A61P 11/16* (2006.01)

(52) U.S. Cl.
CPC .......... *C07D 471/04* (2013.01); *A61K 31/496* (2013.01); *A61K 45/06* (2013.01); *A61P 11/16* (2018.01)

(58) Field of Classification Search
CPC ..... C07D 471/04; A61P 11/16; A61K 31/496; A61K 45/06
USPC .................................................. 514/263.04
See application file for complete search history.

(56) References Cited

U.S. PATENT DOCUMENTS

| 6,833,364 | B1 | 12/2004 | Straub et al. |
|---|---|---|---|
| 6,864,287 | B1 | 3/2005 | Alonso-Alija et al. |
| 9,127,001 | B2 | 9/2015 | Bialy et al. |
| 9,284,333 | B2 | 3/2016 | Bialy et al. |
| 10,414,765 | B2 | 9/2019 | Delbeck |
| 2002/0022624 | A1 | 2/2002 | Dinnel et al. |
| 2002/0173514 | A1 | 11/2002 | Stasch et al. |
| 2004/0082798 | A1 | 4/2004 | Alonso-Alija et al. |
| 2004/0176446 | A1 | 9/2004 | Alonso-Alija et al. |
| 2004/0224945 | A1 | 11/2004 | Straub et al. |
| 2005/0239823 | A1 | 10/2005 | Oberboersch et al. |
| 2006/0094769 | A1 | 5/2006 | Alonso-Alija et al. |
| 2006/0052397 | A1 | 9/2006 | Alonso-Alija et al. |
| 2008/0058314 | A1 | 3/2008 | Alonso-Alija et al. |
| 2012/0022084 | A1 | 1/2012 | Follmann et al. |
| 2013/0267548 | A1 | 10/2013 | Follmann et al. |
| 2014/0148433 | A1 | 5/2014 | Follmann et al. |
| 2014/0350020 | A1 | 11/2014 | Follmann et al. |
| 2015/0018342 | A1 | 1/2015 | Bialy et al. |
| 2016/0120863 | A1* | 5/2016 | Cowley .............. A61K 31/4985 514/233.2 |
| 2018/0370965 | A1 | 12/2018 | Delbeck et al. |
| 2019/0062326 | A1 | 2/2019 | Delbeck |
| 2020/0085734 | A1 | 3/2020 | Anlahr |
| 2020/0093737 | A1 | 3/2020 | Anlahr |

FOREIGN PATENT DOCUMENTS

| EP | 1974729 A1 | 1/2008 |
|---|---|---|
| EP | 2671582 A1 | 12/2013 |
| WO | WO200006568 A1 | 2/2000 |
| WO | WO200006569 A1 | 2/2000 |

(Continued)

OTHER PUBLICATIONS

Schafer et al. Drug Discovery Today, 2008, 13 (21/22), 913-916.*
Horig et al. Journal of Translational Medicine 2004, 2(44), p. 1-8.*
Bayliss et al., (2015). "The role of pH-sensitive TASK channels in central respiratory chemoreception," *Pflugers Arch.* 467, 467:917-929.
Berg et al., (Jul. 28, 2004). "Motoneurons Express Heteromeric TWIK-Related Acid-Sensitive $K^+$ (TASK) Channels Containing TASK-1 (KCNK3) and TASK-3 (KCNK9) Subunits," *The Journal of Neuroscience* 24(30):6693-6702.
Berry et al., (Mar. 12, 1997). "Upper Airway Anesthesia Reduces Phasic Genioglossus Activity During Sleep Apnea," *Am J Respir Crit Care Med* 156:127-132.

(Continued)

*Primary Examiner* — Yong L Chu
(74) *Attorney, Agent, or Firm* — Morrison & Foerster LLP

(57) ABSTRACT

The present application relates to novel 2-phenyl-3-(piperazinomethyl)imidazo[1,2-a]pyridine derivatives, to processes for their preparation, to their use alone or in combinations for the treatment and/or prevention of diseases, and to their use for preparing medicaments for the treatment and/or prevention of diseases, in particular for treatment and/or prevention of respiratory disorders including, sleep-related respiratory disorders such as obstructive sleep apnoeas and central sleep apnoeas and snoring.

31 Claims, No Drawings

(56) References Cited

FOREIGN PATENT DOCUMENTS

| | | |
|---|---|---|
| WO | WO200119355 A2 | 3/2001 |
| WO | WO200119776 A2 | 3/2001 |
| WO | WO200119778 A1 | 3/2001 |
| WO | WO200119780 A2 | 3/2001 |
| WO | WO2002002557 A2 | 1/2002 |
| WO | WO200242301 A1 | 5/2002 |
| WO | WO2002066478 A1 | 8/2002 |
| WO | WO200270462 A1 | 9/2002 |
| WO | WO200270510 A2 | 9/2002 |
| WO | WO200395451 A1 | 11/2003 |
| WO | WO200435578 A1 | 4/2004 |
| WO | WO2009143156 A2 | 11/2009 |
| WO | WO2011113606 A1 | 9/2011 |
| WO | WO2011115804 A1 | 9/2011 |
| WO | WO2011147809 A1 | 12/2011 |
| WO | WO2012004258 A1 | 1/2012 |
| WO | WO2012028647 A1 | 3/2012 |
| WO | WO2012059549 A1 | 5/2012 |
| WO | WO2012130322 A1 | 10/2012 |
| WO | WO2012143796 A2 | 10/2012 |
| WO | WO2013037736 A1 | 3/2013 |
| WO | WO2013037914 A1 | 3/2013 |
| WO | WO-2014187922 A1 * | 11/2014 ......... A61K 31/4985 |
| WO | WO2014187922 A1 | 11/2014 |
| WO | WO2015144605 A1 | 10/2015 |
| WO | WO2016084866 A1 | 6/2016 |
| WO | WO2016085783 A1 | 6/2016 |
| WO | WO2016085784 A1 | 6/2016 |
| WO | WO2016088813 A1 | 6/2016 |
| WO | WO2017050732 A1 | 3/2017 |
| WO | WO2017097671 A1 | 6/2017 |
| WO | WO2017097792 A1 | 6/2017 |
| WO | WO2018015196 A1 | 1/2018 |
| WO | WO2018114501 A1 | 6/2018 |
| WO | WO2018114503 A1 | 6/2018 |
| WO | WO2018227427 A1 | 12/2018 |
| WO | WO2018228907 A1 | 12/2018 |

OTHER PUBLICATIONS

Bittner et al., (2009). "TASK1 modulates inflammation and neurodegeneration in autoimmune inflammation of the central nervous system," *Brain* 132:2501-2516.

Brouillette et al. (1979). "A neuromuscular mechanism maintaining extrathoracic airway patency," *American Physiological Society* 49:772-779.

Czirják et al. (2000). "TASK (TWIK-Related Acid-Sensitive K$^+$ Channel) is Expressed in Glomerulosa Cells of Rat Adrenal Cortex and Inhibited by Angiotensin II," *Molecular Endocrinology* 14(6):863-874.

Decher et al. (2001). "Characterization of TASK-4, a novel member of the pH-sensitive, two-pore domain potassium channel family," *FEBS Letters* 492:84-89.

Decher et al. (2011). "Knock-Out of the Potassium Channel TASK-1 Leads to a Prolonged QT Interval and a Disturbed QRS Complex," *Cell Physiol Biochem* 28:77-86.

Hollandt et al., "Upper Airway Resistance Syndrome (UARS)—Obstructive Snoring," *HNO* 48:628-634.

International Search Report & Written Opinion dated Jan. 26, 2017, for PCT/EP2016/079544, filed Dec. 2, 2016, 13 pages (German Language).

International Search Report & Written Opinion dated Feb. 20, 2017, for PCT/EP2016/079973, filed Dec. 7, 2016, 11 pages (German Language).

Kim et al., (1999). "TBAK-1 and TASK-1, two-pore K$^+$ channel subunits: kinetic properties and expression in rat heart," *American Physiological Society* H1669-H1678.

Kim et al., (2004). "Altered expression of KCNK9 in colorectal cancers," *APMIS* 112:588-594.

Kiper et al., (2015) "Kv1.5 blockers preferentially inhibit TASK-1 channels: TASK-1 as a target against atrial fibrillation and obstructive sleep apnea?" *Pfluger Arch—Eur J Physiol* 467:1081-1090.

Limberg et al., (Oct. 28, 2011). "TASK-1 Channels May Modulate Action Potential Duration of Human Atrial Cardiomyocytes," *Cell Physiol Biochem* 25:613-624.

Liu et al., (2005). "Protective effects of TASK-3 (KCNK9) and related 2P K channels during cellular stress," *Brain Research* 1031:164-173.

Meuth et al., (May 23, 2008). "TWIK-related Acid-sensitive K$^+$ Channel 1 (TASK1) and TASK3 Critically Influence T Lymphocyte Effector Functions," *The Journal of Biological Chemistry* 283(21):14559-14570.

Mu et al., (Mar. 2003). "Genomic amplification and oncogenic properties of the KCNK9 potassium channel gene," *Cancer Cell* 3:297-302.

Pocsai et al., (2006). "Melanoma cells exhibit strong intracellular TASK-3-specific immunopositivity in both tissue sections and cell culture," *Cell Mol Life Sci* 63:2364-2376.

Rinné et al., (2015). "TASK-1 and TASK-3 may form heterodimers in human atrial cardiomyocytes," *Journal of Molecular and Cellular Cardiology* 81:71-80.

Stühmer (1992). "Electrophysiological Recording from Xenopus Oocytes," *Methods in Enzymology* 207: 319-339.

Tang et al. (2009). "Endothelin-1 Inhibits Background Two-Pore Domain Channel TASK-1 in Primary Human Pulmonary Artery Smooth Muscle Cells," *Am J Respir Cell Mol Biol* 41:476-483.

Trapp et al. (Aug. 27, 2008). "A Role for TASK-1 (KCNK3) Channels in the Chemosensory Control of Breathing," *The Journal of Neuroscience* 28(35):8844-8850.

Verse et al. (1999). "EMG Activity of the Genioglossus Muscle as One Parameter for Diagnosing for Obstructive Sleep Apnea," *Somnologie* 3:14-20 (Summary in English).

Vrints et al. (2013). "Cardiovascular Mechanisms and Consequences of Obstructive Sleep Aponea," *Acta Clinica Belgica* 68(3):169-178.

Whiteaker et al. (2001). "Validation of FLIPR Membrane Potential Dye for High Throughput Screening of Potassium Channel Modulators," *Journal of Biomolecular Screening* 6(5): 305-312.

Wirth et al. (2013). "Sensitization of Upper Airway Mechanoreceptors as a New Pharmacologic Principle to Treat Obstructive Sleep Apnea: Investigations with AVE0118 in Anesthetized Pigs," *SLEEP* 36(5): 699-708.

"FLIPR Membrane Potential Assay Kits," located at https://www.moleculardevices.com/products/assay-kits/ion-channel/flipr-membrane-potential, last visited on Dec. 6, 2018, three pages.

Artursson, P. et al. (Mar. 1991). "Correlation Between Oral Drug Absorption in Humans and Apparent Drug Permeability Coefficients in Human Intestinal Epithelial (CACO-2) Cells," *Biochemical and Biophysical Research Communications* 175(3): 880-885.

Comer, J. et al. (2001). "Lipophilicity Profiles: Theory and Measurement" in Pharmacokinetic Optimization in Drug Research Biological, Physicochemical, and Computational Strategies, Testa, B. et al. eds., Verlag Helvetica Chimica Acta: Zürich, Switzerland, pp. 275-304.

Ertl, P. et al. (2000). "Fast Calculation of Molecular Polar Surface Area as a Sum of Fragment-Based Contributions and Its Application to the Prediction of Drug Transport Properties," *J. Med. Chem.* 43(20):3714-3717.

International Preliminary Report on Patentability dated Jun. 12, 2018, for PCT Application No. PCT/EP2016/079973, filed on Dec. 7, 2016, 7 pages.

International Search Report and Written Opinion dated Oct. 17, 2017, for PCT/EP2017/067273, filed on Jul. 10, 2017, 13 pages (German Language).

Jungbauer, S. et al. (2017). "Sex-dependent differences in the in vivo respiratory pheynotype of the TASK-1 potassium channel knockout mouse," *Respiratory Physiology & Neurobiology* 245: 13-28.

Kuppens, T. et al. (2004). "Determination of absolute configuration via vibrational circular dichroism," Drug Discovery Today: Technologies 1(3): 269-275.

Rowland, M. et al. (2011). "Well-Stirred Model of Hepatic Clearance" Appendix E in Clinical Pharmacokinetics and Pharmacodynamics Concepts and Applications, Fourth Edition, Troy, D. et al. eds., Lippincott Williams & Wilkins: Baltimore, MD, pp. 705-708.

(56) References Cited

OTHER PUBLICATIONS

Roy, A. et al. (2014). "Anandamide modulates carotid sinus nerve afferent activity via TRPV1 receptors increasing responses to heat," J. Appl. Physiol. 112: 212-224.
Stephens, P.J., (2004). "Vibrational Circular Dichroism Spectroscopy: A New Tool for the Stereochemical Characterization of Chiral Molecules" Chapter 26 in Computational Medicinal Chemistry for Drug Discovery, Bultinck, P. et al. eds., Marcel Dekker, Inc.: New York, NY, pp. 699-725.
International Search Report and Written Opinion dated Aug. 13, 2018, for PCT/EP2018/064980, filed on Jun. 7, 2018, 11 pages.
International Search Report and Written Opinion dated Jul. 6, 2018, for PCT/EP2018/064977, filed on Jun. 7, 2018, 12 pages (German Language).
U.S. Appl. No. 16/319,106, filed Jan. 18, 2019, for Delbeck et al., U.S. Patent Application is not submitted herewith pursuant to the waiver of 37 C.F.R. § 1.98(a)(2)(iii) issued by the Office dated Sep. 21, 2004.
U.S. Appl. No. 16/622,233, filed Dec. 12, 2019, for Delbeck et al., U.S. Patent Application is not submitted herewith pursuant to the waiver of 37 C.F.R. § 1.98(a)(2)(iii) issued by the Office dated Sep. 21, 2004.
U.S. Appl. No. 16/622,779, filed Dec. 13, 2019, for Delbeck et al., U.S. Patent Application is not submitted herewith pursuant to the waiver of 37 C.F.R. § 1.98(a)(2)(iii) issued by the Office dated Sep. 21, 2004.

\* cited by examiner

2-PHENYL-3-(PIPERAZINOMETHYL) IMIDAZO[1,2-A]PYRIDINE DERIVATIVES AS BLOCKERS OF TASK-1 AND TASK-2 CHANNELS, FOR THE TREATMENT OF SLEEP-RELATED BREATHING DISORDERS

CROSS REFERENCE TO RELATED APPLICATIONS

This application is a National Phase application under 35 U.S.C. § 371 of International Application No. PCT/EP2016/079973, filed Dec. 7, 2016, which claims priority benefit of European Application Nos. 16196836.7, filed Nov. 2, 2016, and 15199270.8, filed Dec. 10, 2015.

The present application relates to novel 2-phenyl-3-(piperazinomethyl)imidazo[1,2-a]pyridine derivatives, to processes for their preparation, to their use alone or in combinations for the treatment and/or prevention of diseases, and to their use for preparing medicaments for the treatment and/or prevention of diseases, in particular for treatment and/or prevention of respiratory disorders including, sleep-related respiratory disorders such as obstructive sleep apnoeas and central sleep apnoeas and snoring.

Potassium channels are virtually ubiquitous membrane proteins which are involved in a large number of different physiological processes. This also includes the regulation of the membrane potential and the electric excitability of neurons and muscle cells. Potassium channels are divided into three major groups which differ in the number of transmembrane domains (2, 4 or 6). The group of potassium channels where two pore-forming domains are flanked by four transmembrane domains is referred to as K2P channels. Functionally, the K2P channels mediate, substantially time- and voltage-independently, $K^+$ background currents, and their contribution to the maintenance of the resting membrane potential is crucial. The family of the K2P channels includes 15 members which are divided into six subfamilies, based on similarities in sequence, structure and function: TWIK, TREK, TASK, TALK, THIK and TRESK.

Of particular interest are TASK-1 (KCNK3 or K2P3.1) and TASK-3 (KCNK9 or K2P9.1) of the TASK (TWIK-related acid-sensitive $K^+$ channel) subfamily. Functionally, these channels are characterized in that, during maintenance of voltage-independent kinetics, they have "leak" or "background" streams flowing through them, and they respond to numerous physiological and pathological influences by increasing or decreasing their activity. Characteristic for TASK channels is the sensitive reaction to a change of the extracellular pH: At acidic pH, the channels are inhibited, and at alkaline pH, they are activated.

TASK-1 is expressed mainly in the central nervous system and in the cardiovascular system. Relevant expression of TASK-1 was demonstrated in the brain, in spinal ganglia, in motoneurons of the *Nervus hypoglossus* and *Nervus trigeminus*, in the heart, *Glomus caroticum*, the pulmonary artery, aorta, lung, pancreas, placenta, uterus, kidney, adrenal gland, small intestine and stomach, and also on T lymphocytes. TASK-3 is expressed mainly in the central nervous system. Relevant expression of TASK-3 was demonstrated in the brain, in motoneurons of the *Nervus hypoglossus* and *Nervus trigeminus* and in neuroepithelial cells of the *Glomus caroticum* and the lung, and also on T lymphocytes. A lower expression is found in the heart, stomach, testicular tissue and adrenal gland.

TASK-1 and TASK-3 channels play a role in respiratory regulation. Both channels are expressed in the respiratory neurons of the respiratory centre in the brain stem, inter alia in neurons which generate the respiratory rhythm (ventral respiratory group with pre-Bötzinger complex), and in the noradrenergic *Locus caeruleus*, and also in serotonergic neurons of the raphe nuclei. Owing to the pH dependency, here the TASK channels have the function of a sensor which translates changes in extracellular pH into corresponding cellular signals [Bayliss et al., *Pflugers Arch.* 467, 917-929 (2015)]. TASK-1 and TASK-3 are also expressed in the *Glomus caroticum*, a peripheral chemoreceptor which measures pH, $O_2$ and $CO_2$ content of the blood and transmits signals to the respiratory centre in the brain stem to regulate respiration. It was shown that TASK-1 knock-out mice have a reduced ventilatory response (increase of respiratory rate and tidal volume) to hypoxia and normoxic hypercapnia [Trapp et al., *J. Neurosci.* 28, 8844-8850 (2008)]. Furthermore, TASK-1 and TASK-3 channels were demonstrated in motoneurons of the *Nervus hypoglossus*, the XIIth cranial nerve, which has an important role in keeping the upper airways open [Berg et al., *J. Neurosci.* 24, 6693-6702 (2004)].

In a sleep apnoea model in the anaesthetized pig, intranasal administration of a potassium channel blocker which blocks the TASK-1 channel in the nanomolar range led to inhibition of collapsibility of the pharyngeal respiratory musculature and sensibilization of the negative pressure reflex of the upper airways. It is assumed that intranasal administration of the potassium channel blocker depolarizes mechanoreceptors in the upper airways and, via activation of the negative pressure reflex, leads to increased activity of the musculature of the upper airways, thus stabilizing the upper airways and preventing collapse. By virtue of this stabilization of the upper airways, the TASK channel blockade may be of great importance for obstructive sleep apnoea and also for snoring [Wirth et al., *Sleep* 36, 699-708 (2013); Kiper et al., *Pflugers Arch.* 467, 1081-1090 (2015)].

Obstructive sleep apnoea (OSA) is a sleep-related respiratory disorder which is characterized by repeat episodes of obstruction of the upper airways. When breathing in, the patency of the upper airways is ensured by the interaction of two opposite forces. The dilative effects of the musculature of the upper airways counteract the negative intraluminal pressure, which constricts the lumen. The active contraction of the diaphragm and the other auxiliary respiratory muscles generates a negative pressure in the airways, thus constituting the driving force for breathing. The stability of the upper respiratory tract is substantially determined by the coordination and contraction property of the dilating muscles of the upper airways.

The *Musculus genioglossus* plays a decisive role in the pathogenesis of obstructive sleep apnoea. The activity of the *Musculus genioglossus* increases with decreasing pressure in the pharynx in the sense of a dilative compensation mechanism. Innervated by the *Nervus hypoglossus*, it drives the tongue forward and downward, thus widening the pharyngeal airway [Verse et al., *Somnologie* 3, 14-20 (1999)]. Tensioning of the dilating muscles of the upper airways is modulated inter alia via mechanoreceptors/stretch receptors in the nasal cavity/pharynx [Bouillette et al., *J. Appl. Physiol. Respir. Environ. Exerc. Physiol.* 46, 772-779 (1979)]. In sleeping patients suffering from serious sleep apnoea, under local anaesthesia of the upper respiratory tract an additional reduction of the activity of the *Musculus genioglossus* can be observed [Berry et al., *Am. J. Respir. Crit. Care Med.* 156, 127-132 (1997)]. Patients suffering from obstructive sleep apnoea have high mortality and morbidity as a result of cardiovascular disorders such as hypertension, myocardial infarction and stroke [Vrints et al., *Acta Clin. Belg.* 68, 169-178 (2013)].

In the case of central sleep apnoea, owing to impaired brain function and impaired respiratory regulation there are episodic inhibitions of the respiratory drive. Central respiratory disorders result in mechanical respiratory arrests, i.e. during these episodes there is no breathing activity; temporarily, all respiratory muscles including the diaphragm are at rest. In the case of central sleep apnoea, there is no obstruction of the upper airways.

In the case of primary snoring, there is likewise no obstruction of the upper airways. However, owing to the constriction of the upper airways, the flow rate of the air that is inhaled and exhaled increases. This, combined with the relaxed musculature, causes the soft tissues of the oral cavity and the pharynx to flutter in the stream of air. This gentle vibration then generates the typical snoring noises.

Obstructive snoring (upper airway resistance syndrome, heavy snoring, hypopnoea syndrome) is caused by repeat partial obstruction of the upper airways during sleep. This results in an increased respiratory resistance and thus in an increase in work of breathing with considerable fluctuations in intrathoracic pressure. During inspiration, the negative intrathoracic pressure may reach values similar to those that are encountered as a result of complete airway obstruction during obstructive sleep apnoea. The pathophysiological consequences for heart, circulation and sleep quality correspond to those of obstructive sleep apnoea. As in obstructive sleep apnoea, the pathogenesis is assumed to be an impaired reflex mechanism of the pharynx-dilating muscles during inspiration when sleeping. Frequently, obstructive snoring is the preliminary stage of obstructive sleep apnoea [Hollandt et al., *HNO* 48, 628-634 (2000)].

In addition, TASK channels also appear to play a role in the apoptosis of neurons. In the animal model of myelin oligodendrocyte glycoprotein (MOG)-induced autoimmune encephalomyelitis, an animal model of multiple sclerosis, TASK-1 knock-out mice showed reduced neuronal degeneration. By preventing neuronal apoptosis, inhibition of TASK channels appears to act neuroprotectively, and may thus be of interest for the treatment of neurodegenerative disorders [Bittner et al., *Brain* 132, 2501-2516 (2009)].

Furthermore, it has been described that T lymphocytes express TASK-1 and TASK-3 channels and that inhibition of these channels leads to reduced cytokine production and proliferation after stimulation of T lymphocytes. The selective inhibition of TASK channels on T lymphocytes improved the course of the disease in an animal model of multiple sclerosis. The blockade of TASK channels may therefore also be of importance for treatment of autoimmune disorders [Meuth et al., *J. Biol. Chem.* 283, 14559-14579 (2008)].

TASK-1 and TASK-3 are also expressed in the heart [Rinne et al., *J. Mol. Cell. Cardiol.* 81, 71-80 (2015)]. Since TASK-1 is expressed particularly strongly in the nervous stimuli conduction system and in the atrium, this channel may have a role in disrupting stimuli conduction or triggering supraventricular arrhythmias. In the heart, TASK-1 appears to contribute to a background current which for its part contributes to maintenance of the resting potential, to action potential duration and to repolarization [Kim et al., *Am. J. Physiol.* 277 H1669-1678 (1999)]. Using human heart muscle cells, it was shown that blockade of the TASK-1 ion current results in a longer action potential [Limberg et al., *Cell. Physiol. Biochem.* 28, 613-624 (2011)]. Furthermore, for TASK-1 knock-out mice a prolonged QT time was demonstrated [Decher et al., *Cell.*  *Physiol. Biochem.* 28, 77-86 (2011)]. Inhibition of TASK channels may therefore be of importance for the treatment of cardiac arrythmias, in particular atrial fibrillation.

In certain vessels, TASK channels also appear to play a role in the regulation of the vascular tone. A relevant expression of TASK-1 was noticed in smooth muscles of pulmonary and mesenteric arteries. In studies on smooth muscle cells of human pulmonary arteries, it was shown that TASK-1 plays a role in the regulation of the pulmonary vascular tone. TASK-1 may be involved in hypoxic and acidose-induced pulmonary vasoconstriction [Tang et al., *Am. J. Respir. Cell. Mol. Biol.* 41, 476-483 (2009)].

In glomerulosa cells of the adrenal cortex, TASK-1 plays a role in potassium conductivity [Czirjak et al., *Mol. Endocrinol.* 14, 863-874 (2000)].

Possibly, TASK channels also play an important role in apoptosis and tumorigenesis. In breast cancer, colon cancer and lung cancer biopsies and also in metastasizing prostate cancer and in melanoma cells, TASK-3 has been found to be strongly overexpressed [Mu et al., *Cancer Cell* 3, 297-302 (2003); Kim et al., *APMIS* 112, 588-594 (2004); Pocsai et al., *Cell. Mol. Life Sci.* 63, 2364-2376 (2006)]. A point mutation at the TASK-3 channel, which switches off the channel function, simultaneously cancels the tumour-forming action (proliferation, tumour growth, apoptosis resistance) [Mu et al., *Cancer Cell* 3, 297-302 (2003)]. Overexpression of TASK-3 and TASK-1 in a murine fibroblast cell line (C8 cells) inhibits intracellular apoptosis routes [Liu et al., *Brain Res.* 1031, 164-173 (2005)]. Accordingly, the blockade of TASK channels may also be relevant for the treatment of various neoplastic disorders.

Therefore, it is an object of the present invention to provide novel substances which act as potent and selective blockers of TASK-1 and TASK-3 channels and, as such, are suitable in particular for the treatment and/or prevention of respiratory disorders including sleep-related respiratory disorders such as obstructive and central sleep apnoea and snoring, and also other disorders.

US 2002/0022624-A1 describes various azaindole derivatives including imidazo[1,2-a]pyridines as substance P antagonists for the treatment of CNS disorders. WO 2004/035578-A1 discloses 3-(aminomethyl)imidazo[1,2-a]pyridine derivatives as inhibitors of NO synthase which can be employed for the treatment of various disorders. WO 2009/143156-A2 claims 2-phenylimidazo[1,2-a]pyridine derivatives which, as modulators of $GABA_A$ receptors, are likewise suitable for treating CNS disorders. WO 2011/113606-A1 and WO 2012/143796-A2 disclose bicyclic imidazole derivatives suitable for the treatment of bacterial infections and inflammatory disorders. EP 2 671 582-A1 discloses bicyclic imidazole derivatives and options for their therapeutic use as inhibitors of T type calcium channels. WO 2012/130322-A1 describes 2,6-diaryl-3-(piperazinomethyl) imidazo[1,2-a]pyridine derivatives which, by virtue of their HIF-1 inhibiting activity, are suitable in particular for the treatment of inflammatory and hyperproliferative disorders. WO 2014/187922-A1 discloses various 2-phenyl-3-(piperazinomethyl)imidazo[1,2-a]pyridine derivatives as inhibitors of glucose transporters (GLUT) which can be employed for treating inflammatory, proliferative, metabolic, neurological and/or autoimmune disorders.

Furthermore, numerous {4-[(2-phenylimidazo[1,2-a]pyridin-3-yl)methyl]piperazin-1-yl}methanone derivatives of Chemical Abstracts are indexed as "Chemical Library" substances without literature reference, among others the compounds (4-{[2-(4-chlorophenyl)imidazo[1,2-a]pyridin-3-yl]
methyl}piperazin-1-yl)(cyclopropyl)methanone [CAS
Registry No. 1327935-11-4],
(3-chlorophenyl) {4-[(2-phenylimidazo[1,2-a]pyridin-3-yl)
methyl]piperazin-1-yl}methanone [CAS Registry No.
1300380-37-3],
(4-ethylphenyl){4-[(2-phenylimidazo[1,2-a]pyridin-3-yl)
methyl]piperazin-1-yl}methanone [CAS Registry No.
1296556-17-6],
phenyl{4-[(2-phenylimidazo[1,2-a]pyridin-3-yl)methyl]
piperazin-1-yl}methanone [CAS Registry No. 1062372-
04-6] and
cyclopropyl{4-[(2-phenylimidazo[1,2-a]pyridin-3-yl)
methyl]piperazin-1-yl}methanone [CAS Registry No.
950099-20-4].

A medical-therapeutic application has hitherto not been specifically described for the compounds mentioned.

Other (4-{[2-(4-chlorophenyl)imidazo[1,2-a]pyridin-3-yl]methyl}-piperazin-1-yl)methanone derivatives listed hereinbelow were likewise indexed by Chemical Abstracts at the respective given entry dates (ED) as "Chemical Library" substances without literature reference:
(4-{[2-(4-chlorophenyl)imidazo[1,2-a]pyridin-3-yl]
methyl}piperazin-1-yl)(2-methoxyphenyl)-methanone
[CAS Registry No. 1899197-66-0, ED 28 Apr. 2016],
(4-{[2-(4-chlorophenyl)imidazo[1,2-a]pyridin-3-yl]
methyl}piperazin-1-yl)(cyclohexyl) methanone [CAS
Registry No. 1899359-25-1, ED 28 Apr. 2016],
(4-{[2-(4-chlorophenyl)imidazo[1,2-a]pyridin-3-yl]
methyl}piperazin-1-yl)(tetrahydrofuran-2-yl)-methanone
[CAS Registry No. 1899359-35-3, ED 28 Apr. 2016],
(4-{[2-(4-chlorophenyl)imidazo[1,2-a]pyridin-3-yl]
methyl}piperazin-1-yl)(2-methylphenyl)-methanone
[CAS Registry No. 1906559-37-2, ED 9 May 2016],
(4-{[2-(4-chlorophenyl)imidazo[1,2-a]pyridin-3-yl]
methyl}piperazin-1-yl)(3-methoxyphenyl)-methanone
[CAS Registry No. 1906734-00-6, ED 9 May 2016],
(4-{[2-(4-chlorophenyl)imidazo[1,2-a]pyridin-3-yl]
methyl}piperazin-1-yl)(3-fluorophenyl)methanone [CAS
Registry No. 1906738-71-3, ED 9 May 2016],
(4-{[2-(4-chlorophenyl)imidazo[1,2-a]pyridin-3-yl]
methyl}piperazin-1-yl)(3-methylphenyl)-methanone
[CAS Registry No. 1907498-96-7, ED 10 May 2016],
(4-{[2-(4-chlorophenyl)imidazo [1,2-a]pyridin-3-yl]
methyl}piperazin-1-yl)(cyclobutyl)methanone [CAS
Registry No. 1907503-77-8, ED 10 May 2016], and
(4-{[2-(4-chlorophenyl)imidazo[1,2-a]pyridin-3-yl]
methyl}piperazin-1-yl)(2-fluorophenyl)methanone [CAS
Registry No. 1907618-99-8, ED 10 May 2016].

A medical-therapeutic application has likewise not been specifically described for these compounds.

The present invention provides compounds of the general formula (I)

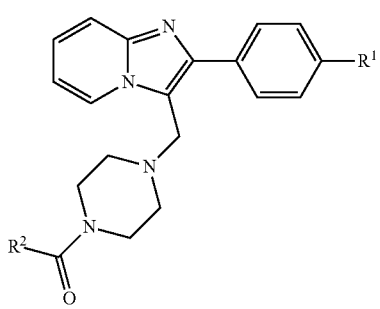

(I)

in which
$R^1$ represents halogen, cyano, $(C_1\text{-}C_4)$-alkyl, cyclopropyl or cyclobutyl
and
$R^2$ represents $(C_4\text{-}C_6)$-cycloalkyl in which a ring $CH_2$ group may be replaced by —O—
or
represents a phenyl group of the formula (a) or a pyridyl group of the formula (b)

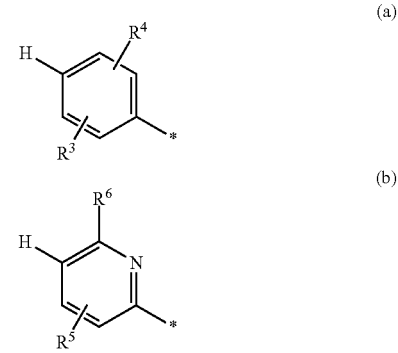

in which * marks the bond to the adjacent carbonyl group
and
$R^3$ represents fluorine, chlorine, bromine, cyano, $(C_1\text{-}C_3)$-alkyl or $(C_1\text{-}C_3)$-alkoxy,
where $(C_1\text{-}C_3)$-alkyl and $(C_1\text{-}C_3)$-alkoxy may be substituted up to three times by fluorine,
$R^4$ represents hydrogen, fluorine, chlorine, bromine or methyl,
$R^5$ represents hydrogen, fluorine, chlorine, bromine or methyl
and
$R^6$ represents hydrogen, $(C_1\text{-}C_3)$-alkoxy, cyclobutyloxy, oxetan-3-yloxy, tetrahydrofuran-3-yloxy or tetrahydro-2H-pyran-4-yloxy,
where $(C_1\text{-}C_3)$-alkoxy may be substituted up to three times by fluorine,
and the salts, solvates and solvates of the salts thereof.

Compounds of the invention are the compounds of the formula (I) and the salts, solvates and solvates of the salts thereof, the compounds that are encompassed by formula (I) and are of the formulae mentioned below and the salts, solvates and solvates of the salts thereof and the compounds that are encompassed by the formula (I) and are mentioned below as embodiments and the salts, solvates and solvates of the salts thereof if the compounds that are encompassed by the formula (I) and are mentioned below are not already salts, solvates and solvates of the salts.

Preferred salts in the context of the present invention are physiologically acceptable salts of the compounds of the invention. Also encompassed are salts which are not themselves suitable for pharmaceutical applications but can be used, for example, for the isolation, purification or storage of the compounds of the invention.

Physiologically acceptable salts of the compounds of the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, benzenesulphonic acid, toluenesulphonic acid, naphthalenedisulphonic acid, formic acid, acetic acid, trifluoroacetic acid, propionic acid, succinic acid, fumaric acid, maleic acid, lactic acid, tartaric acid, malic acid, citric acid, gluconic acid, benzoic acid and embonic acid.

Solvates in the context of the invention are described as those forms of the compounds of the invention which form a complex in the solid or liquid state by coordination with solvent molecules. Hydrates are a specific form of the solvates in which the coordination is with water. Solvates preferred in the context of the present invention are hydrates.

The compounds of the invention may, depending on their structure, exist in different stereoisomeric forms, i.e. in the form of configurational isomers or else, if appropriate, as conformational isomers (enantiomers and/or diastereomers, including those in the case of atropisomers). The present invention therefore encompasses the enantiomers and diastereomers, and the respective mixtures thereof. The stereoisomerically homogeneous constituents can be isolated from such mixtures of enantiomers and/or diastereomers in a known manner; chromatography processes are preferably used for this purpose, especially HPLC chromatography on an achiral or chiral phase.

If the compounds of the invention can occur in tautomeric forms, the present invention encompasses all the tautomeric forms.

The present invention also encompasses all suitable isotopic variants of the compounds of the invention. An isotopic variant of a compound of the invention is understood here to mean a compound in which at least one atom within the compound of the invention has been exchanged for another atom of the same atomic number, but with a different atomic mass from the atomic mass which usually or predominantly occurs in nature. Examples of isotopes which can be incorporated into a compound of the invention are those of hydrogen, carbon, nitrogen, oxygen, phosphorus, sulphur, fluorine, chlorine, bromine and iodine, such as $^2H$ (deuterium), $^3H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$. Particular isotopic variants of a compound of the invention, especially those in which one or more radioactive isotopes have been incorporated, may be beneficial, for example, for the examination of the mechanism of action or of the active ingredient distribution in the body; due to comparatively easy preparability and detectability, especially compounds labelled with $^3H$ or $^{14}C$ isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds of the invention may therefore possibly also constitute a preferred embodiment of the present invention. Isotopic variants of the compounds of the invention can be prepared by commonly used processes known to those skilled in the art, for example by the methods described further down and the procedures described in the working examples, by using corresponding isotopic modifications of the respective reagents and/or starting compounds.

The present invention additionally also encompasses prodrugs of the compounds of the invention. The term "prodrugs" refers here to compounds which may themselves be biologically active or inactive, but are converted while present in the body, for example by a metabolic or hydrolytic route, to compounds of the invention.

In the context of the present invention, unless specified otherwise, the substituents and radicals are defined as follows:

In the context of the invention, ($C_1$-$C_4$)-alkyl represents a straight-chain or branched alkyl radical having 1 to 4 carbon atoms. Examples include: methyl, ethyl, n-propyl, isopropyl, n-butyl, isobutyl, sec-butyl and tert-butyl.

In the context of the invention, ($C_1$-$C_3$)-alkyl represents a straight-chain or branched alkyl radical having 1 to 3 carbon atoms. Examples include: methyl, ethyl, n-propyl and isopropyl.

($C_1$-$C_3$)-Alkoxy in the context of the invention represents a straight-chain or branched alkoxy radical having 1 to 3 carbon atoms. Examples include: methoxy, ethoxy, n-propoxy and isopropoxy.

($C_4$-$C_6$)-Cycloalkyl in the context of the invention represents a monocyclic saturated cycloalkyl group having 4 to 6 carbon atoms. Examples include: cyclobutyl, cyclopentyl and cyclohexyl.

Halogen in the context of the invention includes fluorine, chlorine, bromine and iodine. Preference is given to fluorine, chlorine or bromine.

In the context of the present invention, all radicals which occur more than once are defined independently of one another. When radicals in the compounds of the invention are substituted, the radicals may be mono- or polysubstituted, unless specified otherwise. Substitution by one substituent or by two identical or different substituents is preferred. Particular preference is given to substitution by one substituent.

Preference is given in the context of the present invention to compounds of the formula (I) in which $R^1$ represents fluorine, chlorine, bromine, methyl, isopropyl, tert-butyl or cyclopropyl
and
$R^2$ represents cyclobutyl, cyclopentyl or cyclohexyl
or
represents a phenyl group of the formula (a) or a pyridyl group of the formula (b)

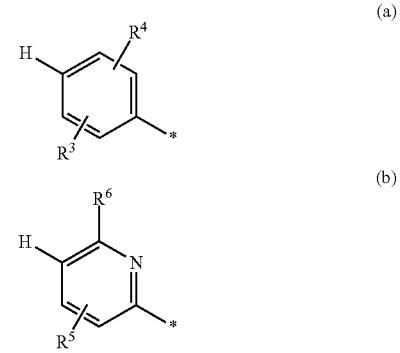

in which * marks the bond to the adjacent carbonyl group
and
$R^3$ represents fluorine, chlorine, cyano, ($C_1$-$C_3$)-alkyl, ($C_1$-$C_3$)-alkoxy or trifluoromethoxy,
$R^4$ represents hydrogen, fluorine or chlorine,
$R^5$ represents hydrogen, fluorine, chlorine, bromine or methyl
and
$R^6$ represents hydrogen or ($C_1$-$C_3$)-alkoxy which may be substituted up to three times by fluorine,
and the salts, solvates and solvates of the salts thereof.

A particular embodiment of the present invention relates to compounds of the formula (I) in which
$R^1$ represents chlorine or bromine,
and the salts, solvates and solvates of the salts thereof.

A further particular embodiment of the present invention relates to compounds of the formula (I) in which $R^1$ represents methyl, isopropyl, tert-butyl or cyclopropyl, and the salts, solvates and solvates of the salts thereof.

A further particular embodiment of the present invention relates to compounds of the formula (I) in which $R^2$ represents cyclobutyl, cyclopentyl or cyclohexyl, and the salts, solvates and solvates of the salts thereof.

A further particular embodiment of the present invention relates to compounds of the formula (I) in which $R^2$ represents a phenyl group of the formula (a)

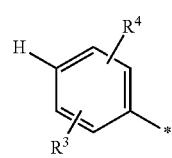

(a)

in which * marks the bond to the adjacent carbonyl group, $R^3$ represents fluorine, chlorine, cyano, $(C_1-C_3)$-alkyl or $(C_1-C_3)$-alkoxy and $R^4$ represents hydrogen, fluorine or chlorine, and the salts, solvates and solvates of the salts thereof.

A further particular embodiment of the present invention relates to compounds of the formula (I) in which $R^2$ represents a pyridyl group of the formula (b)

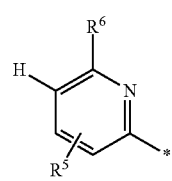

(b)

in which * marks the bond to the adjacent carbonyl group, $R^5$ represents hydrogen, chlorine or bromine and $R^6$ represents $(C_1-C_3)$-alkoxy which may be substituted up to three times by fluorine, and the salts, solvates and solvates of the salts thereof.

In the context of the present invention, particular preference is given to compounds of the formula (I) in which $R^1$ represents chlorine, bromine, isopropyl or cyclopropyl and $R^2$ represents cyclobutyl, cyclopentyl or cyclohexyl or represents a phenyl group of the formula (a) or a pyridyl group of the formula (b)

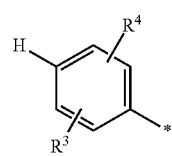

(a)

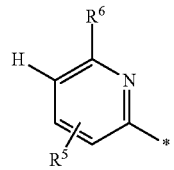

(b)

in which * marks the bond to the adjacent carbonyl group and $R^3$ represents fluorine, chlorine, cyano, methyl, isopropyl, methoxy or ethoxy, $R^4$ represents hydrogen, fluorine or chlorine, $R^5$ represents hydrogen, chlorine or bromine and $R^6$ represents methoxy, difluoromethoxy, trifluoromethoxy or isopropoxy, and the salts, solvates and solvates of the salts thereof.

Irrespective of the particular combinations of the radicals specified, the individual radical definitions specified in the particular combinations or preferred combinations of radicals are also replaced as desired by radical definitions from other combinations.

Very particular preference is given to combinations of two or more of the abovementioned preferred ranges.

The invention furthermore provides a process for preparing the compounds of the formula (I) according to the invention, characterized in that a compound of the formula (II)

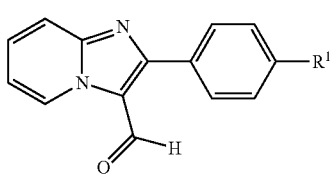

(II)

in which $R^1$ has the meaning given above is reacted in the presence of a suitable reducing agent either

[A] with a compound of the formula (III)

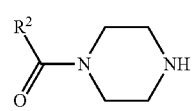

(III)

in which $R^2$ has the meaning given above or

[B] with a protected piperazine derivative of the formula (IV)

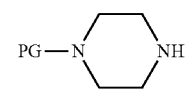

(IV)

in which PG represents a suitable amino protective group such as, for example, tert-butoxycarbonyl, benzyloxycarbonyl or (9H-fluoren-9-ylmethoxy)carbonyl, to give initially a compound of the formula (V)

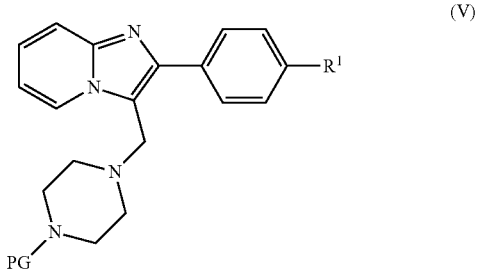

(V)

in which PG and R¹ have the meanings given above,
the protective group PG is then removed and the resulting compound of the formula (VI)

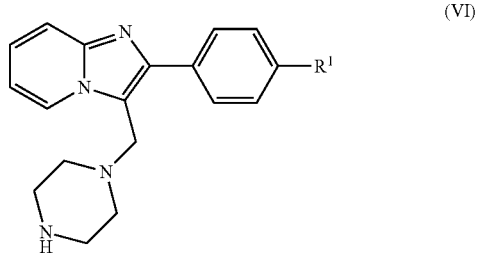

(VI)

in which R¹ has the meaning given above
is then reacted with a carboxylic acid of the formula (VII)

(VII)

in which R² has the meaning given above
with activation of the carboxylic acid function in (VII) or is reacted with the corresponding acid chloride of the formula (VIII)

(VIII)

in which R² has the meaning given above
and the resulting compounds of the formula (I) are optionally converted with the appropriate (i) solvents and/or (ii) acids into their solvates, salts and/or solvates of the salts.

Suitable reducing agents for the process steps [A] (II)+(III)→(I) and [B] (II)+(IV)→(V) [reductive aminations] for such purposes are customary alkali metal borohydrides such as sodium borohydride, sodium cyanoborohydride or sodium triacetoxyborohydride; preference is given to using sodium triacetoxyborohydride. The addition of an acid, such as acetic acid in particular, and/or of a dehydrating agent, for example molecular sieve or trimethyl orthoformate or triethyl orthoformate, may be advantageous in these reactions. Suitable solvents for these reactions are especially alcohols such as methanol, ethanol, n-propanol or isopropanol, ethers such as diisopropyl ether, methyl tert-butyl ether, tetrahydrofuran, 1,4-dioxane or 1,2-dimethoxyethane, polar aprotic solvents such as acetonitrile or N,N-dimethylformamide (DMF) or mixtures of such solvents; preference is given to using tetrahydrofuran. The reactions are generally carried out in a temperature range of 0° C. to +50° C.

Suitable for use as protective group PG in compound (IV) may be a customary amino protective group such as tert-butoxycarbonyl (Boc), benzyloxycarbonyl (Z) or (9H-fluoren-9-ylmethoxy)carbonyl (Fmoc); preference is given to using tert-butoxycarbonyl (Boc). The removal of the protective group in process step [B] (V)→(VI) is carried out by known methods. Thus, the tert-butoxycarbonyl group is usually removed by treatment with a strong acid such as hydrogen chloride, hydrogen bromide or trifluoroacetic acid, in an inert solvent such as diethyl ether, 1,4-dioxane, dichloromethane or acetic acid. In the case of benzyloxycarbonyl as protective group, this is preferably removal by hydrogenolysis in the presence of a suitable palladium catalyst such as palladium on activated carbon. The (9H-fluoren-9-yl-methoxy)carbonyl group is generally removed with the aid of a secondary amine base such as diethylamine or piperidine [see, for example, T. W. Greene and P. G. M. Wuts, *Protective Groups in Organic Synthesis*, Wiley, New York, 1999; P. J. Kocienski, *Protecting Groups*, 3$^{rd}$ edition, Thieme, 2005].

The process step [B] (VI)+(VII)→(I) [amide formation] is carried out by known methods with the aid of a condensing or activating agent. Suitable such agents are, for example, carbodiimides such as N,N'-diethyl-, N,N'-dipropyl-, N,N'-diisopropyl-, N,N'-dicyclohexylcarbodiimide (DCC) or N-(3-dimethylaminopropyl)-N'-ethylcarbodiimide hydrochloride (EDC), phosgene derivatives such as N,N'-carbonyldiimidazole (CDI) or isobutyl chloroformate, 1,2-oxazolium compounds such as 2-ethyl-5-phenyl-1,2-oxazolium 3-sulphate or 2-tert-butyl-5-methylisoxazolium perchlorate, acylamino compounds such as 2-ethoxy-1-ethoxycarbonyl-1,2-dihydroquinoline, α-chloroenamines such as 1-chloro-N,N,2-trimethylprop-1-en-1-amine, 1,3,5-triazine derivatives such as 4-(4,6-dimethoxy-1,3,5-triazin-2-yl)-4-methylmorpholinium chloride, phosphorus compounds such as n-propanephosphonic anhydride (PPA), diethyl cyanophosphonate, diphenylphosphoryl azide (DPPA), bis(2-oxo-3-oxazolidinyl)phosphoryl chloride, benzotriazol-1-yloxytris(dimethylamino)phosphonium hexafluorophosphate or benzotriazol-1-yloxytris(pyrrolidino)phosphonium hexafluorophosphate (PyBOP), or uronium compounds such as O-(benzotriazol-1-yl)-N,N,N',N'-tetramethyluronium tetrafluoroborate (TBTU), O-(1H-6-chlorobenzotriazol-1-yl)-1,1,3,3-tetramethyluronium tetrafluoroborate (TCTU), O-(benzotriazol-1-yl)-N,N,N',N'-tetramethyluronium hexafluorophosphate (HBTU), O-(7-azabenzotriazol-1-yl)-N,N,N',N'-tetramethyluronium hexafluorophosphate (HATU) or 2-(2-oxo-1-(2H)-pyridyl)-1,1,3,3-tetramethyluronium tetrafluoroborate (TPTU), optionally in combination with further auxiliaries such as 1-hydroxybenzotriazole (HOBt) or N-hydroxysuccinimide (HOSu), and also as base an alkali metal carbonate, e.g. sodium carbonate or potassium carbonate, or a tertiary amine base such as triethylamine, N,N-diisopropylethylamine, N-methylmorpholine (NMM), N-methylpiperidine (NMP), pyridine or 4-N,N-dimethylaminopyridine (DMAP). The preferred condensing or activating agent used is 1-chloro-N,N,2-trimethylprop-1-en-1-amine in combination with pyridine as base or O-(7-azabenzotriazol-1-yl)-N,N,N',N'-tetramethyluronium hexafluorophosphate (HATU) in combination with N,N-diisopropylethylamine.

The alternative process via the carbonyl chloride (VIII) [(VI)+(VIII)→(I)] is generally carried out in the presence of a base such as sodium carbonate, potassium carbonate, triethylamine, N,N-diisopropylethylamine, N-methylmorpholine (NMM), N-methylpiperidine (NMP), pyridine, 2,6-dimethylpyridine, 4-N,N-dimethylaminopyridine (DMAP), 1,8-diazabicyclo[5.4.0]undec-7-ene (DBU) or 1,5-diazabicyclo[4.3.0]non-5-ene (DBN); preference is given to using triethylamine or N,N-diisopropylethylamine.

Suitable inert solvents for these amide forming reactions are, for example, ethers such as diethyl ether, diisopropyl ether, methyl tert-butyl ether, tetrahydrofuran, 1,4-dioxane, 1,2-dimethoxyethane or bis(2-methoxyethyl) ether, hydrocarbons such as benzene, toluene, xylene, pentane, hexane or cyclohexane, halohydrocarbons such as dichloromethane, trichloromethane, carbon tetrachloride, 1,2-dichloroethane, trichloroethylene or chlorobenzene, or polar aprotic solvents such as acetone, methyl ethyl ketone, ethyl acetate, acetonitrile, butyronitrile, pyridine, dimethyl sulphoxide (DMSO), N,N-dimethylformamide (DMF), N,N'-dimethylpropyleneurea (DMPU) or N-methylpyrrolidinone (NMP); it is also possible to use mixtures of such solvents. Preference is given to using dichloromethane, tetrahydrofuran, N,N-dimethylformamide or mixtures of these solvents.

The reactions are generally carried out within a temperature range of from −20° C. to +60° C., preferably at from 0° C. to +40° C.

In process steps [B] (VI)+(VII)→(I) and (VI)+(VIII)→(I), the amine compound (VI) can also be employed in the form of a salt, for example as hydrochloride or trifluoroacetate. In such a case, the reaction is carried out in the presence of an appropriately increased amount of the respective auxiliary base used.

The processes described above can be carried out at atmospheric, elevated or reduced pressure (for example in the range from 0.5 to 5 bar); in general, the reactions are each carried out at atmospheric pressure.

For their part, the compounds of the formula (II) can be prepared by processes known from the literature by condensing 2-aminopyridine (IX)

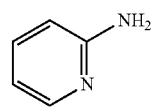
(IX)

in the presence of a base with an acetophenone derivative of the formula (X)

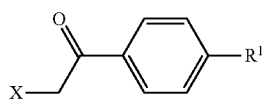
(X)

in which $R^1$ has the meaning given above
and

X represents a suitable leaving group such as, for example, chlorine, bromine or iodine, to give a 2-phenylimidazo[1,2-a]pyridine of the formula (XI)

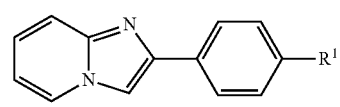
(XI)

in which $R^1$ has the meaning given above
and then formylating this with a mixture of N,N-dimethylformamide and phosphorus oxychloride to give (II).

The condensation reaction (IX)+(X)→(XI) is usually carried out in an alcoholic solvent such as methanol, ethanol, n-propanol, isopropanol or n-butanol, in an ether such as diethyl ether, diisopropyl ether, methyl tert-butyl ether, tetrahydrofuran, 1,4-dioxane, 1,2-dimethoxyethane or bis(2-methoxyethyl) ether, or in a dipolar aprotic solvent such as N,N-dimethylformamide (DMF), N,N'-dimethylpropyleneurea (DMPU) or N-methylpyrrolidinone (NMP), at a temperature in the range from +20° C. to +120° C.; preferably, the solvent used is ethanol.

Bases suitable for this reaction are in particular alkali metal bicarbonates or carbonates such as sodium bicarbonate or potassium bicarbonate or lithium carbonate, sodium carbonate, potassium carbonate or caesium carbonate, or else alumina; preference is given to using sodium bicarbonate. Optionally—if the reaction temperature is increased correspondingly—the reaction can also be carried out without addition of a base.

The regioselective formylation (XI)-(II) is carried out under the customary conditions of a Vilsmaier-Haack reaction by treating (XI) with a pre-formed mixture of N,N-dimethylformamide and phosphorus oxychloride which is employed in a large excess and simultaneously also serves as solvent. The reaction is generally carried out in a temperature range of from 0° C. to +100° C.

The compounds of the formulae (III), (IV), (VII), (VIII), (IX) and (X) are either commercially available or described as such in the literature, or they can be prepared in a simple manner from other commercially available compounds by methods familiar to the person skilled in the art and known from the literature. Numerous detailed procedures and further literature references can also be found in the experimental section, in the section on the preparation of the starting compounds and intermediates.

The preparation of the compounds according to the invention can be illustrated by way of example by the following reaction scheme:

Scheme 1

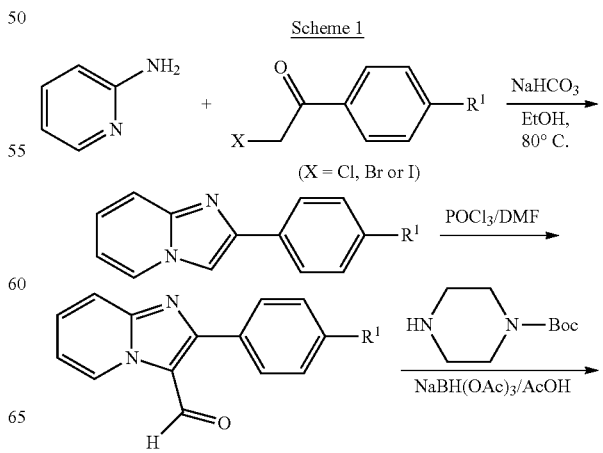

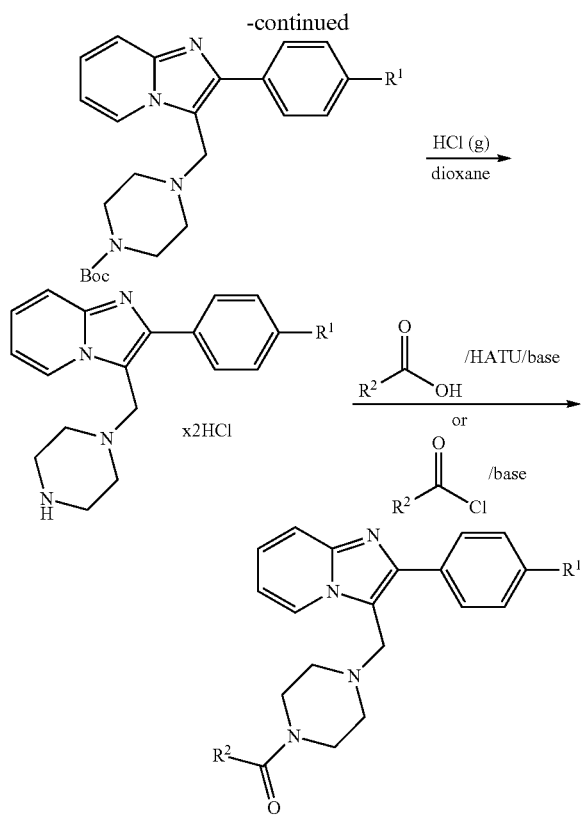

The compounds of the invention have valuable pharmacological properties and can be used for prevention and treatment of diseases in humans and animals.

The compounds according to the invention are potent and selective blockers of TASK-1 and TASK-3 channels and are therefore suitable for the treatment and/or prevention of disorders and pathological processes, in particular those caused by activation of TASK-1 and/or TASK-3 or by activated TASK-1 and/or TASK-3, and of disorders secondary to damage caused by TASK-1 and/or TASK-3.

For the purpose of the present invention, this includes in particular disorders from the group of the respiratory disorders and sleep-related respiratory disorders, such as obstructive sleep apnoea (in adults and children), primary snoring, obstructive snoring (upper airway resistance syndrome, heavy snoring, hypopnoea syndrome), central sleep apnoea, mixed sleep apnoeas, Cheyne-Stokes respiration, primary sleep apnoea of infancy, apparent life-threatening event, central sleep apnoea as a result of the use of medicaments or the use of other substances, obesity hypoventilation syndrome, disrupted central respiratory drive, sudden infant death, primary alveolar hypoventilation syndrome, postoperative hypoxia and apnoea, muscular respiratory disorders, respiratory disorders following long-term ventilation, respiratory disorders during adaptation in high mountains, acute and chronic pulmonary diseases with hypoxia and hypercapnia, sleep-related non-obstructive alveolar hypoventilation and the congenital central alveolar hypoventilation syndrome.

The compounds according to the invention can furthermore be used for the treatment and/or prevention of neurodegenerative disorders such as dementia, dementia with Lewy bodies, Alzheimer's disease, Parkinson's disease, Huntington's disease, Pick's disease, Wilson's disease, progressive supranuclear paresis, corticobasal degeneration, tauopathy, frontotemporal dementia and parkinsonism linked to chromosome 17, multisystem atrophy, spinocerebellar ataxias, spinobulbar muscular atrophy of the Kennedy type, Friedreich's ataxia, dentatorubral-pallidoluysian atrophy, amyotrophic lateral sclerosis, primary lateral sclerosis, spinal muscular atrophy, Creutzfeldt-Jakob disease and variants of Creutzfeldt-Jakob disease, infantile neuroaxonal dystrophy, neurodegeneration with brain iron accumulation, frontotemporal lobar degeneration with ubiquitin proteasome system and familial encephalopathy with neuroserpin inclusions.

In addition, the compounds according to the invention can be employed for the treatment and/or prevention of neuroinflammatory and neuroimmunological disorders of the central nervous system (CNS) such as, for example, multiple sclerosis (Encephalomyelitis disseminata), transverse myelitis, Neuromyelitis optica, acute disseminated encephalomyelitis, optic neuritis, meningitis, encephalitis, demyelinating diseases and also inflammatory vascular changes in the central nervous system.

Moreover, the compounds according to the invention are suitable for the treatment and/or prevention of neoplastic disorders such as, for example, skin cancer, breast cancer, lung cancer, colon cancer and prostate cancer.

Also, the compounds according to the invention are suitable for the treatment and/or prevention of cardiac arrhythmias, for example atrial and ventricular arrhythmias, conduction defects such as first- to third-degree atrio-ventricular blocks, supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, sick sinus syndrome, syncopes and AV nodal re-entrant tachycardia.

Further cardiovascular disorders where the compounds according to the invention can be employed for treatment and/or prevention are, for example, heart failure, coronary heart disease, stable and unstable angina pectoris, high blood pressure (hypertension), pulmonary-arterial hypertension (PAH) and other forms of pulmonary hypertension (PH), renal hypertension, peripheral and cardial vascular disorders, Wolff-Parkinson-White syndrome, acute coronary syndrome (ACS), autoimmune cardiac disorders (pericarditis, endocarditis, valvolitis, aortitis, cardiomyopathies), boxer cardiomyopathy, aneurysms, shock such as cardiogenic shock, septic shock and anaphylactic shock, furthermore thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation such as, for example, pulmonary oedema, cerebral oedema, renal oedema or oedema caused by heart failure, peripheral circulatory disturbances, reperfusion damage, arterial and venous thromboses, microalbuminuria, myocardial insufficiency, endothelial dysfunction, micro- and macrovascular damage (vasculitis), and also to prevent restenoses, for example after thrombolysis therapies, percutaneous transluminal angioplasties (PTA), percutaneous transluminal coronary angioplasties (PTCA), heart transplants and bypass operations.

In the context of the present invention, the term "heart failure" encompasses both acute and chronic forms of heart failure, and also specific or related disease types thereof, such as acute decompensated heart failure, right heart failure, left heart failure, global failure, ischaemic cardiomyopathy, dilatative cardiomyopathy, hypertrophic cardiomyopathy, idiopathic cardiomyopathy, congenital heart defects, heart valve defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders and diastolic and systolic heart failure.

The compounds of the invention can additionally be used for treatment and/or prevention of asthmatic disorders of varying severity with intermittent or persistent characteristics (refractive asthma, bronchial asthma, allergic asthma, intrinsic asthma, extrinsic asthma, medicament- or dust-induced asthma), of various forms of bronchitis (chronic bronchitis, infectious bronchitis, eosinophilic bronchitis), of bronchiectasis, pneumonia, farmer's lung and related disorders, coughs and colds (chronic inflammatory cough, iatrogenic cough), inflammation of the nasal mucosa (including medicament-related rhinitis, vasomotoric rhinitis and seasonal allergic rhinitis, for example hay fever) and of polyps.

The compounds of the invention are also suitable for the treatment and/or prevention of renal disorders, in particular renal insufficiency and kidney failure. In the context of the present invention, the terms "renal insufficiency" and "kidney failure" encompass both acute and chronic manifestations thereof and also underlying or related renal disorders such as renal hypoperfusion, intradialytic hypotension, obstructive uropathy, glomerulopathies, glomerulonephritis, acute glomerulonephritis, glomerulosclerosis, tubulointerstitial diseases, nephropathic disorders such as primary and congenital kidney disease, nephritis, immunological kidney disorders such as kidney transplant rejection and immuno-complex-induced kidney disorders, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome which can be characterized diagnostically, for example by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphataemia and/or need for dialysis. The present invention also encompasses the use of the compounds of the invention for the treatment and/or prevention of sequelae of renal insufficiency, for example hypertension, pulmonary oedema, heart failure, uraemia, anaemia, electrolyte disturbances (for example hyperkalaemia, hyponatraemia) and disturbances in bone and carbohydrate metabolism.

In addition, the compounds of the invention are suitable for the treatment and/or prevention of disorders of the urogenital system such as, for example, benign prostate syndrome (BPS), benign prostate hyperplasia (BPH), benign prostate enlargement (BPE), bladder outlet obstruction (BOO), lower urinary tract syndromes (LUTS), neurogenic overactive bladder (OAB), incontinence such as, for example, mixed urinary incontinence, urge urinary incontinence, stress urinary incontinence or overflow urinary incontinence (MUI, UUI, SUI, OUI), pelvic pain, and also erectile dysfunction and female sexual dysfunction.

The compounds according to the invention are furthermore suitable for treatment and/or prevention of inflammatory disorders and autoimmune disorders such as, for example, rheumatoid disorders, inflammatory eye disorders, chronic obstructive pulmonary disease (COPD), acute respiratory distress syndrome (ARDS), acute lung injury (ALI), alpha-1-antitrypsin deficiency (AATD), pulmonary emphysema (e.g. pulmonary emphysema induced by cigarette smoke), cystic fibrosis (CF), sepsis (SIRS), multiple organ failure (MODS, MOF), inflammatory disorders of the kidney, chronic intestinal inflammations (IBD, Crohn's disease, ulcerative colitis), pancreatitis, peritonitis, cystitis, urethritis, prostatitis, epidimytitis, oophoritis, salpingitis and vulvovaginitis, and also for the treatment and/or prevention of fibrotic disorders of internal organs such as, for example, the lung, the heart, the kidney, the bone marrow and especially the liver, of dermatological fibroses and of fibrotic disorders of the eye. In the context of the present invention, the term "fibrotic disorders" includes in particular disorders such as hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis, peritoneal fibrosis and similar fibrotic disorders, scleroderma, morphoea, keloids, hypertrophic scarring, naevi, diabetic retinopathy, proliferative vitroretinopathy and disorders of the connective tissue (for example sarcoidosis). The compounds of the invention can likewise be used for promoting wound healing, for controlling postoperative scarring, for example following glaucoma operations and cosmetically for ageing or keratinized skin.

In addition, the compounds according to the invention can be used for the treatment and/or prevention of arteriosclerosis, disorders of lipid metabolism and dyslipidaemias (hypolipoproteinaemia, hypertriglyceridaemia, hyperlipidaemia, combined hyperlipidaemias, hypercholesterinaemia, abetalipoproteinaemia, sitosterolaemia), xanthomatosis, Tangier disease, adiposity, obesity, metabolic disorders (metabolic syndrome, hyperglycaemia, insulin-dependent diabetes, non-insulin-dependent diabetes, gestation diabetes, hyperinsulinaemia, insulin resistance, glucose intolerance and diabetic sequelae such as retinopathy, nephropathy and neuropathy), anaemias such as haemolytic anaemias, in particular haemoglobinopathies such as sickle-cell anaemia and thalassaemias, megaloblastic anaemias, iron deficiency anaemias, anaemias owing to acute blood loss, displacement anaemias and aplastic anaemias, of disorders of the gastrointestinal tract and the abdomen (glossitis, gingivitis, periodontitis, oesophagitis, eosinophilic gastroenteritis, mastocytosis, Crohn's disease, colitis, proctitis, pruritis ani, diarrhoea, coeliac disease, hepatitis, liver fibrosis, liver cirrhosis, pancreatitis and cholecystitis), disorders of the central nervous system (stroke, epilepsy, depressions), immune disorders, disorders of the thyroid (hyperthyreosis), skin disorders (psoriasis, acne, eczemas, neurodermitis, multifarious forms of dermatitis, keratitis, bullosis, vasculitis, cellulitis, panniculitis, lupus erythematodes, erythema, lymphoma, skin cancer, Sweet syndrome, Weber-Christian syndrome, scarring, formation of warts, chilblains), inflammatory eye disorders (saccoidosis, blepharitis, conjunctivitis, iritis, uveitis, chorioiditis, ophthalmitis), viral disorders (caused by influenza-, adeno- and coronaviruses such as, for example, HPV, HCMV, HIV, SARS), of disorders of skeletal bone, the joints and skeletal muscle, of inflammatory changes of the arteries (multifarious forms of arteritis such as endarteritis, mesarteritis, periarteritis, panarteritis, rheumatic arteritis, deformans arteritis, temporal arteritis, cranial arteritis, giant-cell arteritis and granulomatous arteritis, and the Horton's syndrome, Churg-Strauss syndrome and Takayasu arteritis), Muckle-Well syndrome, Kikuchi's disease, of polychondritis, scleroderm and also of other disorders having an inflammatory or immunological component, such as cataract, cachexia, osteoporosis, gout, incontinence, leprosy, Sezary syndrome and paraneoplastic syndrome, for rejection reactions following organ transplantations and for wound healing and angiogenesis, in particular in the case of chronic wounds.

By virtue of their property profile, the compounds according to the invention are preferably suitable for treatment and/or prevention of respiratory disorders, in particular of sleep-related respiratory disorders such as obstructive and central sleep apnoeas and also primary and obstructive snoring, for treatment and/or prevention of cardiac arrhythmias and also for treatment and/or prevention of neurodegenerative, neuroinflammatory and neuroimmunological disorders.

The aforementioned well-characterized diseases in humans can also occur with comparable aetiology in other mammals and can likewise be treated therein with the compounds of the present invention.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is used here synonymously with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

The present invention thus further provides for the use of the compounds of the invention for treatment and/or prevention of disorders, especially of the aforementioned disorders.

The present invention further provides for the use of the compounds of the invention for production of a medicament for treatment and/or prevention of disorders, especially of the aforementioned disorders.

The present invention further provides a medicament comprising at least one of the compounds of the invention for treatment and/or prevention of disorders, especially of the aforementioned disorders.

The present invention further provides for the use of the compounds of the invention in a method for treatment and/or prevention of disorders, especially of the aforementioned disorders.

The present invention further provides a method for treatment and/or prevention of disorders, especially of the aforementioned disorders, using an effective amount of at least one of the compounds of the invention.

The compounds of the invention can be used alone or, if required, in combination with one or more other pharmacologically active substances, provided that this combination does not lead to undesirable and unacceptable side effects. Accordingly, the present invention further provides medicaments comprising at least one of the compounds of the invention and one or more further active ingredients, especially for treatment and/or prevention of the aforementioned disorders.

Preferred examples of combination active ingredients suitable for the purpose include:

respiratory stimulants such as, by way of example and with preference, theophylline, doxapram, nikethamide or caffeine;

psychostimulants such as, by way of example and with preference, modafinil or armodafinil;

amphetamines and amphetamine derivatives such as, by way of example and with preference, amphetamine, metamphetamine or methylphenidate;

serotonin reuptake inhibitors such as, by way of example and with preference, fluoxetine, paroxetine, citalopram, escitalopram, sertraline, fluvoxamine or trazodone;

serotonin precursors such as, by way of example and with preference, L-tryptophan;

selective serotonin noradrenaline reuptake inhibitors such as, by way of example and with preference, venlafaxine or duloxetine;

noradrenergic and specific serotonergic antidepressants such as, by way of example and with preference, mirtazapine;

selective noradrenaline reuptake inhibitors such as, by way of example and with preference, reboxetine;

tricyclic antidepressants such as, by way of example and with preference, amitriptyline, protriptyline, doxepine, trimipramine, imipramine, clomipramine or desipramine;

alpha2-adrenergic agonists such as, by way of example and with preference, clonidine;

GABA agonists such as, by way of example and with preference, baclofen;

alpha sympathomimetics such as, by way of example and with preference, xylometazoline, oxymetazoline, phenylephrine, naphazoline, tetryzoline or tramazoline;

glucocorticoids such as, by way of example and with preference, fluticasone, budesonide, beclometasone, mometasone, tixocortol or triamcinolone;

cannabinoid receptor agonists;

carboanhydrase inhibitors such as, by way of example and with preference, acetazolamide, methazolamide or diclofenamide;

opioid and benzodiazepine receptor antagonists such as, by way of example and with preference, flumazenil, naloxone or naltrexone;

cholinesterase inhibitors such as, by way of example and with preference, neostigmine, pyridostigmine, physostigmine donepezil, galantamine or rivastigmine;

N-methyl-D-aspartate and glutamate antagonists such as, by way of example and with preference, amantadine, memantine or sabeluzole;

nicotine receptor agonists;

leukotriene receptor antagonists such as, by way of example and with preference, montelukast or tripelukast;

dopamine receptor antagonists such as, by way of example and with preference, dromperidone, metoclopramide or benzamide, butyrophenone or phenothiazine derivatives;

appetite suppressants such as, by way of example and with preference, sibutramin, topiramate, phentermine, lipase inhibitors or cannabinoid receptor antagonists;

proton pump inhibitors such as, by way of example and with preference, pantoprazole, omeprazole, esomeprazole, lansoprazole or rabeprazole;

organic nitrates and NO donors, for example sodium nitroprusside, nitroglycerin, isosorbide mononitrate, isosorbide dinitrate, molsidomine or SIN-1, and inhaled NO;

compounds which inhibit the degradation of cyclic guanosine monophosphate (cGMP) and/or cyclic adenosine monophosphate (cAMP), for example inhibitors of phosphodiesterases (PDE) 1, 2, 3, 4 and/or 5, especially PDE 5 inhibitors such as sildenafil, vardenafil, tadalafil, udenafil, dasantafil, avanafil, mirodenafil or lodenafil;

NO- and haem-independent activators of soluble guanylate cyclase (sGC), such as in particular the compounds described in WO 01/19355, WO 01/19776, WO 01/19778, WO 01/19780, WO 02/070462 and WO 02/070510;

NO-independent but haem-dependent stimulators of soluble guanylate cyclase (sGC), such as in particular riociguat, vericiguat and the compounds described in WO 00/06568, WO 00/06569, WO 02/42301, WO 03/095451, WO 2011/147809, WO 2012/004258, WO 2012/028647 and WO 2012/059549;

prostacyclin analogues and IP receptor agonists, by way of example and with preference iloprost, beraprost, treprostinil, epoprostenol or selexipag;

endothelin receptor antagonists, by way of example and with preference bosentan, darusentan, ambrisentan or sitaxsentan;

compounds which inhibit human neutrophile elastase (HNE), by way of example and with preference sivelestat or DX-890 (reltran);

compounds which inhibit the degradation and alteration of the extracellular matrix, by way of example and with preference inhibitors of the matrix metalloproteases (MMPs), especially inhibitors of stromelysin, collagenases, gelatinases and aggrecanases (in this context particularly of MMP-1, MMP-3, MMP-8, MMP-9, MMP-10, MMP-11 and MMP-13) and of metalloelastase (MMP-12);

compounds which block the binding of serotonin to its receptors, by way of example and with preference antagonists of the 5-$HT_{2B}$ receptor such as PRX-08066;

antagonists of growth factors, cytokines and chemokines, by way of example and with preference antagonists of TGF-β, CTGF, IL-1, IL-4, IL-5, IL-6, IL-8, IL-13 and integrins;

Rho kinase-inhibiting compounds, by way of example and with preference fasudil, Y-27632, SLx-2119, BF-66851, BF-66852, BF-66853, KI-23095 or BA-1049;

compounds which influence the energy metabolism of the heart, by way of example and with preference etomoxir, dichloroacetate, ranolazine or trimetazidine;

compounds which inhibit the signal transduction cascade, by way of example and with preference from the group of the kinase inhibitors, in particular from the group of the tyrosine kinase and/or serine/threonine kinase inhibitors, by way of example and with preference nintedanib, dasatinib, nilotinib, bosutinib, regorafenib, sorafenib, sunitinib, cediranib, axitinib, telatinib, imatinib, brivanib, pazopanib, vatalanib, gefitinib, erlotinib, lapatinib, canertinib, lestaurtinib, pelitinib, semaxanib or tandutinib;

anti-obstructive agents as used, for example, for treatment of chronic obstructive pulmonary disease (COPD) or bronchial asthma, by way of example and with preference from the group of the inhalatively or systemically administered agonists of the beta-adrenergic receptor (beta-mimetics) and the inhalatively administered antimuscarinergic substances;

antiinflammatory, immunomodulating, immunosuppressive and/or cytotoxic agents, by way of example and with preference from the group of the systemically or inhalatively administered corticosteroids and also dimethyl fumarate, fingolimod, glatiramer acetate, β-interferons, natalizumab, teriflunomide, mitoxantrone, immunoglobulins, acetylcysteine, montelukast, tipelukast, azathioprine, cyclophosphamide, hydroxycarbamide, azithromycin, interferon-γ, pirfenidone or etanercept;

antifibrotic agents such as, by way of example and with preference, lysophosphatidic acid receptor 1 (LPA-1) antagonists, CTGF inhibitors, IL-4 antagonists, IL-13 antagonists, TGF-β antagonists or pirfenidone;

antithrombotic agents, by way of example and with preference from the group of platelet aggregation inhibitors, the anticoagulants and the profibrinolytic substances;

hypotensive active ingredients, by way of example and with preference from the group of the calcium antagonists, angiotensin AII antagonists, ACE inhibitors, vasopeptidase inhibitors, endothelin antagonists, renin inhibitors, alpha receptor blockers, beta receptor blockers, mineralocorticoid receptor antagonists and also the diuretics; and/or active compounds altering lipid metabolism, for example and with preference from the group of the thyroid receptor agonists, cholesterol synthesis inhibitors such as, by way of example and preferably, HMG-CoA reductase inhibitors or squalene synthesis inhibitors, the ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists.

In a preferred embodiment of the invention, the compounds of the invention are administered in combination with a beta-adrenergic receptor agonist, by way of example and with preference albuterol, isoproterenol, metaproterenol, terbutalin, fenoterol, formoterol, reproterol, salbutamol or salmeterol.

In a preferred embodiment of the invention, the compounds of the invention are administered in combination with an antimuscarinergic substance, by way of example and with preference ipratropium bromide, tiotropium bromide or oxitropium bromide.

In a preferred embodiment of the invention, the compounds of the invention are administered in combination with a corticosteroid, by way of example and with preference prednisone, prednisolone, methylprednisolone, triamcinolone, dexamethasone, betamethasone, beclomethasone, flunisolide, budesonide or fluticasone.

Antithrombotic agents are preferably understood to mean compounds from the group of the platelet aggregation inhibitors, the anticoagulants and the profibrinolytic substances.

In a preferred embodiment of the invention, the compounds of the invention are administered in combination with a platelet aggregation inhibitor, by way of example and with preference aspirin, clopidogrel, ticlopidine or dipyridamole.

In a preferred embodiment of the invention, the compounds of the invention are administered in combination with a thrombin inhibitor, by way of example and with preference ximelagatran, melagatran, dabigatran, bivalirudin or clexane.

In a preferred embodiment of the invention, the compounds of the invention are administered in combination with a GPIIb/IIIa antagonist, by way of example and with preference tirofiban or abciximab.

In a preferred embodiment of the invention, the compounds of the invention are administered in combination with a factor Xa inhibitor, by way of example and with preference rivaroxaban, apixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds of the invention are administered in combination with heparin or with a low molecular weight (LMW) heparin derivative.

In a preferred embodiment of the invention, the compounds of the invention are administered in combination with a vitamin K antagonist, by way of example and with preference coumarin.

Hypotensive agents are preferably understood to mean compounds from the group of the calcium antagonists, angiotensin AII antagonists, ACE inhibitors, endothelin antagonists, renin inhibitors, alpha-receptor blockers, beta-receptor blockers, mineralocorticoid receptor antagonists, and the diuretics.

In a preferred embodiment of the invention, the compounds of the invention are administered in combination with a calcium antagonist, by way of example and with preference nifedipine, amlodipine, verapamil or diltiazem.

In a preferred embodiment of the invention, the compounds of the invention are administered in combination with an alpha-1-receptor blocker, by way of example and with preference prazosin.

In a preferred embodiment of the invention, the compounds of the invention are administered in combination with a beta-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the inventive compounds are administered in combination with an angiotensin AII antagonist, preferred examples being losartan, candesartan, valsartan, telmisartan or embusartan.

In a preferred embodiment of the invention, the compounds of the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds of the invention are administered in combination with an endothelin antagonist, by way of example and with preference bosentan, darusentan, ambrisentan or sitaxsentan.

In a preferred embodiment of the invention, the compounds of the invention are administered in combination with a renin inhibitor, by way of example and with preference aliskiren, SPP-600 or SPP-800.

In a preferred embodiment of the invention, the compounds of the invention are administered in combination with a mineralocorticoid receptor antagonist, by way of example and with preference spironolactone, eplerenone or finerenone.

In a preferred embodiment of the invention, the compounds of the invention are administered in combination with a diuretic, by way of example and with preference furosemide, bumetanide, torsemide, bendroflumethiazide, chlorothiazide, hydrochlorothiazide, hydroflumethiazide, methyclothiazide, polythiazide, trichlormethiazide, chlorthalidone, indapamide, metolazone, quinethazone, acetazolamide, dichlorphenamide, methazolamide, glycerol, isosorbide, mannitol, amiloride or triamterene.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and the lipoprotein(a) antagonists.

In a preferred embodiment of the invention, the compounds of the invention are administered in combination with a CETP inhibitor, by way of example and with preference torcetrapib (CP-529 414), JJT-705 or CETP vaccine (Avant).

In a preferred embodiment of the invention, the compounds of the invention are administered in combination with a thyroid receptor agonist such as, for example and preferably, D-thyroxine, 3,5,3'-triiodothyronine (T3), CGS 23425 or axitirome (CGS 26214).

In a preferred embodiment of the invention, the compounds of the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds of the invention are administered in combination with a squalene synthesis inhibitor, by way of example and with preference BMS-188494 or TAK-475.

In a preferred embodiment of the invention, the compounds of the invention are administered in combination with an ACAT inhibitor, by way of example and with preference avasimibe, melinamide, pactimibe, eflucimibe or SMP-797.

In a preferred embodiment of the invention, the compounds of the invention are administered in combination with an MTP inhibitor, by way of example and with preference implitapide, BMS-201038, R-103757 or JTT-130.

In a preferred embodiment of the invention, the inventive compounds are administered in combination with a PPAR-gamma agonist, by way of example and with preference pioglitazone or rosiglitazone.

In a preferred embodiment of the invention, the compounds of the invention are administered in combination with a PPAR-delta agonist, by way of example and with preference GW 501516 or BAY 68-5042.

In a preferred embodiment of the invention, the compounds of the invention are administered in combination with a cholesterol absorption inhibitor, by way of example and with preference ezetimibe, tiqueside or pamaqueside.

In a preferred embodiment of the invention, the compounds of the invention are administered in combination with a lipase inhibitor, by way of example and with preference orlistat.

In a preferred embodiment of the invention, the compounds of the invention are administered in combination with a polymeric bile acid adsorbent, by way of example and with preference cholestyramine, colestipol, colesolvam, CholestaGel or colestimide.

In a preferred embodiment of the invention, the compounds of the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the compounds of the invention are administered in combination with a lipoprotein(a) antagonist, by way of example and with preference gemcabene calcium (CI-1027) or nicotinic acid.

Particular preference is given to combinations of the compounds according to the invention with one or more further active compounds selected from the group consisting of respiratory stimulants, psychostimulants, serotonin reuptake inhibitors, noradrenergic, serotonergic and tricyclic antidepressants, sGC stimulators, mineralocorticoid receptor antagonists, antiinflammatory drugs, immunomodulators, immunosuppressives and cytotoxic drugs.

If required, the substances according to the invention can also be employed in conjunction with the use of one or more medical technical devices or auxiliaries, provided this does not lead to unwanted and unacceptable side-effects. Medical devices and auxiliaries suitable for such a combined application are, by way of example and with preference:
  devices for positive airway pressure ventilation such as, by way of example and with preference, CPAP (continuous positive airway pressure) devices, BiPAP (bi-level positive airway pressure) devices and IPPV (intermittent positive pressure ventilation) devices;
  neurostimulators of the *Nervus hypoglossus;*
  intraoral auxiliaries such as, by way of example and with preference, protrusion braces;
  nasal disposable valves;
  nasal stents.

The present invention further provides medicaments which comprise at least one compound of the invention, typically together with one or more inert, nontoxic, pharmaceutically suitable excipients, and for the use thereof for the aforementioned purposes.

The compounds of the invention can act systemically and/or locally. For this purpose, they can be administered in a suitable manner, for example by the oral, parenteral, pulmonal, intrapulmonal (inhalative), nasal, intranasal, pharyngeal, lingual, sublingual, buccal, rectal, dermal, transdermal, conjunctival or otic route, or as an implant or stent.

The compounds of the invention can be administered in administration forms suitable for these administration routes.

Suitable administration forms for oral administration are those which work according to the prior art and release the compounds of the invention rapidly and/or in a modified manner and which contain the compounds of the invention in crystalline and/or amorphized and/or dissolved form, for example tablets (uncoated or coated tablets, for example with gastric juice-resistant or retarded-dissolution or insoluble coatings which control the release of the compound of the invention), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can bypass an absorption step (e.g. take place intravenously, intraarterially, intracardially, intraspinally or intralumbally) or include an absorption (e.g. take place inhalatively, intramuscularly, subcutaneously, intracutaneously, percutaneously or intraperitoneally). Administration forms suitable for parenteral administration include preparations for injection and infusion in the form of solutions, suspensions, emulsions, lyophilisates or sterile powders.

For the other administration routes, suitable examples are inhalable medicament forms (including powder inhalers, nebulizers, metered aerosols), nasal drops, solutions or sprays, throat sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Preference is given to oral, intravenous, intranasal and pharyngeal administration.

According to one embodiment, the administration is effected intranasally. According to one embodiment, the intranasal administration is effected with the aid of nose drops or a nasal spray.

According to one embodiment, the intranasal administration is effected with the aid of a nasal spray.

The compounds of the invention can be converted to the administration forms mentioned. This can be accomplished in a manner known per se by mixing with inert, nontoxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulfate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and flavour and/or odour correctants.

In general, it has been found to be advantageous in the case of parenteral administration to administer amounts of about 0.001 to 1 mg/kg, preferably about 0.01 to 0.5 mg/kg, of body weight to achieve effective results. In the case of oral administration the dosage is about 0.01 to 100 mg/kg, preferably about 0.01 to 20 mg/kg and most preferably 0.1 to 10 mg/kg of body weight.

According to one embodiment, the dosage in the case of intranasal administration is about 0.1 µg to 500 µg per day. According to a further embodiment, the dosage in the case of intranasal administration is about 1 µg to 250 µg per day. According to a further embodiment, the dosage in the case of intranasal administration is about 1 µg to 120 µg per day. According to a further embodiment, the dose of about 0.1 µg to 500 µg per day, or of about 1 µg to 250 µg per day, or of about 1 µg to 120 µg per day, is administered intranasally once per day, before bedtime. According to one embodiment, the dose of about 0.1 µg to 500 µg per day, or of about 1 µg to 250 µg per day, or of about 1 µg to 120 µg per day, is administered once per day, in each case half into each nostril. According to one embodiment, the dose of about 0.1 µg to 500 µg per day, or of about 1 µg to 250 µg per day, or of about 1 µg to 120 µg per day, is administered once per day before bedtime, in each case half into each nostril.

It may nevertheless be necessary in some cases to deviate from the stated amounts, specifically as a function of the body weight, route of administration, individual response to the active ingredient, nature of the preparation and time or interval over which administration takes place. Thus, in some cases less than the abovementioned minimum amount may be sufficient, while in other cases the upper limit mentioned must be exceeded. In the case of administration of greater amounts, it may be advisable to divide them into several individual doses over the day.

The working examples which follow illustrate the invention. The invention is not restricted to the examples.

A. EXAMPLES

Abbreviations and Acronyms abs. absolute
Ac acetyl
aq. aqueous, aqueous solution
Boc tert-butoxycarbonyl
br. broad (in NMR signal)
Ex. Example
Bu butyl
c concentration
ca. circa, about
cat. catalytic
CI chemical ionization (in MS)
d doublet (in NMR)
d day(s)
DCI direct chemical ionization (in MS)
dd doublet of doublets (in NMR)
DMF N,N-dimethylformamide
DMSO dimethyl sulphoxide
dq doublet of quartets (in NMR)
dt doublet of triplets (in NMR)
EI electron impact ionization (in MS)
eq. equivalent(s)
ESI electrospray ionization (in MS)
Et ethyl
h hour(s)
HATU O-(7-azabenzotriazol-1-yl)-N,N,N',N'-tetramethyluronium hexafluorophosphate
HOBt 1-hydroxy-1H-benzotriazole hydrate
HPLC high-pressure, high-performance liquid chromatography
iPr isopropyl
conc. concentrated (in the case of a solution)
LC liquid chromatography
LC-MS liquid chromatography-coupled mass spectrometry
Lit. literature (reference)
m multiplet (in NMR)
Me methyl
min minute(s)
MS mass spectrometry
NMR nuclear magnetic resonance spectrometry
Ph phenyl
Pr propyl
q quartet (in NMR)
quant. quantitative (in chemical yield)
RP reverse phase (in HPLC)
RT room temperature
$R_t$ retention time (in HPLC, LC-MS)
s singlet (in NMR)
t triplet (in NMR)
tBu tert-butyl
TFA trifluoroacetic acid
THF tetrahydrofuran
UV ultraviolet spectrometry
v/v volume to volume ratio (of a solution)
tog. together LC-MS and HPLC Methods:

Method 1 (LC-MS):

Instrument: Waters Acquity SQD UPLC System; column: Waters Acquity UPLC HSS T3 1.8 µm, 50 mm×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; temperature: 50° C.; flow rate: 0.40 ml/min; UV detection: 208-400 nm.

Method 2 (LC-MS):

MS instrument: Thermo Scientific FT-MS; UHPLC instrument: Thermo Scientific UltiMate 3000; column: Waters HSS T3 C18 1.8 µm, 75 mm×2.1 mm; mobile phase A: 1 l of water+0.01% formic acid, mobile phase B: 1 l of acetonitrile+0.01% formic acid; gradient: 0.0 min 10% B→2.5 min 95% B→3.5 min 95% B; temperature: 50° C.; flow rate: 0.90 ml/min; UV detection: 210-300 nm.

Method 3 (LC-MS):

MS instrument: Waters Micromass QM; HPLC instrument: Agilent 1100 Series; column: Agilent ZORBAX Extend-C18 3.5 µm, 50 mm×3.0 mm; mobile phase A: 1 l of water+0.01 mol ammonium carbonate, mobile phase B: 1 l of acetonitrile; gradient: 0.0 min 98% A→0.2 min 98% A→3.0 min 5% A→4.5 min 5% A; temperature: 40° C.; flow rate: 1.75 ml/min; UV detection: 210 nm.

Method 4 (LC-MS):

MS instrument: Waters Micromass Quattro Micro; HPLC instrument: Waters UPLC Acquity; column: Waters BEH C18 1.7 µm, 50 mm×2.1 mm; mobile phase A: 1 l of water+0.01 mol ammonium formate, mobile phase B: 1 l of acetonitrile; gradient: 0.0 min 95% A→0.1 min 95% A→2.0 min 15% A→2.5 min 15% A→2.51 min 10% A→3.0 min 10% A; temperature: 40° C.; flow rate: 0.5 ml/min; UV detection: 210 nm.

Method 5 (LC-MS):

Instrument: Agilent MS Quad 6150 with HPLC Agilent 1290; column: Waters Acquity UPLC HSS T3 1.8 µm, 50 mm×2.1 mm; mobile phase A: 1 l of water+0.25 ml of 99% strength formic acid, mobile phase B: 1 l of acetonitrile+0.25 ml of 99% strength formic acid; gradient: 0.0 min 90% A→0.3 min 90% A→1.7 min 5% A→3.0 min 5% A; flow rate: 1.20 ml/min; temperature: 50° C.; UV detection: 205-305 nm.

Method 6 (Preparative HPLC):

Instrument: Abimed Gilson 305; column: Reprosil C18 10 µm, 250 mm×30 mm; mobile phase A: water, mobile phase B: acetonitrile; gradient: 0-3 min 10% B, 3-27 min 10% B→95% B, 27-34.5 min 95% B, 34.5-35.5 min 95% B→10% B, 35.5-36.5 min 10% B; flow rate: 50 ml/min; room temperature; UV detection: 210 nm.

Further Details:

The descriptions of the coupling patterns of $^1$H NMR signals which follow are guided by the visual appearance of the signals in question and do not necessarily correspond to a strict, physically correct interpretation. In general, the stated chemical shift refers to the centre of the signal in question; in the case of broad multiplets, an interval is generally given.

Melting points and melting-point ranges, if stated, are uncorrected.

In cases where the reaction products were obtained by trituration, stirring or recrystallization, it was frequently possible to isolate further amounts of product from the respective mother liquor by chromatography. However, a description of this chromatography is dispensed with hereinbelow unless a large part of the total yield could only be isolated in this step.

All reactants or reagents whose preparation is not described explicitly hereinafter were purchased commercially from generally accessible sources. For all other reactants or reagents whose preparation is likewise not described hereinafter and which were not commercially obtainable or were obtained from sources which are not generally accessible, a reference is given to the published literature in which their preparation is described.

Starting Materials and Intermediates

Example 1A 2-(4-Chlorophenyl)imidazo[1,2-a]pyridine

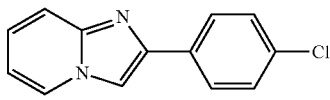 [SMILES: Clc1ccc(-c2cn3ccccc3n2)cc1]

10.95 g (130 mmol) of sodium bicarbonate were added to a solution of 20 g (85.65 mmol) of 2-bromo-1-(4-chlorophenyl)ethanone and 8.87 g (94.22 mmol) of pyridine-2-amine in 200 ml of ethanol, and the mixture was stirred at 80° C. for 5 hours. The reaction was then cooled first to room temperature and then to 0° C. (ice bath). The resulting precipitate was filtered off and washed repeatedly with an ethanol/water mixture (2:1). The solid was then dried under reduced pressure at 40° C. overnight. This gave 19.8 g of the target product, which was used in the subsequent reactions without further purification.

$^1$H-NMR (400 MHz, DMSO-$d_6$, δ/ppm): 6.87-6.94 (m, 1H), 7.23-7.29 (m, 1H), 7.50 (d, 2H), 7.58 (d, 1H), 7.99 (d, 2H), 8.43 (s, 1H), 8.53 (d, 1H).

LC-MS (Method 1): $R_t$=0.58 min; m/z=229/231 (M+H)$^+$.

Analogously to Example 1A, the following compounds were prepared from the starting materials stated in each case:

| Example | Name/Structure/Starting materials | Analytical data |
|---|---|---|
| 2A | 2-(4-bromophenyl)imidazo[1,2-a]pyridine<br><br>from 2-bromo-1-(4-bromophenyl)ethanone and pyridine-2-amine | $^1$H-NMR (400 MHz, DMSO-$d_6$, δ/ppm): 6.88-6.94 (m, 1H), 7.23-7.29 (m, 1H), 7.58 (d, 1H), 7.63 (d, 2H), 7.92 (d, 2H), 8.44 (s, 1H), 8.53 (d, 1H).<br>LC-MS (Method 1):<br>$R_t$ = 0.63 min; m/z = 273/275 (M + H)$^+$. |
| 3A | 2-(4-fluorophenyl)imidazo[1,2-a]pyridine<br><br>from 2-bromo-1-(4-fluorophenyl)ethanone and pyridine-2-amine | $^1$H-NMR (400 MHz, DMSO-$d_6$, δ/ppm): 6.90 (t, 1H), 7.20-7.32 (m, 3H), 7.57 (d, 1H), 8.00 (dd, 2H), 8.38 (s, 1H), 8.52 (d, 1H).<br>LC-MS (Method 1):<br>$R_t$ = 0.49 min; m/z = 213 (M + H)$^+$. |
| 4A | 2-(4-isopropylphenyl)imidazo[1,2-a]pyridine<br><br>from 2-bromo-1-(4-isopropylphenyl)ethanone and pyridine-2-amine | $^1$H-NMR (400 MHz, DMSO-$d_6$, δ/ppm): 1.23 (d, 6H), 2.85-2.96 (m, 1H), 6.88 (t, 1H), 7.19-7.26 (m, 1H), 7.31 (d, 2H), 7.56 (d, 1H), 7.88 (d, 2H), 8.34 (s, 1H), 8.51 (d, 1H).<br>LC-MS (Method 1):<br>$R_t$ = 0.68 min; m/z = 237 (M + H)$^+$. |
| 5A | 2-(4-methylphenyl)imidazo[1,2-a]pyridine<br><br>from 2-bromo-1-(4-methylphenyl)ethanone and pyridine-2-amine | $^1$H-NMR (400 MHz, DMSO-$d_6$, δ/ppm): 2.33 (s, 3H), 6.88 (t, 1H), 7.18-7.29 (m, 3H), 7.55 (d, 1H), 7.85 (d, 2H), 8.34 (s, 1H), 8.50 (d, 1H).<br>LC-MS (Method 1):<br>$R_t$ = 0.49 min; m/z = 209 (M + H)$^+$. |

| Example | Name/Structure/Starting materials | Analytical data |
|---|---|---|
| 6A | 4-(imidazo[1,2-a]pyridin-2-yl)benzonitrile 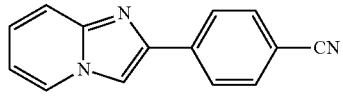 from 4-(bromoacetyl)benzonitrile and pyridine-2-amine | $^1$H-NMR (400 MHz, DMSO-d$_6$, δ/ppm): 6.94 (t, 1H), 7.30 (dd, 1H), 7.61 (d, 1H), 7.90 (d, 2H), 8.15 (d, 2H), 8.56 (d, 1H), 8.59 (s, 1H). LC-MS (Method 1): R$_t$ = 0.51 min; m/z = 220 (M + H)$^+$. |

Example 7A

2-(4-tert-Butylphenyl)imidazo[1,2-a]pyridine

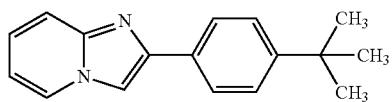

A mixture of 1 g (5.67 mmol) of 1-(4-tert-butylphenyl)ethanone, 1.23 g (13.05 mmol) of pyridine-2-amine and 1.728 g (6.81 mmol) of iodine was stirred at a temperature of 120° C. for 2 hours. 15 ml of water and 8.51 ml of 1 N aqueous sodium hydroxide solution were then added, and the mixture was stirred at 100° C. for a further hour. After cooling to room temperature, about 100 ml of water and about 100 ml of ethyl acetate were added. After separation of the phases, the organic phase was washed twice with water, dried over magnesium sulphate, filtered and concentrated to dryness under reduced pressure. The residue obtained was applied to silica gel and purified by column chromatography on silica gel (Biotage 100 g KP-sil; flow rate: 100 ml/min; mobile phase gradient: 1.3 min cyclohexane/ethyl acetate 92:8→over 13 min cyclohexane/ethyl acetate 34:66→2.6 min cyclohexane/ethyl acetate 34:66). This gave 970 mg (3.87 mmol, 68% of theory) of the target compound.

$^1$H-NMR (400 MHz, DMSO-d$_6$, δ/ppm): 1.32 (s, 9H), 6.88 (t, 1H), 7.19-7.26 (m, 1H), 7.46 (d, 2H), 7.57 (d, 1H), 7.88 (d, 2H), 8.34 (s, 1H), 8.51 (d, 1H).

LC-MS (Method 1): R$_t$=0.72 min; m/z=251 (M+H)$^+$.

Example 8A

2-(4-Chlorophenyl)imidazo[1,2-a]pyridine-3-carbaldehyde

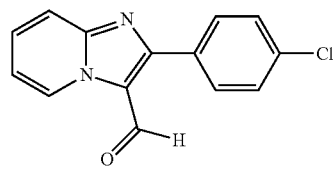 [SMILES: O=Cc1c(-c2ccc(Cl)cc2)nc2ccccn12]

300 ml of DMF were cooled to 0° C. 44 ml (470.08 mmol) of phosphorus oxychloride were then slowly added dropwise. The reaction solution was then slowly warmed to room temperature and stirred at this temperature for another hour. 43 g (188.03 mmol) of 2-(4-chlorophenyl)imidazo[1,2-a]pyridine were then added a little at a time. During the addition, the reaction solution warmed to 35° C. After the addition has ended, the reaction mixture was heated to 80° C. and stirred at this temperature for 2 hours. After cooling to room temperature, the solution was slowly added to 3 litres of ice-water. The resulting solid was filtered off with suction, washed repeatedly with water and dried in a high-vacuum drying cabinet at 40° C. overnight. This gave 39.6 g (154.27 mmol, 82% of theory) of the target product.

$^1$H-NMR (400 MHz, DMSO-d$_6$, δ/ppm): 7.37 (t, 1H), 7.63 (d, 2H), 7.78 (t, 1H), 7.90-7.99 (m, 3H), 9.58 (d, 1H), 10.02 (s, 1H).

LC-MS (Method 1): R$_t$=0.97 min; m/z=257/259 (M+H)$^+$.

Analogously to Example 8A, the following compounds were prepared from the starting material stated in each case:

| Example | Name/Structure/Starting material | Analytical data |
|---|---|---|
| 9A | 2-(4-bromophenyl)imidazo[1,2-a]pyridine-3-carbaldehyde 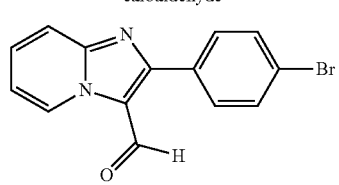 from 2-(4-bromophenyl)imidazo[1,2-a]pyridine | $^1$H-NMR (400 MHz, DMSO-d$_6$, δ/ppm): 7.35 (t, 1H), 7.72-7.80 (m, 3H), 7.85-7.95 (m, 3H), 9.58 (d, 1H), 10.02 (s, 1H). LC-MS (Method 2): R$_t$ = 1.76 min; m/z = 301/303 (M + H)$^+$. |

-continued

| Example | Name/Structure/Starting material | Analytical data |
|---|---|---|
| 10A | 2-(4-fluorophenyl)imidazo[1,2-a]pyridine-3-carbaldehyde<br><br>from 2-(4-fluorophenyl)imidazo[1,2-a]pyridine | $^1$H-NMR (400 MHz, DMSO-$d_6$, δ/ppm): 7.32-7.45 (m, 3H), 7.77 (t, 1H), 7.92 (d, 1H), 7.99 (dd, 2H), 9.58 (d, 1H), 10.01 (s, 1H).<br>LC-MS (Method 1):<br>$R_t$ = 0.79 min; m/z = 241 (M + H)$^+$. |
| 11A | 2-(4-isopropylphenyl)imidazo[1,2-a]pyridine-3-carbaldehyde<br><br>from 2-(4-isopropylphenyl)imidazo[1,2-a]pyridine | $^1$H-NMR (400 MHz, DMSO-$d_6$, δ/ppm): 1.27 (d, 6H), 2.93-3.05 (m, 1H), 7.33 (t, 1H), 7.44 (d, 2H), 7.74 (t, 1H), 7.85 (d, 2H), 7.91 (d, 1H), 9.58 (d, 1H), 10.03 (s, 1H).<br>LC-MS (Method 1):<br>$R_t$ = 1.03 min; m/z = 265 (M + H)$^+$. |
| 12A | 2-(4-methylphenyl)imidazo[1,2-a]pyridine-3-carbaldehyde<br><br>from 2-(4-methylphenyl)imidazo[1,2-a]pyridine | $^1$H-NMR (400 MHz, DMSO-$d_6$, δ/ppm): 2.41 (s, 3H), 7.34-7.43 (m, 3H), 7.77-7.86 (m, 3H), 7.94 (d, 1H), 9.60 (d, 1H), 10.02 (s, 1H).<br>LC-MS (Method 1):<br>$R_t$ = 0.89 min; m/z = 237 (M + H)$^+$. |
| 13A | 4-(3-formylimidazo[1,2-a]pyridin-2-yl)benzonitrile<br><br>from 4-(imidazo[1,2-a]pyridin-2-yl)benzonitrile | $^1$H-NMR (400 MHz, DMSO-$d_6$, δ/ppm): 7.38 (t, 1H), 7.79 (t, 1H), 7.96 (d, 1H), 8.03 (d, 2H), 8.14 (d, 2H), 9.59 (d, 1H), 10.05 (s, 1H).<br>LC-MS (Method 1):<br>$R_t$ = 0.77 min; m/z = 248 (M + H)$^+$. |
| 14A | 2-(4-tert-butylphenyl)imidazo[1,2-a]pyridine-3-carbaldehyde<br><br>from 2-(4-tert-butylphenyl)imidazo[1,2-a]pyridine | $^1$H-NMR (400 MHz, DMSO-$d_6$, δ/ppm): 1.35 (s, 9H), 7.35 (t, 1H), 7.59 (d, 2H), 7.73-7.80 (m, 1H), 7.87 (d, 2H), 7.89-7.97 (m, 1H), 9.59 (d, 1H), 10.04 (s, 1H).<br>LC-MS (Method 2):<br>$R_t$ = 2.13 min; m/z = 279 (M + H)$^+$. |

Example 15A tert-Butyl 4-{[2-(4-chlorophenyl)imidazo [1,2-a]pyridin-3-yl]methyl}piperazine-1-carboxylate

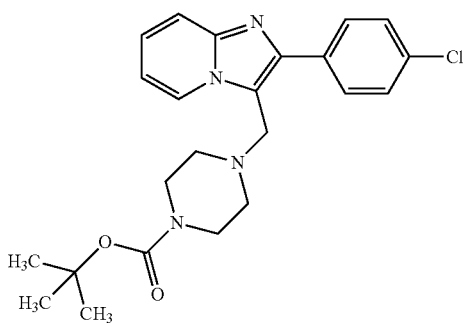 [SMILES: CC(C)(C)OC(=O)N1CCN(Cc2c(-c3ccc(Cl)cc3)nc3ccccn23)CC1]

Under argon and at room temperature, 1 g (3.90 mmol) of 2-(4-chlorophenyl)imidazo[1,2-a]pyridine-3-carbaldehyde was dissolved in 20 ml of THF, and 1.45 g (7.79 mmol) of tert-butyl piperazine-1-carboxylate and 0.45 ml (7.79 mmol) of acetic acid were added. Subsequently, 2.48 g of sodium triacetoxyborohydride (11.69 mmol) was added in a little at a time, and the reaction mixture was stirred at room temperature overnight. After the reaction had ended, water was slowly and carefully added dropwise (evolution of gas), and ethyl acetate was then added. The organic phase was removed and the aqueous phase was extracted twice with ethyl acetate. The combined organic phases were dried over magnesium sulphate, filtered and concentrated to dryness under reduced pressure on a rotary evaporator. The resulting residue was applied to silica gel and purified by column chromatography on silica gel (mobile phase: cyclohexane/ethyl acetate 2:1). This gave 1.27 g (2.97 mmol, 76% of theory) of the target compound.

$^1$H-NMR (400 MHz, DMSO-$d_6$, δ/ppm): 1.38 (s, 9H), 2.31-2.44 (m, 4H), 3.22-3.32 (m, 4H, partially hidden by water signal), 3.99 (s, 2H), 6.98 (t, 1H), 7.31 (t, 1H), 7.53 (d, 2H), 7.61 (d, 1H), 7.92 (d, 2H), 8.56 (d, 1H).

LC-MS (Method 1): $R_t$=0.85 min; m/z=427/429 (M+H)$^+$.

Analogously to Example 15A, the following compounds were prepared from the starting materials stated in each case:

| Example | Name/Structure/Starting materials | Analytical data |
|---|---|---|
| 16A | tert-butyl 4-{[2-(4-bromophenyl)imidazo[1,2-a]pyridin-3-yl]methyl}piperazine-1-carboxylate<br><br>from 2-(4-bromophenyl)imidazo[1,2-a]pyridine-3-carbaldehyde and tert-butyl piperazine-1-carboxylate | $^1$H-NMR (400 MHz, DMSO-$d_6$, δ/ppm): 1.38 (s, 9H), 2.31-2.44 (m, 4H), 3.21-3.32 (m, 4H, partially hidden by $H_2O$ signal), 3.99 (s, 2H), 6.98 (t, 1H), 7.32 (t, 1H), 7.61 (d, 1H), 7.67 (d, 2H), 7.86 (d, 2H), 8.57 (d, 1H).<br>LC-MS (Method 1): $R_t$ = 0.87 min; m/z = 471/473 (M + H)$^+$. |
| 17A | tert-butyl 4-{[2-(4-fluorophenyl)imidazo[1,2-a]pyridin-3-yl]methyl}piperazine-1-carboxylate<br><br>from 2-(4-fluorophenyl)imidazo[1,2-a]pyridine-3-carbaldehyde and tert-butyl piperazine-1-carboxylate | $^1$H-NMR (400 MHz, DMSO-$d_6$, δ/ppm): 1.38 (s, 9H), 2.34-2.44 (m, 4H), 3.21-3.32 (m, 4H, partially hidden by $H_2O$ signal), 3.98 (s, 2H), 6.97 (t, 1H), 7.30 (t, 3H), 7.60 (d, 1H), 7.88-7.97 (m, 2H), 8.56 (d, 1H).<br>LC-MS (Method 1): $R_t$ = 0.80 min; m/z = 411 (M + H)$^+$. |

-continued

| Example | Name/Structure/Starting materials | Analytical data |
|---|---|---|
| 18A | tert-butyl 4-{[2-(4-isopropylphenyl)imidazo[1,2-a]pyridin-3-yl]methyl}piperazine-1-carboxylate<br><br>from 2-(4-isopropylphenyl)imidazo[1,2-a]pyridine-3-carbaldehyde and tert-butyl piperazine-1-carboxylate | $^1$H-NMR (400 MHz, DMSO-$d_6$, δ/ppm): 1.25 (d, 6H), 1.38 (s, 9H), 2.34-2.44 (m, 4H), 2.88-2.99 (m, 1H), 3.22-3.32 (m, 4H, partially hidden by H$_2$O signal), 4.00 (s, 2H), 6.95 (t, 1H), 7.29 (t, 1H), 7.34 (d, 2H), 7.59 (d, 1H), 7.81 (d, 2H), 8.54 (d, 1H).<br>LC-MS (Method 1):<br>$R_t$ = 0.87 min; m/z = 435 (M + H)$^+$. |
| 19A | tert-butyl 4-{[2-(4-methylphenyl)imidazo[1,2-a]pyridin-3-yl]methyl}piperazine-1-carboxylate<br><br>from 2-(4-methylphenyl)imidazo[1,2-a]pyridine-3-carbaldehyde and tert-butyl piperazine-1-carboxylate | $^1$H-NMR (400 MHz, DMSO-$d_6$, δ/ppm): 1.38 (s, 9H), 2.36 (br. s, 7H), 3.22-3.34 (m, 4H, partially hidden by H$_2$O signal), 3.99 (s, 2H), 6.95 (t, 1H), 7.23-7.32 (m, 3H), 7.58 (d, 1H), 7.75 (d, 2H), 8.53 (d, 1H).<br>LC-MS (Method 1):<br>$R_t$ = 0.80 min; m/z = 407 (M + H)$^+$. |
| 20A | tert-butyl 4-{[2-(4-cyanophenyl)imidazo[1,2-a]pyridin-3-yl]methyl}piperazine-1-carboxylate<br><br>from 4-(3-formyl]midazo[1,2-a]pyridin-2-yl)benzonitrile and tert-butyl piperazine-1-carboxylate | $^1$H-NMR (400 MHz, DMSO-$d_6$, δ/ppm): 1.38 (s, 9H), 2.35-2.44 (m, 4H), 3.23-3.35 (m, 4H, partially hidden by H$_2$O signal), 4.03 (s, 2H), 7.00 (t, 1H), 7.35 (t, 1H), 7.64 (d, 1H), 7.93 (d, 2H), 8.13 (d, 2H), 8.60 (d, 1H).<br>LC-MS (Method 2):<br>$R_t$ = 1.54 min; m/z = 418 (M + H)$^+$. |

| Example | Name/Structure/Starting materials | Analytical data |
|---|---|---|
| 21A | tert-butyl 4-{[2-(4-tert-butylphenyl)imidazo[1,2-a]pyridin-3-yl]methyl}piperazine-1-carboxylate<br><br>from 2-(4-tert-butylphenyl)imidazo[1,2-a]pyridine-3-carbaldehyde and tert-butyl piperazine-1-carboxylate | ¹H-NMR (400 MHz, DMSO-d₆, δ/ppm): 1.33 (s, 9H), 1.38 (s, 9H), 2.35-2.45 (m, 4H), 3.22-3.35 (m, 4H, hidden by H₂O signal), 4.00 (s, 2H), 6.95 (t, 1H), 7.24-7.32 (m, 1H), 7.50 (d, 2H), 7.59 (d, 1H), 7.83 (d, 2H), 8.54 (d, 1H).<br>LC-MS (Method 2):<br>$R_t$ = 1.72 min; m/z = 449 (M + H)⁺. |

Example 22A 2-(4-Chlorophenyl)-3-(piperazin-1-ylmethyl)imidazo[1,2-a]pyridine dihydrochloride

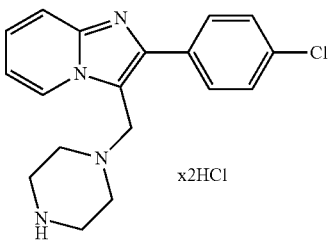 [SMILES: Clc1ccc(-c2nc3ccccn3c2CN2CCNCC2)cc1]

x2HCl

With stirring, 41.11 ml of a 4 M solution of hydrogen chloride in dioxane were added to 2.34 g (5.48 mmol) of tert-butyl 4-{[2-(4-chlorophenyl)imidazo[1,2-a]pyridin-3-yl]methyl}piperazine-1-carboxylate, and the mixture was stirred at room temperature for 3 hours. The solid obtained was then filtered off with suction, washed repeatedly with diethyl ether and dried under high vacuum at 40° C. This gave 2.48 g of the target product, which was used in the subsequent reactions without further purification.

LC/MS (Method 1): $R_t$=0.35 min; m/z=327/329 (M+H)⁺

Analogously to Example 22A, the following compounds were prepared from the starting material stated in each case:

| Example | Name/Structure/Starting material | Analytical data |
|---|---|---|
| 23A | 2-(4-bromophenyl)-3-(piperazin-1-ylmethyl)imidazo[1,2-a]pyridine dihydrochloride<br><br>×2HCl<br><br>from tert-butyl 4-{[2-(4-bromophenyl)imidazo[1,2-a]pyridin-3-yl]methyl}piperazine-1-carboxylate | LC-MS (Method 1):<br>$R_t$ = 0.38 min; m/z = 371/373 (M + H)⁺. |

-continued

| Example | Name/Structure/Starting material | Analytical data |
|---|---|---|
| 24A | 2-(4-fluorophenyl)-3-(piperazin-1-ylmethyl)imidazo[1,2-a]pyridine dihydrochloride 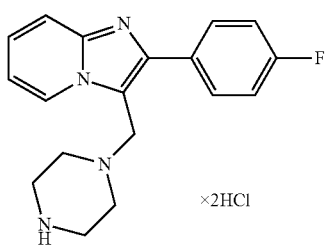 ×2HCl<br><br>from tert-butyl 4-{[2-(4-fluorophenyl)imidazo[1,2-a]pyridin-3-yl]methyl}piperazine-1-carboxylate | LC-MS (Method 1):<br>$R_t$ = 0.21 min; m/z = 311 (M + H)$^+$. |
| 25A | 2-(4-isopropylphenyl)-3-(piperazin-1-ylmethyl)imidazo[1,2-a]pyridine dihydrochloride 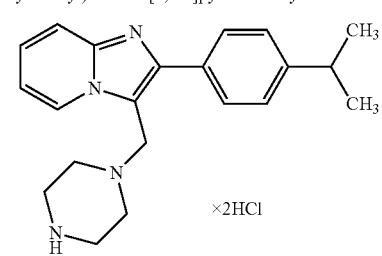 ×2HCl<br><br>from tert-butyl 4-{[2-(4-isopropylphenyl)imidazo[1,2-a]pyridin-3-yl]methyl}piperazine-1-carboxylate | LC-MS (Method 1):<br>$R_t$ = 0.46 min; m/z = 335 (M + H)$^+$. |
| 26A | 2-(4-methylphenyl)-3-(piperazin-1-ylmethyl)imidazo[1,2-a]pyridine dihydrochloride 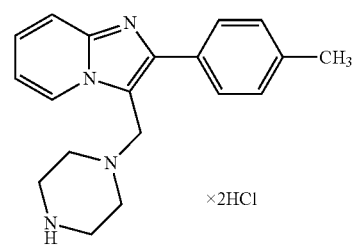 ×2HCl<br><br>from tert-butyl 4-{[2-(4-methylphenyl)imidazo[1,2-a]pyridin-3-yl]methyl}piperazine-1-carboxylate | LC-MS (Method 1):<br>$R_t$ = 0.23 min; m/z = 307 (M + H)$^+$. |
| 27A | 2-(4-cyanophenyl)-3-(piperazin-1-ylmethyl)imidazo[1,2-a]pyridine dihydrochloride 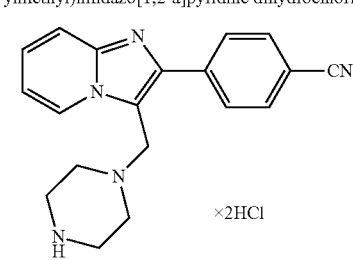 ×2HCl<br><br>from tert-butyl 4-{[2-(4-cyanophenyl)imidazo[1,2-a]pyridin-3-yl]methyl}piperazine-1-carboxylate | LC-MS (Method 1):<br>$R_t$ = 0.30 min; m/z = 318 (M + H)$^+$. |

| Example | Name/Structure/Starting material | Analytical data |
|---|---|---|
| 28A | 2-(4-tert-butylphenyl)-3-(piperazin-1-ylmethyl)imidazo[1,2-a]pyridine dihydrochloride 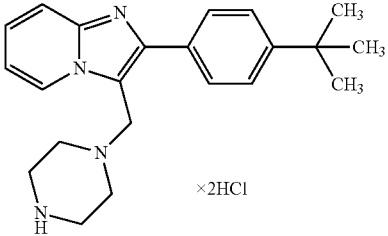 from tert-butyl 4-{[2-(4-tert.-butylphenyl)imidazo[1,2-a]pyridin-3-yl]methyl}piperazine-1-carboxylate | LC-MS (Method 4): $R_t$ = 1.54 min; m/z = 349 (M + H)$^+$. |

Example 29A

2-(4-Bromophenyl)-3-(piperazin-1-ylmethyl)imidazo[1,2-a]pyridine

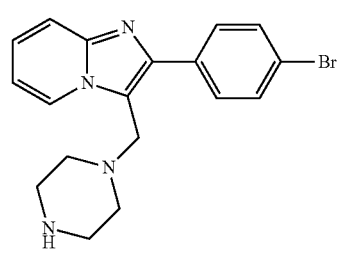 [SMILES: Brc1ccc(-c2nc3ccccn3c2CN2CCNCC2)cc1]

8.60 g (19.36 mmol) of 2-(4-bromophenyl)-3-(piperazin-1-ylmethyl)imidazo[1,2-a]pyridine dihydrochloride were dissolved in 83 ml of THF, 13.5 ml (97 mmol) of triethylamine were added and the mixture was stirred at room temperature for 2 hours. Water and ethyl acetate were then added to the reaction solution. The organic phase was separated off and the aqueous phase was extracted ten times with dichloromethane. The combined organic phases were dried over magnesium sulphate, filtered and concentrated to dryness under reduced pressure on a rotary evaporator. This gave 3.15 g (8.48 mmol, 44% of theory) of the target product, which was used in the subsequent reactions without further purification.

$^1$H-NMR (400 MHz, DMSO-d$_6$, δ/ppm): 2.29-2.43 (m, 4H), 2.61-2.75 (m, 4H), 3.95 (s, 2H), 6.98 (t, 1H), 7.31 (t, 1H), 7.60 (d, 1H), 7.67 (d, 2H), 7.85 (d, 2H), 8.54 (d, 1H).

LC-MS (Method 2): $R_t$=0.59 min; m/z=371/373 (M+H)$^+$.

Analogously to Example 29A, the following compound was prepared from the starting material stated:

| Example | Name/Structure/Starting materials | Analytical data |
|---|---|---|
| 30A | 2-(4-fluorophenyl)-3-(piperazin-1-ylmethyl)imidazo[1,2-a]pyridine 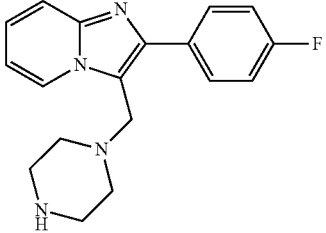 from 2-(4-fluorophenyl)-3-(piperazin-1-ylmethyl)imidazo[1,2-a]pyridine dihydrochloride | LC-MS (Method 3): $R_t$ = 1.89 min; m/z = 311 (M + H)$^+$. |

WORKING EXAMPLES

Example 1

(4-{[2-(4-Bromophenyl)imidazo[,2-a]pyridin-3-yl]methyl}piperazin-1-yl)(cyclopentyl)methanone

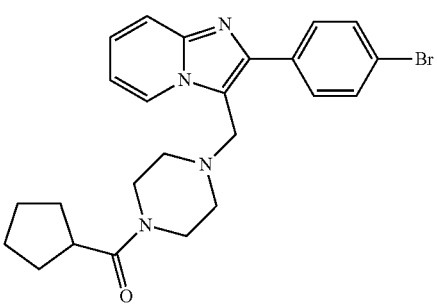 [SMILES: O=C(C1CCCC1)N1CCN(Cc2c(-c3ccc(Br)cc3)nc3ccccn23)CC1]

Synthesis Method 1

100 mg (0.27 mmol) of 2-(4-bromophenyl)-3-(piperazin-1-ylmethyl)imidazo[1,2-a]pyridine and 35 μl (0.32 mmol) of cyclopentanecarboxylic acid were dissolved in 2 ml of DMF, and 133 mg (0.35 mmol) of 2-(7-aza-1H-benzotriazol-1-yl)-1,1,3,3-tetramethyluronium hexafluorophosphate (HATU) and 94 µl (0.54 mmol) of N,N-diisopropylethylamine were added. The mixture was stirred at room temperature overnight. The reaction mixture was then separated directly into its components by preparative HPLC (Method 6). This gave 61 mg (0.13 mmol, 48% of theory) of the title compound.

LC-MS (Method 1): $R_t$=0.81 min; m/z=467/469 (M+H)$^+$.

$^1$H-NMR (400 MHz, DMSO-d$_6$): δ [ppm]=1.42-1.77 (m, 8H), 2.35-2.46 (m, 4H), 2.87-2.99 (m, 1H), 3.36-3.50 (m, 4H), 4.00 (s, 2H), 6.98 (t, 1H), 7.32 (t, 1H), 7.61 (d, 1H), 7.67 (d, 2H), 7.86 (d, 2H), 8.58 (d, 1H).

Example 2

(4-{[2-(4-Chlorophenyl)imidazo [1,2-a]pyridin-3-yl]methyl}piperazin-1-yl)(cyclopentyl)methanone

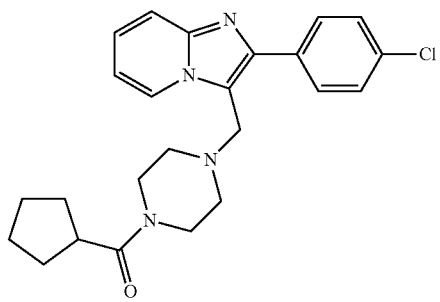 [SMILES: O=C(C1CCCC1)N1CCN(Cc2c(-c3ccc(Cl)cc3)nc3ccccn23)CC1]

Synthesis Method 2

150 mg (0.38 mmol) of 2-(4-chlorophenyl)-3-(piperazin-1-ylmethyl)imidazo[1,2-a]pyridine dihydrochloride were dissolved in 2 ml of DMF, and 261 µl (1.50 mmol) of N,N-diisopropylethylamine were added. The mixture was stirred at room temperature for 30 min. 47 mg (0.41 mmol) of cyclopentanecarboxylic acid and 214 mg (0.56 mmol) of 2-(7-aza-1H-benzotriazol-1-yl)-1,1,3,3-tetramethyluronium hexafluorophosphate (HATU) were then added, and the mixture was stirred further at room temperature overnight. The reaction mixture was then separated directly into its components by preparative HPLC (Method 6). This gave 110 mg (0.26 mmol, 69% of theory) of the title compound.

LC-MS (Method 1): $R_t$=0.80 min; m/z=423/425 (M+H)$^+$.

$^1$H-NMR (400 MHz, DMSO-d$_6$): δ [ppm]=1.42-1.78 (m, 8H), 2.34-2.46 (m, 4H), 2.88-2.99 (m, 1H), 3.37-3.50 (m, 4H), 4.01 (s, 2H), 6.98 (t, 1H), 7.32 (t, 1H), 7.53 (d, 2H), 7.61 (d, 1H), 7.92 (d, 2H), 8.58 (d, 1H).

Example 3

(4-{[2-(4-Chlorophenyl)imidazo [1,2-a]pyridin-3-yl]methyl}piperazin-1-yl)(6-methoxypyridin-2-yl)methanone

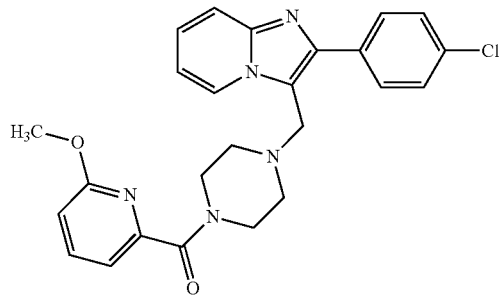

Synthesis Method 3

46 mg (0.30 mmol) of 6-methoxypyridine-2-carboxylic acid were dissolved in 1.5 ml of DMF, 124 mg (0.33 mmol) of 2-(7-aza-1H-benzotriazol-1-yl)-1,1,3,3-tetramethyluronium hexafluorophosphate (HATU) were added and the mixture was stirred at room temperature for 30 min. 100 mg (0.25 mmol) of 2-(4-chlorophenyl)-3-(piperazin-1-ylmethyl)imidazo[1,2-a]pyridine dihydrochloride and 0.13 ml (0.75 mmol) of N,N-diisopropylethylamine were then added, and the mixture was stirred further at room temperature overnight. The reaction mixture was then separated directly into its components by preparative HPLC (Method 6). This gave 81 mg (0.15 mmol, 60% of theory) of the title compound.

LC-MS (Method 1): $R_t$=0.74 min; m/z=462/464 (M+H)$^+$.

$^1$H-NMR (400 MHz, DMSO-d$_6$): δ [ppm]=2.42-2.48 (m, 2H), 2.48-2.59 (m, 2H, partially hidden by DMSO signal), 3.37-3.47 (m, 2H), 3.55-3.67 (m, 2H), 3.80 (s, 3H), 4.04 (s, 2H), 6.89 (d, 1H), 6.98 (t, 1H), 7.15 (d, 1H), 7.32 (t, 1H), 7.53 (d, 2H), 7.61 (d, 1H), 7.80 (t, 1H), 7.92 (d, 2H), 8.58 (d, 1H).

Example 4

(4-{[2-(4-Bromophenyl)imidazo [1,2-a]pyridin-3-yl]methyl}piperazin-1-yl)(2-fluorophenyl)methanone

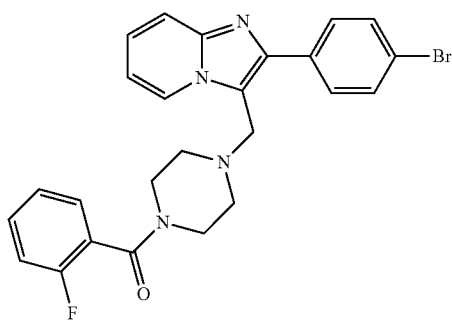 [SMILES: O=C(c1ccccc1F)N1CCN(Cc2c(-c3ccc(Br)cc3)nc3ccccn23)CC1]

Synthesis Method 4

1.77 g (3.98 mmol) of 2-(4-bromophenyl)-3-(piperazin-1-ylmethyl)imidazo[1,2-a]pyridine dihydrochloride were taken up in 30 ml of dichloromethane, 2.77 ml (15.90 mmol) of N,N-diisopropylethylamine were added and the mixture was stirred at room temperature for 30 min. After cooling of the reaction solution to 0° C., 0.52 ml (4.37 mmol) of 2-fluorobenzoyl chloride was added dropwise, and the mixture was then warmed to room temperature and stirred at this temperature overnight. After addition of water, the solution was shaken in a separating funnel and the phases were separated. The organic phase was dried over magnesium sulphate, filtered and concentrated to dryness under reduced pressure on a rotary evaporator. The resulting residue was applied to silica gel and purified by column chromatography on silica gel (Biotage; mobile phase: cyclohexane/ethyl acetate 4:1). This gave 1.42 g (2.88 mmol, 72% of theory) of the target compound.

LC-MS (Method 1): $R_t$=0.74 min; m/z=493/495 (M+H)$^+$.

$^1$H-NMR (400 MHz, DMSO-d$_6$): δ [ppm]=2.36-2.45 (m, 2H), 2.47-2.59 (m, 2H, hidden by DMSO signal), 3.13-3.23 (m, 2H), 3.56-3.68 (m, 2H), 4.03 (s, 2H), 6.98 (t, 1H), 7.23-7.41 (m, 4H), 7.44-7.53 (m, 1H), 7.60 (d, 1H), 7.67 (d, 2H), 7.85 (d, 2H), 8.58 (d, 1H).

Example 5

(4-{[2-(4-Bromophenyl)imidazo[1,2-a]pyridin-3-yl]methyl}piperazin-1-yl)(3-methoxyphenyl)methanone

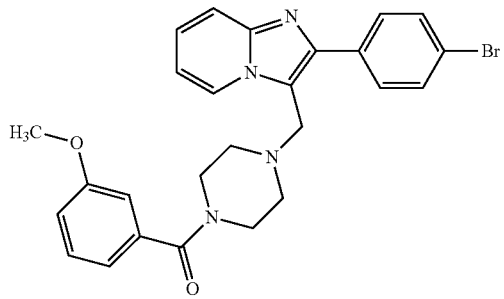

Synthesis Method 5

100 mg (0.27 mmol) of 2-(4-bromophenyl)-3-(piperazin-1-ylmethyl)imidazo[1,2-a]pyridine were taken up in 3 ml of dichloromethane, 56 µl (0.40 mmol) of triethylamine and 1.65 mg (0.01 mmol) of 4-N,N-dimethylaminopyridine were added and the mixture was then cooled to 0° C. 45 µl (0.30 mmol) of 3-methoxybenzoyl chloride were then added dropwise with stirring, and the mixture was then returned to room temperature by heating and stirred at this temperature overnight. After addition of water and dichloromethane, the resulting aqueous phase was extracted three more times with dichloromethane. The combined organic phases were dried over magnesium sulphate, filtered and concentrated to dryness under reduced pressure on a rotary evaporator. The residue obtained was dissolved in acetonitrile. After a short while, a solid precipitated from the solution, which solid was filtered off with suction, washed repeatedly with acetonitrile and then dried under high vacuum at 40° C. This gave 51 mg of the title compound. The mother liquor obtained was concentrated on a rotary evaporator, and the residue was separated into its components by preparative HPLC (Method 6). This gave a further 23 mg of the title compound. In total, 74 mg (0.14 mmol, 54% of theory) of the title compound were obtained.

LC-MS (Method 1): $R_t$=0.81 min; m/z=505/507 (M+H)$^+$.

$^1$H-NMR (400 MHz, DMSO-d$_6$): δ [ppm]=2.35-2.56 (m, 4H, partially hidden by DMSO signal), 3.22-3.38 (m, 2H, partially hidden by water signal), 3.47-3.66 (m, 2H), 3.77 (s, 3H), 4.02 (s, 2H), 6.86-6.94 (m, 2H), 6.95-7.03 (m, 2H), 7.28-7.38 (m, 2H), 7.60 (d, 1H), 7.67 (d, 2H), 7.85 (d, 2H), 8.58 (d, 1H).

Example 6

(4-{[2-(4-Bromophenyl)imidazo[1,2-a]pyridin-3-yl]methyl}piperazin-1-yl)(2-chloro-5-fluorophenyl)methanone

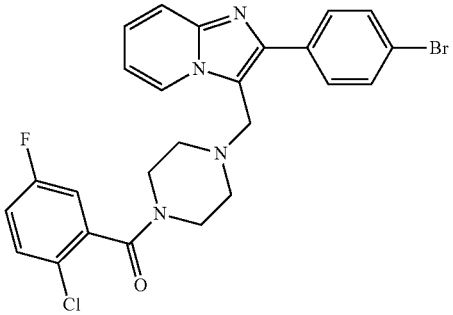 [SMILES: O=C(c1cc(F)ccc1Cl)N1CCN(Cc2c(-c3ccc(Br)cc3)nc3ccccn23)CC1]

Synthesis Method 6

47 mg (0.27 mmol) of 2-chloro-5-fluorobenzoic acid were taken up in 1 ml of dichloromethane, 100 mg (0.27 mmol) of 2-(4-bromophenyl)-3-(piperazin-1-ylmethyl)imidazo[1,2-a]pyridine were added and the mixture was stirred at room temperature for 30 min. 0.07 ml (0.81 mmol) of pyridine and 0.06 ml (0.43 mmol) of 1-chloro-1-dimethylamino-2-methyl-1-propene, dissolved in 3 ml of dichloromethane, were then added, and the mixture was stirred further at room temperature overnight. The reaction mixture was then concentrated and the residue was separated into its components by preparative HPLC (Method 6). This gave 76 mg (0.14 mmol, 52% of theory) of the title compound.

LC-MS (Method 1): $R_t$=0.86 min; m/z=527/529 (M+H)$^+$.

$^1$H-NMR (400 MHz, DMSO-d$_6$): δ [ppm]=2.38-2.46 (m, 2H), 2.46-2.57 (m, 2H, hidden by DMSO signal), 3.06-3.16 (m, 2H), 3.53-3.66 (m, 2H), 4.03 (s, 2H), 6.98 (t, 1H), 7.26-7.36 (m, 3H), 7.53-7.62 (m, 2H), 7.67 (d, 2H), 7.84 (d, 2H), 8.57 (d, 1H).

Example 7

(4-{[2-(4-Chlorophenyl)imidazo[1,2-a]pyridin-3-yl]methyl}piperazin-1-yl)(2-fluorophenyl)methanone

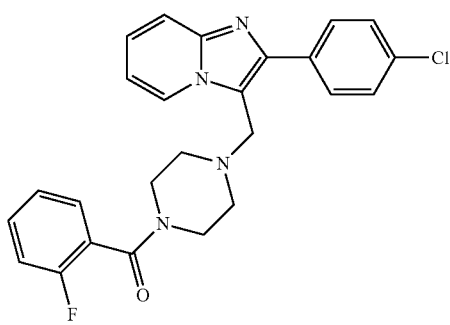 [SMILES: O=C(c1ccccc1F)N1CCN(Cc2c(-c3ccc(Cl)cc3)nc3ccccn23)CC1]

Synthesis Method 7

100 mg (0.25 mmol) of 2-(4-chlorophenyl)-3-(piperazin-1-ylmethyl)imidazo[1,2-a]pyridine dihydrochloride were dissolved in 1.5 ml of DMF, and 0.17 ml (1.00 mmol) of N,N-diisopropylethylamine were added. The mixture was stirred at room temperature for 30 min. 39 mg (0.28 mmol) of 2-fluorobenzoic acid and 143 mg (0.38 mmol) of 2-(7-aza-1H-benzotriazol-1-yl)-1,1,3,3-tetramethyluronium hexafluorophosphate (HATU) were then added, and the mixture was stirred further at room temperature overnight. The reaction mixture was then separated directly into its components by preparative HPLC (Method 6). This gave 76 mg (0.17 mmol, 68% of theory) of the title compound.

LC-MS (Method 1): $R_t$=0.77 min; m/z=449/451 (M+H)$^+$.

$^1$H-NMR (400 MHz, DMSO-d$_6$): δ [ppm]=2.35-2.44 (m, 2H), 2.44-2.58 (m, 2H, partially hidden by DMSO signal), 3.12-3.23 (m, 2H), 3.54-3.68 (m, 2H), 4.03 (s, 2H), 6.98 (t, 1H), 7.23-7.41 (m, 4H), 7.44-7.56 (m, 3H), 7.60 (d, 1H), 7.91 (d, 2H), 8.58 (d, 1H).

Example 8

(4-{[2-(4-Fluorophenyl)imidazo[1,2-a]pyridin-3-yl]methyl}piperazin-1-yl)(cyclohexyl)methanone

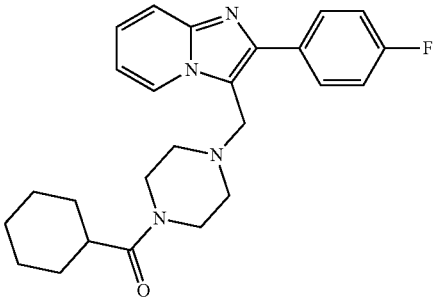 [SMILES: O=C(C1CCCCC1)N1CCN(Cc2c(-c3ccc(F)cc3)nc3ccccn23)CC1]

Synthesis Method 8

45 mg (0.35 mmol) of cyclohexanecarboxylic acid were dissolved in 1.5 ml of DMF, 184 mg (0.48 mmol) of 2-(7-aza-1H-benzotriazol-1-yl)-1,1,3,3-tetramethyluronium hexafluorophosphate (HATU) were added and the mixture was stirred at room temperature for 30 min. 100 mg (0.32 mmol) of 2-(4-fluorophenyl)-3-(piperazin-1-ylmethyl)imidazo[1,2-a]pyridine and 0.11 ml (0.64 mmol) of N,N-diisopropylethylamine were then added, and the mixture was stirred further at room temperature overnight. The reaction mixture was then separated directly into its components by preparative HPLC (Method 6). This gave 75 mg (0.17 mmol, 53% of theory) of the title compound.

LC-MS (Method 1): $R_t$=0.75 min; m/z=421 (M+H)$^+$.

$^1$H-NMR (400 MHz, DMSO-d$_6$): δ [ppm]=1.06-1.36 (m, 5H), 1.52-1.73 (m, 5H), 2.34-2.47 (m, 4H), 2.47-2.58 (m, 1H, hidden by DMSO signal), 3.36-3.48 (m, 4H), 3.99 (s, 2H), 6.97 (td, 1H), 7.26-7.35 (m, 3H), 7.60 (d, 1H), 7.89-7.96 (m, 2H), 8.57 (d, 1H).

The following compounds were also prepared according to the Synthesis methods 1-8 described above, using the starting materials stated in each case:

| Example | Name/Structure/Starting materials | Analytical data |
|---|---|---|
| 9 | (4-{[2-(4-bromophenyl)imidazo[1,2-a]pyridin-3-yl]methyl}piperazin-1-yl)(cyclohexyl)methanone<br>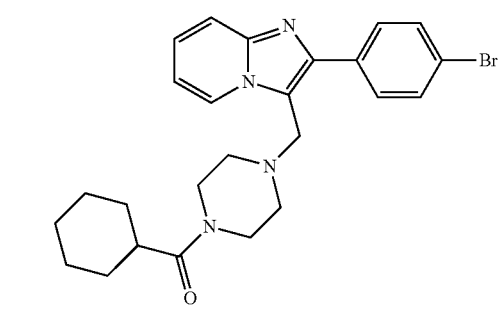<br>from 2-(4-bromophenyl)-3-(piperazin-1-ylmethyl)imidazo[1,2-a]pyridine and cyclohexanecarbonyl chloride (according to Synthesis method 5) | LC-MS (Method 1):<br>$R_t$ = 0.87 min; m/z = 481/483 (M + H)$^+$. |

-continued

| Example | Name/Structure/Starting materials | Analytical data |
| --- | --- | --- |
| 10 | (4-{[2-(4-bromophenyl)imidazo[1,2-a]pyridin-3-yl]methyl}piperazin-1-yl)(tetrahydrofuran-3-yl)methanone<br>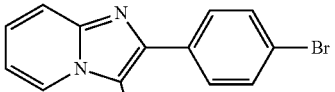<br>from 2-(4-bromophenyl)-3-(piperazin-1-ylmethyl)imidazo[1,2-a]pyridine and tetrahydrofuran-3-carbonyl chloride (according to Synthesis method 5) | $^1$H-NMR (400 MHz, DMSO-$d_6$, δ/ppm): 1.91-2.03 (m, 2H), 2.35-2.46 (m, 4H), 3.25-3.36 (m, 1H, hidden by H$_2$O signal), 3.39-3.50 (m, 4H), 3.60-3.72 (m, 3H), 3.83 (t, 1H), 4.01 (s, 2H), 6.98 (t, 1H), 7.32 (t, 1H), 7.61 (d, 1H), 7.67 (d, 2H), 7.86 (d, 2H), 8.58 (d, 1H).<br>LC-MS (Method 1):<br>R$_t$ = 0.68 min; m/z = 469/471 (M + H)$^+$. |
| 11 | (4-{[2-(4-bromophenyl)imidazo[1,2-a]pyridin-3-yl]methyl}piperazin-1-yl)(cyclobutyl)methanone<br>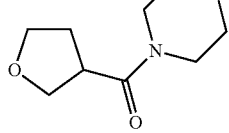<br>from 2-(4-bromophenyl)-3-(piperazin-1-ylmethyl)imidazo[1,2-a]pyridine and cyclobutanecarboxylic acid (according to Synthesis method 1) | $^1$H-NMR (400 MHz, DMSO-$d_6$, δ/ppm): 1.65-1.77 (m, 1H), 1.79-1.93 (m, 1H), 1.99-2.19 (m, 4H), 2.32-2.43 (m, 4H), 3.20-3.28 (m, 2H), 3.28-3.35 (m, 1H, hidden by H$_2$O signal), 3.35-3.44 (m, 2H), 4.00 (s, 2H), 6.98, (t, 1H), 7.32 (t, 1H), 7.60 (d, 1H), 7.67 (d, 2H), 7.86 (d, 2H), 8.57 (d, 1H).<br>LC-MS (Method 1):<br>R$_t$ = 0.76 min; m/z = 453/455 (M + H)$^+$. |
| 12 | (4-{[2-(4-bromophenyl)imidazo[1,2-a]pyridin-3-yl]methyl}piperazin-1-yl)(2-methoxyphenyl)methanone<br>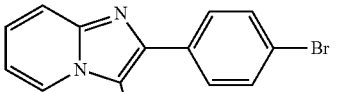<br>from 2-(4-bromophenyl)-3-(piperazin-1-ylmethyl)imidazo[1,2-a]pyridine and 2-methoxybenzoic acid (according to Synthesis method 1) | $^1$H-NMR (400 MHz, DMSO-$d_6$, δ/ppm): 2.25-2.44 (m, 2H), 2.44-2.57 (m, 2H), partially hidden by DMSO signal), 3.02-3.13 (m, 2H), 3.45-3.56 (m, 1H), 3.60-3.70 (m, 1H), 3.77 (s, 3H), 4.01, (s, 2H), 6.98 (t, 2H), 7.05 (d, 1H), 7.15 (dd, 1H), 7.31 (t, 1H), 7.37 (t, 1H), 7.60 (d, 1H), 7.67 (d, 2H), 7.85 (d, 2H), 8.57 (d, 1H).<br>LC-MS (Method 1):<br>R$_t$ = 0.77 min; m/z = 5.05/507 (M + H)$^+$. |

| Example | Name/Structure/Starting materials | Analytical data |
|---|---|---|
| 13 | (4-{[2-(4-bromophenyl)imidazo[1,2-a]pyridin-3-yl]methyl}piperazin-1-yl)(5-fluoro-2-methoxyphenyl)methanone<br><br>from 2-(4-bromophenyl)-3-(piperazin-1-ylmethyl)imidazo[1,2-a]pyridine and 5-fluoro-2-methoxybenzoic acid (according to Synthesis method 1) | $^1$H-NMR (400 MHz, DMSO-$d_6$, δ/ppm): 2.30-2.43 (m, 2H), 2.43-2.57 (m, 2H, partially hidden by DMSO signal), 3.09 (t, 2H), 3.46-3.56 (m, 1H), 3.57-3.67 (m, 1H), 3.76 (s, 3H), 4.02 (s, 2H), 6.98 (t, 1H), 7.02-7.10 (m, 2H), 7.21 (tt, 1H), 7.32 (t, 1H), 7.60 (d, 1H), 7.67 (d, 2H), 7.85 (d, 2H), 8.57 (d, 1H).<br>LC-MS (Method 1):<br>$R_t$ = 0.80 min; m/z = 523/525 (M + H)$^+$. |
| 14 | (4-{[2-(4-bromophenyl)imidazo[1,2-a]pyridin-3-yl]methyl}piperazin-1-yl)(2-methylphenyl)methanone<br><br>from 2-(4-bromophenyl)-3-(piperazin-1-ylmethyl)imidazo[1,2-a]pyridine and 2-methylbenzoic acid (according to Synthesis method 1) | $^1$H-NMR (400 MHz, DMSO-$d_6$, δ/ppm): 2.20 (s, 3H), 2.30-2.43 (m, 2H), 2.45-2.57 (m, 2H, hidden by DMSO signal), 3.09 (t, 2H), 3.56-3.68 (m, 2H), 4.01 (s, 2H), 6.97 (t, 1H), 7.13 (d, 1H), 7.18-7.34 (m, 4H), 7.60 (d, 1H), 7.67 (d, 2H), 7.85 (d, 2H), 8.57 (d, 1H).<br>LC-MS (Method 1):<br>$R_t$ = 0.82 min; m/z = 489/491 (M + H)$^+$. |
| 15 | (4-{[2-(4-bromophenyl)imidazo[1,2-a]pyridin-3-yl]methyl}piperazin-1-yl)(5-fluoro-2-methylphenyl)methanone<br><br>from 2-(4-bromophenyl)-3-(piperazin-1-ylmethyl)imidazo[1,2-a]pyridine and 5-fluoro-2-methylbenzoic acid (according to Synthesis method 1) | $^1$H-NMR (400 MHz, DMSO-$d_6$, δ/ppm): 2.17 (s, 3H), 2.30-2.57 (m, 4H, partially hidden by DMSO signal), 3.04-3.14 (m, 2H), 3.51-3.66 (m, 2H), 4.02 (s, 2H), 6.98 (t, 1H), 7.03 (dd, 1H), 7.13 (tt, 1H), 7.24-7.35 (m, 2H), 7.60 (d, 1H), 7.67 (d, 2H), 7.85 (d, 2H), 8.58 (d, 1H).<br>LC-MS (Method 1):<br>$R_t$ = 0.84 min; m/z = 507/509 (M + H)$^+$. |

-continued

| Example | Name/Structure/Starting materials | Analytical data |
|---|---|---|
| 16 | (2-chloro-5-fluorophenyl)(4-{[2-(4-chlorophenyl)imidazo[1,2-a]pyridin-3-yl]methyl}piperazin-1-yl)methanone<br>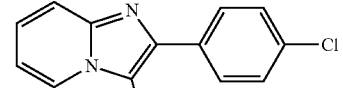<br>from 2-(4-chlorophenyl)-3-(piperazin-1-ylmethyl)imidazo[1,2-a]pyridine dihydrochloride and 2-chloro-5-fluorobenzoic acid (according to Synthesis method 7) | $^1$H-NMR (400 MHz, DMSO-$d_6$, δ/ppm): 2.38-2.46 (m, 2H), 2.47-2.57 (m, 2H, partially hidden by DMSO signal), 3.06-3.15 (m, 2H), 3.53-3.65 (m, 2H), 4.03 (s, 2H), 6.98 (t, 1H), 7.26-7.36 (m, 3H), 7.50-7.63 (m, 4H), 7.91 (d, 2H), 8.58 (d, 1H).<br>LC-MS (Method 1):<br>$R_t$ = 0.82 min; m/z = 483/485 (M + H)$^+$. |
| 17 | (4-{[2-(4-chlorophenyl)imidazo[1,2-a]pyridin-3-yl]methyl}piperazin-1-yl)(cyclohexyl)methanone<br>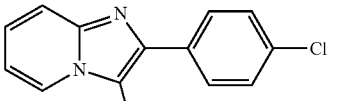<br>from 2-(4-chlorophenyl)-3-(piperazin-1-ylmethyl)imidazo[1,2-a]pyridine dihydrochloride and cyclohexanecarboxylic acid (according to Synthesis method 7) | $^1$H-NMR (400 MHz, DMSO-$d_6$, δ/ppm): 1.06-1.37 (m, 5H), 1.52-1.75 (m, 5H), 2.34-2.46 (m, 4H), 2.46-2.58 (m, 1H, hidden by DMSO signal), 3.35-3.48 (m, 4H), 4.00 (s, 2H), 6.98 (t, 1H), 7.32 (t, 1H), 7.53 (d, 2H), 7.61 (d, 1H), 7.92 (d, 2H), 8.57 (d, 1H).<br>LC-MS (Method 1):<br>$R_t$ = 0.84 min; m/z = 437/439 (M + H)$^+$. |
| 18 | ((4-{[2-(4-chlorophenyl)imidazo[1,2-a]pyridin-3-yl]methyl}piperazin-1-yl)(cyclobutyl)methanone<br>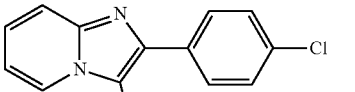<br>from 2-(4-chlorophenyl)-3-(piperazin-1-ylmethyl)imidazo[1,2-a]pyridine dihydrochloride and cyclobutanecarboxylic acid (according to Synthesis method 7) | $^1$H-NMR (400 MHz, DMSO-$d_6$, δ/ppm): 1.65-1.77 (m, 1H), 1.79-1.94 (m, 1H), 1.98-2.19 (m, 4H), 2.31-2.43 (m, 4H), 3.21-3.35 (m, 3H, partially hidden by H$_2$O signal), 3.36-3.44 (m, 2H), 4.00 (s, 2H), 6.98 (t, 1H), 7.32 (t, 1H), 7.53 (d, 2H), 7.61 (d, 1H), 7.92 (d, 2H), 8.57 (d, 1H).<br>LC-MS (Method 1):<br>$R_t$ = 0.74 min; m/z = 409/411 (M + H)$^+$. |

| Example | Name/Structure/Starting materials | Analytical data |
|---|---|---|
| 19 | (4-{[2-(4-chlorophenyl)imidazo[1,2-a]pyridin-3-yl]methyl}piperazin-1-yl)(3-methoxyphenyl)methanone<br>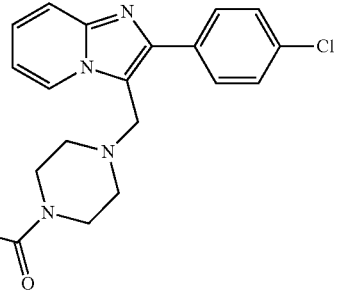<br>from 2-(4-chlorophenyl)-3-(piperazin-1-ylmethyl)imidazo[1,2-a]pyridine dihydrochloride and 3-methoxybenzoic acid (according to Synthesis method 7) | $^1$H-NMR (400 MHz, DMSO-$d_6$, δ/ppm): 2.34-2.59 (m, 4H, partially hidden by DMSO signal), 3.20-3.39 (m, 2H, partially hidden by H$_2$O signal), 3.45-3.67 (m, 2H), 3.77 (s, 3H), 4.03 (s, 2H), 6.85-6.94 (m, 2H), 6.95-7.03 (m, 2H), 7.26-7.38 (m, 2H), 7.53 (d, 2H), 7.60 (d, 1H), 7.92 (d, 2H), 8.58 (d, 1H).<br>LC-MS (Method 1):<br>$R_t$ = 0.77 min; m/z = 461/463 (M + H)$^+$. |
| 20 | (4-{[2-(4-chlorophenyl)imidazo[1,2-a]pyridin-3-yl]methyl}piperazin-1-yl)(2-methoxyphenyl)methanone<br>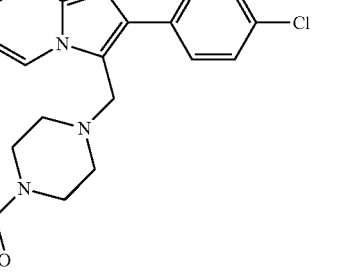<br>from 2-(4-chlorophenyl)-3-(piperazin-1-ylmethyl)imidazo[1,2-a]pyridine dihydrochloride and 2-methoxybenzoic acid (according to Synthesis method 7) | $^1$H-NMR (400 MHz, DMSO-$d_6$, δ/ppm): 2.26-2.57 (m, 4H, partially hidden by DMSO signal), 3.01-3.14 (m, 2H), 3.44-3.57 (m, 1H), 3.60-3.70 (m, 1H), 3.77 (s, 3H), 4.02 (s, 2H), 6.98 (t, 2H), 7.05 (d, 1H), 7.14 (dd, 1H), 7.28-7.41 (m, 2H), 7.53 (d, 2H), 7.60 (d, 1H), 7.91 (d, 2H), 8.57 (d, 1H).<br>LC-MS (Method 1):<br>$R_t$ = 0.75 min; m/z = 461/463 (M + H)$^+$. |
| 21 | (4-{[2-(4-chlorophenyl)imidazo[1,2-a]pyridin-3-yl]methyl}piperazin-1-yl)(5-fluoro-2-methoxyphenyl)methanone<br>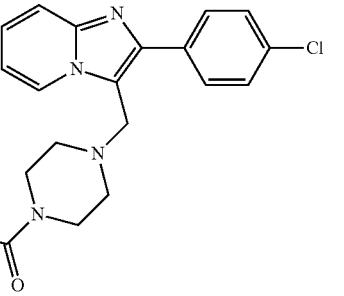<br>from 2-(4-chlorophenyl)-3-(piperazin-1-ylmethyl)imidazo[1,2-a]pyridine dihydrochloride and 2-methoxy-5-fluorobenzoic acid (according to Synthesis method 7) | $^1$H-NMR (400 MHz, DMSO-$d_6$, δ/ppm): 2.29-2.43 (m, 2H) 2.44-2.58 (m, 2H, partially hidden by DMSO signal), 3.04-3.14 (m, 2H), 3.46-3.56 (m, 1H), 3.57-3.68 (m, 1H), 3.76 (s, 3H), 4.02 (s, 2H), 6.98 (t, 1H), 7.02-7.10 (m, 2H), 7.17-7.25 (m, 1H), 7.28-7.36 (m, 1H), 7.53 (d, 2H), 7.60 (d, 1H), 7.91 (d, 2H), 8.57 (d, 1H).<br>LC-MS (Method 1):<br>$R_t$ = 0.78 min; m/z = 479/481 (M + H)$^+$. |

| Example | Name/Structure/Starting materials | Analytical data |
|---|---|---|
| 22 | (4-{[2-(4-chlorophenyl)imidazo[1,2-a]pyridin-3-yl]methyl}piperazin-1-yl)(2-methylphenyl)methanone<br><br>from 2-(4-chlorophenyl)-3-(piperazin-1-ylmethyl)imidazo[1,2-a]pyridine dihydrochloride and 2-methylbenzoic acid (according to Synthesis method 7) | $^1$H-NMR (400 MHz, DMSO-d$_6$, δ/ppm): 2.20 (s, 3H), 2.30-2.44 (m, 2H), 2.45-2.58 (m, 2H, hidden by DMSO signal), 3.03-3.14 (m, 2H), 3.55-3.69 (m, 2H), 4.02 (s, 2H), 6.98 (t, 1H), 7.13 (d, 1H), 7.18-7.35 (m, 4H), 7.53 (d, 2H), 7.60 (d, 1H), 7.91 (d, 2H), 8.58 (d, 1H).<br>LC-MS (Method 1):<br>R$_t$ = 0.80 min; m/z = 445/447 (M + H)$^+$. |
| 23 | (4-{[2-(4-chlorophenyl)imidazo[1,2-a]pyridin-3-yl]methyl}piperazin-1-yl)(5-fluoro-2-methylphenyl)methanone<br><br>from 2-(4-chlorophenyl)-3-(piperazin-1-ylmethyl)imidazo[1,2-a]pyridine dihydrochloride and 5-fluoro-2-methylbenzoic acid (according to Synthesis method 7) | $^1$H-NMR (400 MHz, DMSO-d$_6$, δ/ppm): 2.17 (s, 3H), 2.29-2.57 (m, 4H, partially hidden by DMSO signal), 3.04-3.16 (m, 2H), 3.53-3.67 (m, 2H), 4.02 (s, 2H), 6.98 (t, 1H), 7.03 (dd, 1H), 7.13 (tt, 1H), 7.25-7.35 (m, 2H), 7.53 (d, 2H), 7.60 (d, 1H), 7.91 (d, 2H), 8.58 (d, 1H).<br>LC-MS (Method 1):<br>R$_t$ = 0.82 min; m/z = 463/465 (M + H)$^+$. |
| 24 | (4-{[2-(4-chlorophenyl)imidazo[1,2-a]pyridin-3-yl]methyl}piperazin-1-yl)[3-(trifluoromethoxy)phenyl]methanone<br><br>from 2-(4-chlorophenyl)-3-(piperazin-1-ylmethyl)imidazo[1,2-a]pyridine dihydrochloride and 3-(trifluoromethoxy)benzoic acid (according to Synthesis method 3) | $^1$H-NMR (400 MHz, DMSO-d$_6$, δ/ppm): 2.37-2.58 (m, 4H, partially hidden by DMSO signal), 3.20-3.35 (m, 2H, partially hidden by H$_2$O signal), 3.51-3.66 (m, 2H), 4.03 (s, 2H), 6.98 (t, 1H), 7.32 (t, 1H), 7.37 (s, 1H), 7.41 (d, 1H), 7.45 (d, 1H), 7.53 (d, 2H), 7.55-7.63 (m, 2H), 7.91 (d, 2H), 8.57 (d, 1H).<br>LC-MS (Method 1):<br>R$_t$ = 0.87 min; m/z = 515/517 (M + H)$^+$. |

| Example | Name/Structure/Starting materials | Analytical data |
| --- | --- | --- |
| 25 | (4-{[2-(4-chlorophenyl)imidazo[1,2-a]pyridin-3-yl]methyl}piperazin-1-yl)[3-(trifluoromethyl)phenyl]methanone<br>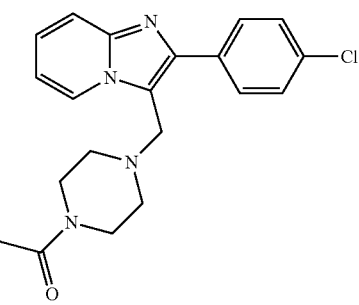<br>from 2-(4-chlorophenyl)-3-(piperazin-1-ylmethyl)imidazo[1,2-a]pyridine dihydrochloride and 3-(trifluoromethyl)benzoic acid (according to Synthesis method 3) | $^1$H-NMR (400 MHz, DMSO-$d_6$, δ/ppm): 2.37-2.60 (m, 4H, partially hidden by DMSO signal), 3.20-3.37 (m, 2H, partially hidden by H$_2$O signal), 3.51-3.69 (m, 2H), 4.03 (s, 2H), 6.98 (t, 1H), 7.32 (t, 1H), 7.53 (d, 2H), 7.61 (d, 1H), 7.64-7.74 (m, 3H), 7.78-7.85 (m, 1H), 7.91 (d, 2H), 8.58 (d, 1H).<br>LC-MS (Method 1):<br>R$_t$ = 0.87 min; m/z = 499/501 (M + H)$^+$. |
| 26 | ((4-{[2-(4-chlorophenyl)imidazo[1,2-a]pyridin-3-yl]methyl}piperazin-1-yl)(pyridin-2-yl)methanone<br>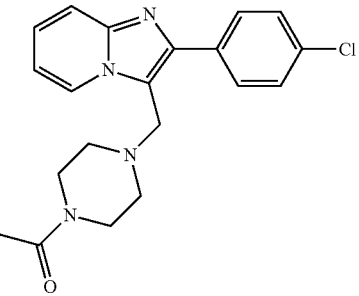<br>from 2-(4-chlorophenyl)-3-(piperazin-1-ylmethyl)imidazo[1,2-a]pyridine dihydrochloride and pyridine-2-carboxylic acid (according to Synthesis method 3) | $^1$H-NMR (400 MHz, DMSO-$d_6$, δ/ppm): 2.37-2.46 (m, 2H), 2.47-2.59 (m, 2H, hidden by DMSO signal), 3.33-3.40 (m, 2H), 3.56-3.67 (m, 2H), 4.04 (s, 2H), 6.99 (t, 1H), 7.27-7.36 (m, 1H), 7.42-7.49 (m, 1H), 7.50-7.57 (m, 3H), 7.61 (d, 1H), 7.86-7.96 (m, 3H), 8.53-8.62 (m, 2H).<br>LC-MS (Method 1):<br>R$_t$ = 0.63 min; m/z = 432/434 (M + H)$^+$. |
| 27 | (4-{[2-(4-chlorophenyl)imidazo[1,2-a]pyridin-3-yl]methyl}piperazin-1-yl)(2-fluoro-5-methoxyphenyl)methanone<br>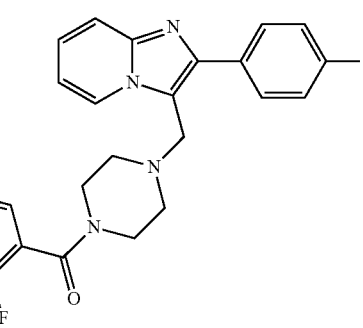<br>from 2-(4-chlorophenyl)-3-(piperazin-1-ylmethyl)imidazo[1,2-a]pyridine dihydrochloride and 2-fluoro-5-methoxybenzoic acid (according to Synthesis method 3) | $^1$H-NMR (400 MHz, DMSO-$d_6$, δ/ppm): 2.36-2.46 (m, 2H), 2.47-2.58 (m, 2H, hidden by DMSO signal), 3.15-3.23 (m, 2H), 3.54-3.66 (m, 2H), 3.75 (s, 3H), 4.03 (s, 2H), 6.88 (t, 1H), 6.95-7.04 (m, 2H), 7.20 (t, 1H), 7.28-7.35 (m, 1H), 7.53 (d, 2H), 7.60 (d, 1H), 7.91 (d, 2H), 8.58 (d, 1H).<br>LC-MS (Method 2):<br>R$_t$ = 1.49 min; m/z = 479/481 (M + H)$^+$. |

| Example | Name/Structure/Starting materials | Analytical data |
|---|---|---|
| 28 | (4-{[2-(4-chlorophenyl)imidazo[1,2-a]pyridin-3-yl]methyl}piperazin-1-yl)(2-ethoxyphenyl)methanone<br><br>from 2-(4-chlorophenyl)-3-(piperazin-1-ylmethyl)imidazo[1,2-a]pyridine dihydrochloride and 2-ethoxybenzoic acid (according to Synthesis method 3) | $^1$H-NMR (400 MHz, DMSO-$d_6$, δ/ppm): 1.27 (t, 3H), 2.25-2.41 (m, 2H), 2.42-2.56 (m, 2H, hidden by DMSO signal), 3.00-3.13 (m, 2H), 3.51-3.65 (m, 2H), 3.94-4.10 (m, 4H), 6.91-7.06 (m, 3H), 7.13 (dd, 1H), 7.27-7.38 (m, 2H), 7.53 (d, 2H), 7.60 (d, 1H), 7.89 (d, 2H), 8.55 (d, 1H).<br>LC-MS (Method 2):<br>$R_t$ = 1.50 min; m/z = 475/477 (M + H)$^+$. |
| 29 | (2-chloro-5-methoxyphenyl)(4-{[2-(4-chlorophenyl)imidazo[1,2-a]pyridin-3-yl]methyl}piperazin-1-yl)methanone<br><br>from 2-(4-chlorophenyl)-3-(piperazin-1-ylmethyl)imidazo[1,2-a]pyridine dihydrochloride and 2-chloro-5-methoxybenzoic acid (according to Synthesis method 3) | $^1$H-NMR (400 MHz, DMSO-$d_6$, δ/ppm): 2.43 (t, 2H), 2.47-2.57 (m, 2H, hidden by DMSO signal), 3.11 (t, 2H), 3.52-3.64 (m, 2H), 3.76 (s, 3H), 4.03 (s, 2H), 6.90 (d, 1H), 6.95-7.02 (m, 2H), 7.27-7.35 (m, 1H), 7.40 (d, 1H), 7.53 (d, 2H), 7.60 (d, 1H), 7.91 (d, 2H), 8.58 (d, 1H).<br>LC-MS (Method 2):<br>$R_t$ = 1.56 min; m/z = 495/496/497 (M + H)$^+$. |
| 30 | (4-{[2-(4-chlorophenyl)imidazo[1,2-a]pyridin-3-yl]methyl}piperazin-1-yl)(tetrahydro-2H-pyran-2-yl)methanone<br><br>from 2-(4-chlorophenyl)-3-(piperazin-1-ylmethyl)imidazo[1,2-a]pyridine dihydrochloride and tetrahydro-2H-pyran-2-carboxylic acid (according to Synthesis method 3) | $^1$H-NMR (400 MHz, DMSO-$d_6$, δ/ppm): 1.37-1.64 (m, 5H), 1.74-1.84 (m, 1H), 2.34-2.45 (m, 4H), 3.34-3.50 (m, 5H), 3.82 (d, 1H), 4.01 (s, 2H), 4.08 (dd, 1H), 6.98 (td, 1H), 7.32 (ddd, 1H), 7.53 (d, 2H), 7.61 (d, 1H), 7.93 (d, 2H), 8.57 (d, 1H).<br>LC-MS (Method 2):<br>$R_t$ = 1.29 min; m/z = 439/441 (M + H)$^+$. |

| Example | Name/Structure/Starting materials | Analytical data |
|---|---|---|
| 31 | (4-{[2-(4-chlorophenyl)imidazo[1,2-a]pyridin-3-yl]methyl}piperazin-1-yl)(3-isopropoxyphenyl)methanone<br><br>from 2-(4-chlorophenyl)-3-(piperazin-1-ylmethyl)imidazo[1,2-a]pyridine dihydrochloride and 3-isopropoxybenzoic acid (according to Synthesis method 3) | $^1$H-NMR (400 MHz, DMSO-$d_6$, δ/ppm): 1.25 (d, 6H), 2.36-2.58 (m, 4H, partially hidden by DMSO signal), 3.21-3.38 (m, 2H, partially hidden by H$_2$O signal), 3.47-3.66 (m, 2H), 4.03 (s, 2H), 4.57-4.68 (m, 1H), 6.82-6.90 (m, 2H), 6.93-7.01 (m, 2H), 7.31 (t, 2H), 7.53 (d, 2H), 7.60 (d, 1H), 7.92 (d, 2H), 8.57 (d, 1H).<br>LC-MS (Method 2):<br>$R_t$ = 1.56 min; m/z = 489/491 (M + H)$^+$. |
| 32 | 2-[(4-{[2-(4-chlorophenyl)imidazo[1,2-a]pyridin-3-yl]methyl}piperazin-1-yl)carbonyl]benzonitrile<br><br>from 2-(4-chlorophenyl)-3-(piperazin-1-ylmethyl)imidazo[1,2-a]pyridine dihydrochloride and 2-cyanobenzoic acid (according to Synthesis method 3) | $^1$H-NMR (400 MHz, DMSO-$d_6$, δ/ppm): 2.42 (br. s, 2H), 2.47-2.58 (m, 2H, hidden by DMSO signal), 3.17 (br. s, 2H), 3.64 (br. s, 2H), 4.04 (s, 2H), 6.98 (td, 1H), 7.32 (t, 1H), 7.53 (d, 3H), 7.57-7.66 (m, 2H), 7.77 (t, 1H), 7.87-7.96 (m, 3H), 8.58 (d, 1H).<br>LC-MS (Method 2):<br>$R_t$ = 1.32 min; m/z = 456/458 (M + H)$^+$. |
| 33 | (4-{[2-(4-chlorophenyl)imidazo[1,2-a]pyridin-3-yl]methyl}piperazin-1-yl)(3-isopropylphenyl)methanone<br><br>from 2-(4-chlorophenyl)-3-(piperazin-1-ylmethyl)imidazo[1,2-a]pyridine dihydrochloride and 3-isopropylbenzoic acid (according to Synthesis method 3) | LC-MS (Method 2):<br>$R_t$ = 1.72 min; m/z = 473/475 (M + H)$^+$. |

-continued

| Example | Name/Structure/Starting materials | Analytical data |
|---|---|---|
| 34 | (4-{[2-(4-chlorophenyl)imidazo[1,2-a]pyridin-3-yl]methyl}piperazin-1-yl)(2-isopropylphenyl)methanone<br><br>from 2-(4-chlorophenyl)-3-(piperazin-1-ylmethyl)imidazo[1,2-a]pyridine dihydrochloride and 2-isopropylbenzoic acid (according to Synthesis method 3) | $^1$H-NMR (400 MHz, DMSO-d$_6$, δ/ppm): 1.15 (t, 6H), 2.25-2.35 (m, 1H), 2.35-2.58 (m, 3H, partially hidden by DMSO signal), 2.79-2.90 (m, 1H), 3.00-3.17 (m, 2H), 4.02 (s, 2H), 6.98 (t, 1H), 7.08 (d, 1H), 7.22 (t, 1H), 7.27-7.41 (m, 3H), 7.53 (d, 2H), 7.60 (d, 1H), 7.90 (d, 2H), 8.57 (d, 1H).<br>LC-MS (Method 1):<br>R$_t$ = 0.93 min; m/z = 473/475 (M + H)$^+$. |
| 35 | (4-{[2-(4-chlorophenyl)imidazo[1,2-a]pyridin-3-yl]methyl}piperazin-1-yl)(tetrahydrofuran-2-yl)methanone<br><br>from 2-(4-chlorophenyl)-3-(piperazin-1-ylmethyl)imidazo[1,2-a]pyridine dihydrochloride and tetrahydrofuran-2-carboxylic acid (according to Synthesis method 3) | $^1$H-NMR (400 MHz, DMSO-d$_6$, δ/ppm): 1.71-1.88 (m, 2H), 1.90-2.05 (m, 2H), 2.33-2.47 (m, 4H), 3.27-3.54 (m, 4H, partially hidden by H$_2$O signal), 3.66-3.80 (m, 2H), 4.01 (s, 2H), 4.62 (t, 1H), 6.98 (t, 1H), 7.32 (t, 1H), 7.53 (d, 2H), 7.61 (d, 1H), 7.92 (d, 2H), 8.58 (d, 1H).<br>LC-MS (Method 1):<br>R$_t$ = 0.64 min; m/z = 425/427 (M + H)$^+$. |
| 36 | (3-chlorophenyl)(4-{[2-(4-chlorophenyl)imidazo[1,2-a]pyridin-3-yl]methyl}piperazin-1-yl)methanone<br><br>from 2-(4-chlorophenyl)-3-(piperazin-1-ylmethyl)imidazo[1,2-a]pyridine dihydrochloride and 3-chlorobenzoic acid (according to Synthesis method 3) | $^1$H-NMR (400 MHz, DMSO-d$_6$, δ/ppm): 2.35-2.58 (m, 4H, partially hidden by DMSO signal), 3.20-3.36 (m, 2H, partially hidden by H$_2$O signal), 3.47-3.67 (m, 2H), 4.03 (s, 2H), 6.98 (t, 1H), 7.24-7.36 (m, 2H), 7.40-7.56 (m, 5H), 7.60 (d, 1H), 7.91 (d, 2H), 8.57 (d, 1H).<br>LC-MS (Method 2):<br>R$_t$ = 1.56 min; m/z = 465/466/467 (M + H)$^+$. |

| Example | Name/Structure/Starting materials | Analytical data |
|---|---|---|
| 37 | (2-chlorophenyl)(4-{[2-(4-chlorophenyl)imidazo[1,2-a]pyridin-3-yl]methyl}piperazin-1-yl)methanone<br />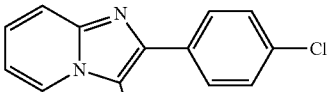<br />from 2-(4-chlorophenyl)-3-(piperazin-1-ylmethyl)imidazo[1,2-a]pyridine dihydrochloride and 2-chlorobenzoic acid (according to Synthesis method 3) | $^1$H-NMR (400 MHz, DMSO-d$_6$, δ/ppm): 2.31-2.58 (m, 4H, partially hidden by DMSO signal), 3.09 (t, 2H), 3.53-3.68 (m, 2H), 4.02 (s, 2H), 6.98 (td, 1H), 7.26-7.36 (m, 2H), 7.37-7.46 (m, 2H), 7.47-7.56 (m, 3H), 7.60 (d, 1H), 7.91 (d, 2H), 8.58 (d, 1H).<br />LC-MS (Method 2):<br />R$_t$ = 1.46 min; m/z = 465/466/467 (M + H)$^+$. |
| 38 | (4-{[2-(4-chlorophenyl)imidazo[1,2-a]pyridin-3-yl]methyl}piperazin-1-yl)[6-(2,2,2-trifluoroethoxy)pyridin-2-yl]methanone<br />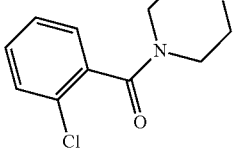<br />from 2-(4-chlorophenyl)-3-(piperazin-1-ylmethyl)imidazo[1,2-a]pyridine dihydrochloride and 6-(2,2,2-trifluoroethoxy)pyridine-2-carboxylic acid (according to Synthesis method 3) | $^1$H-NMR (400 MHz, DMSO-d$_6$, δ/ppm): 2.45 (br. s, 2H), 2.56 (br. s, 2H, partially hidden by DMSO signal), 3.41 (br. s, 2H), 3.62 (br. s, 2H), 4.04 (s, 2H), 4.95 (q, 2H), 6.98 (t, 1H), 7.07 (d, 1H), 7.26-7.36 (m, 2H), 7.53 (d, 2H), 7.61 (d, 1H), 7.87-7.95 (m, 3H), 8.59 (d, 1H).<br />LC-MS (Method 2):<br />R$_t$ = 1.60 min; m/z = 530/532 (M + H)$^+$. |
| 39 | (4-{[2-(4-chlorophenyl)imidazo[1,2-a]pyridin-3-yl]methyl}piperazin-1-yl)(6-isopropoxypyridin-2-yl)methanone<br />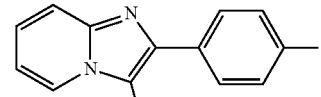<br />from 2-(4-chlorophenyl)-3-(piperazin-1-ylmethyl)imidazo[1,2-a]pyridine dihydrochloride and 6-isopropoxypyridine-2-carboxylic acid (according to Synthesis method 3) | $^1$H-NMR (400 MHz, DMSO-d$_6$, δ/ppm): 1.21 (d, 6H), 2.41 (br. s, 2H), 2.57 (br. s, 2H, partially hidden by DMSO signal), 3.39 (br. s, 2H), 3.61 (br. s, 2H), 4.05 (s, 2H), 5.09-5.20 (m, 1H), 6.79 (d, 1H), 6.98 (td, 1H), 7.09 (dd, 1H), 7.28-7.35 (m, 1H), 7.53 (d, 2H), 7.61 (d, 1H), 7.76 (dd, 1H), 7.93 (d, 2H), 8.58 (d, 1H).<br />LC-MS (Method 2):<br />R$_t$ = 1.57 min; m/z = 490/492 (M + H)$^+$. |

| Example | Name/Structure/Starting materials | Analytical data |
|---|---|---|
| 40 | (4-{[2-(4-chlorophenyl)imidazo[1,2-a]pyridin-3-yl]methyl}piperazin-1-yl)(6-methoxy-4-methylpyridin-2-yl)methanone<br><br>from 2-(4-chlorophenyl)-3-(piperazin-1-ylmethyl)imidazo[1,2-a]pyridine dihydrochloride and 6-methoxy-4-methylpyridine-2-carboxylic acid (according to Synthesis method 3) | $^1$H-NMR (400 MHz, DMSO-$d_6$, δ/ppm): 2.29 (s, 3H), 2.45 (br. s, 2H), 2.48-2.58 (m, 2H, hidden by DMSO signal), 3.41 (br. s, 2H), 3.59 (br. s, 2H), 3.78 (s, 3H), 4.04 (s, 2H), 6.71 (s, 1H), 6.94-7.01 (m, 2H), 7.27-7.35 (m, 1H), 7.53 (d, 2H), 7.61 (d, 1H), 7.92 (d, 2H), 8.58 (d, 1H).<br>LC-MS (Method 2):<br>$R_t$ = 1.44 min; m/z = 476 (M + H)$^+$. |
| 41 | (4-{[2-(4-chlorophenyl)imidazo[1,2-a]pyridin-3-yl]methyl}piperazin-1-yl)[6-(cyclobutyloxy)pyridin-2-yl]methanone<br><br>from 2-(4-chlorophenyl)-3-(piperazin-1-ylmethyl)imidazo[1,2-a]pyridine dihydrochloride and 6-(cyclobutyloxy)pyridine-2-carboxylic acid (according to Synthesis method 3) | $^1$H-NMR (400 MHz, DMSO-$d_6$, δ/ppm): 1.50-1.65 (m, 1H), 1.69-1.82 (m, 1H), 1.95-2.08 (m, 2H), 2.27-2.38 (m, 2H), 2.38-2.46 (m, 2H), 2.46-2.62 (m, 2H, hidden by DMSO signal), 3.40 (br. s, 2H), 3.61 (br. s, 2H), 4.05 (s, 2H), 4.98-5.09 (m, 1H), 6.84 (d, 1H), 6.98 (t, 1H), 7.13 (d, 1H), 7.32 (t, 1H), 7.53 (d, 2H), 7.61 (d, 1H), 7.78 (t, 1H), 7.93 (d, 2H), 8.58 (d, 1H).<br>LC-MS (Method 2):<br>$R_t$ = 1.64 min; m/z = 502/504 (M + H)$^+$. |
| 42 | (3-bromo-6-methoxypyridin-2-yl)(4-{[2-(4-chlorophenyl)imidazo[1,2-a]pyridin-3-yl]methyl}piperazin-1-yl)methanone<br><br>from 2-(4-chlorophenyl)-3-(piperazin-1-ylmethyl)imidazo[1,2-a]pyridine dihydrochloride and 3-bromo-6-methoxypyridine-2-carboxylic acid (according to Synthesis method 3) | $^1$H-NMR (400 MHz, DMSO-$d_6$, δ/ppm): 2.44 (t, 2H), 2.47-2.58 (m, 2H, hidden by DMSO signal), 3.10 (t, 2H), 3.60 (br. s, 2H), 3.80 (s, 3H), 4.04 (s, 2H), 6.84 (d, 1H), 6.98 (t, 1H), 7.27-7.35 (m, 1H), 7.53 (d, 2H), 7.60 (d, 1H), 7.91 (d, 2H), 7.97 (d, 1H), 8.59 (d, 1H).<br>LC-MS (Method 2):<br>$R_t$ = 1.47 min; m/z = 540/542 (M + H)$^+$. |

| Example | Name/Structure/Starting materials | Analytical data |
|---|---|---|
| 43 | (3-chloro-6-methoxypyridin-2-yl)(4-{[2-(4-chlorophenyl)imidazo[1,2-a]pyridin-3-yl]methyl}piperazin-1-yl)methanone<br><br>from 2-(4-chlorophenyl)-3-(piperazin-1-ylmethyl)imidazo[1,2-a]pyridine dihydrochloride and 3-chloro-6-methoxypyridine-2-carboxylic acid (according to Synthesis method 3) | $^1$H-NMR (400 MHz, DMSO-d$_6$, δ/ppm): 2.43 (t, 2H), 2.46-2.57 (m, 2H, hidden by DMSO signal), 3.12 (t, 2H), 3.61 (br. s, 2H), 3.81 (s, 3H), 4.04 (s, 2H), 6.92 (d, 1H), 6.98 (t, 1H), 7.28-7.35 (m, 1H), 7.53 (d, 2H), 7.61 (d, 1H), 7.87 (d, 1H), 7.92 (d, 2H), 8.59 (d, 1H).<br>LC-MS (Method 2):<br>R$_t$ = 1.44 min; m/z = 496/497/498 (M + H)$^+$. |
| 44 | (4-{[2-(4-chlorophenyl)imidazo[1,2-a]pyridin-3-yl]methyl}piperazin-1-yl)[6-(difluoromethoxy)pyridin-2-yl]methanone<br><br>from 2-(4-chlorophenyl)-3-(piperazin-1-ylmethyl)imidazo[1,2-a]pyridine dihydrochloride and 6-(difluoromethoxy)pyridine-2-carboxylic acid (according to Synthesis method 3) | $^1$H-NMR (400 MHz, DMSO-d$_6$, δ/ppm): 2.43 (t, 2H), 2.46-2.57 (m, 2H, hidden by DMSO signal), 3.12 (t, 2H), 3.61 (br. s, 2H), 3.81 (s, 3H), 4.04 (s, 2H), 6.92 (d, 1H), 6.98 (t, 1H), 7.28-7.35 (m, 1H), 7.53 (d, 2H), 7.61 (d, 1H), 7.87 (d, 1H), 7.92 (d, 2H), 8.59 (d, 1H).<br>LC-MS (Method 2):<br>R$_t$ = 1.45 min; m/z = 498/500 (M + H)$^+$. |
| 45 | (4-{[2-(4-chlorophenyl)imidazo[1,2-a]pyridin-3-yl]methyl}piperazin-1-yl)(6-ethoxypyridin-2-yl)methanone<br><br>from 2-(4-chlorophenyl)-3-(piperazin-1-ylmethyl)imidazo[1,2-a]pyridine dihydrochloride and 6-ethoxypyridine-2-carboxylic acid (according to Synthesis method 3) | $^1$H-NMR (400 MHz, DMSO-d$_6$, δ/ppm): 1.27 (t, 3H), 2.44 (br. s, 2H), 2.47-2.59 (m, 2H, hidden by DMSO signal), 3.40 (br. s, 2H), 3.61 (br. s, 2H), 4.04 (s, 2H), 4.24 (q, 2H), 6.85 (d, 1H), 6.98 (t, 1H), 7.13 (d, 1H), 7.32 (t, 1H), 7.53 (d, 2H), 7.61 (d, 1H), 7.78 (t, 1H), 7.93 (d, 2H), 8.58 (d, 1H).<br>LC-MS (Method 2):<br>R$_t$ = 1.47 min; m/z = 476/478 (M + H)$^+$. |

| Example | Name/Structure/Starting materials | Analytical data |
|---|---|---|
| 46 | (4-{[2-(4-chlorophenyl)imidazo[1,2-a]pyridin-3-yl]methyl}piperazin-1-yl)[6-(tetrahydro-2H-pyran-4-yloxy)pyridin-2-yl]methanone<br>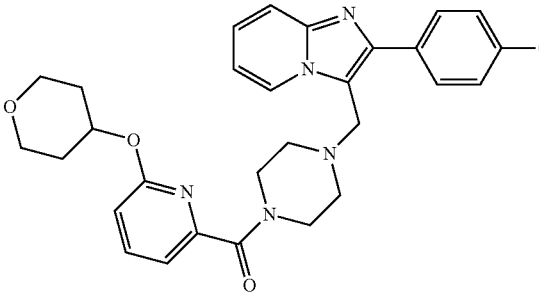<br>from 2-(4-chlorophenyl)-3-(piperazin-1-ylmethyl)imidazo[1,2-a]pyridine dihydrochloride and 6-(tetrahydro-2H-pyran-4-yloxy)pyridine-2-carboxylic acid (according to Synthesis method 3) | $^1$H-NMR (400 MHz, DMSO-d$_6$, δ/ppm): 1.52-1.64 (m, 2H), 1.87-1.97 (m, 2H), 2.41 (br. s, 2H), 2.57 (br. s, 2H), 3.35-3.46 (m, 4H), 3.61 (br. s, 2H), 3.75-3.84 (m, 2H), 4.05 (s, 2H), 5.04-5.14 (m, 1H), 6.86 (d, 1H), 6.98 (t, 1H), 7.14 (d, 1H), 7.32 (t, 1H), 7.53 (d, 2H), 7.61 (d, 1H), 7.79 (t, 1H), 7.93 (d, 2H), 8.59 (d, 1H).<br>LC-MS (Method 2):<br>R$_t$ = 1.40 min; m/z = 532/534 (M + H)$^+$. |
| 47 | (4-{[2-(4-bromophenyl)imidazo[1,2-a]pyridin-3-yl]methyl}piperazin-1-yl)(6-methoxypyridin-2-yl)methanone<br>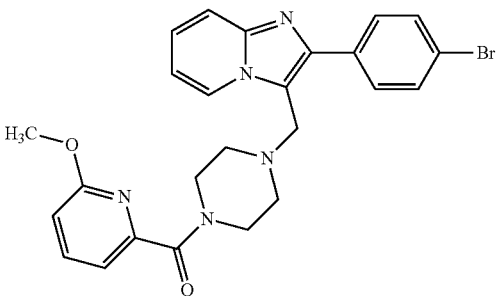<br>from 2-(4-bromophenyl)-3-(piperazin-1-ylmethyl)imidazo[1,2-a]pyridine dihydrochloride and 6-methoxypyridine-2-carboxylic acid (according to Synthesis method 3) | $^1$H-NMR (400 MHz, DMSO-d$_6$): δ [ppm] = 2.41-2.48 (m, 2H), 2.48-2.59 (m, 2H, partially hidden by DMSO signal), 3.42 (br. s, 2H), 3.61 (br. s, 2H), 3.80 (s, 3H), 4.04 (s, 2H), 6.89 (d, 1H), 6.98 (t, 1H), 7.15 (d, 1H), 7.32 (t, 1H), 7.61 (d, 1H), 7.67 (d, 2H), 7.80 (t, 1H), 7.86 (d, 2H), 8.58 (d, 1H).<br>LC-MS (Method 1):<br>R$_t$ = 0.80 min; m/z = 506/508 (M + H)$^+$. |
| 48 | (4-{[2-(4-fluorophenyl)imidazo[1,2-a]pyridin-3-yl]methyl}piperazin-1-yl)(cyclopentyl)methanone<br>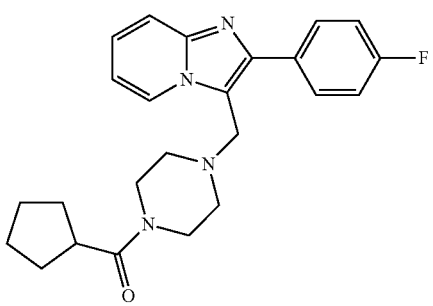<br>from 2-(4-fluorophenyl)-3-(piperazin-1-ylmethyl)imidazo[1,2-a]pyridine and cyclopentanecarboxylic acid (according to Synthesis method 8) | $^1$H-NMR (400 MHz, DMSO-d$_6$): δ [ppm] = 1.43-1.77 (m, 8H), 2.34-2.46 (m, 4H), 2.87-2.98 (m, 1H), 3.37-3.50 (m, 4H), 4.00 (s, 2H), 6.98 (t, 1H), 7.25-7.35 (m, 3H), 7.60 (d, 1H), 7.88-7.97 (m, 2H), 8.58 (d, 1H).<br>LC-MS (Method 1):<br>R$_t$ = 0.70 min; m/z = 407 (M + H)$^+$. |

| Example | Name/Structure/Starting materials | Analytical data |
|---|---|---|
| 49 | (4-{[2-(4-fluorophenyl)imidazo[1,2-a]pyridin-3-yl]methyl}piperazin-1-yl)(cyclobutyl)methanone<br>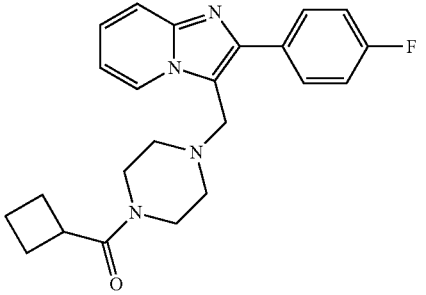<br>from 2-(4-fluorophenyl)-3-(piperazin-1-ylmethyl)imidazo[1,2-a]pyridine and cyclobutanecarboxylic acid (according to Synthesis method 8) | $^1$H-NMR (400 MHz, DMSO-d$_6$): δ [ppm] = 1.65-1.76 (m, 1H), 1.79-1.93 (m, 1H), 1.98-2.18 (m, 4H), 2.32-2.43 (m, 4H), 3.21-3.35 (m, 2H, partially hidden by H$_2$O signal), 3.36-3.44 (m, 2H), 3.99 (s, 2H), 6.97 (td, 1H), 7.25-7.34 (m, 3H), 7.60 (d, 1H), 7.87-7.96 (m, 2H), 8.56 (d, 1H).<br>LC-MS (Method 1):<br>R$_t$ = 0.65 min; m/z = 393 (M + H)$^+$. |
| 50 | (5-fluoro-2-methoxyphenyl)(4-{[2-(4-fluorophenyl)imidazo[1,2-a]pyridin-3-yl]methyl}piperazin-1-yl)methanone<br>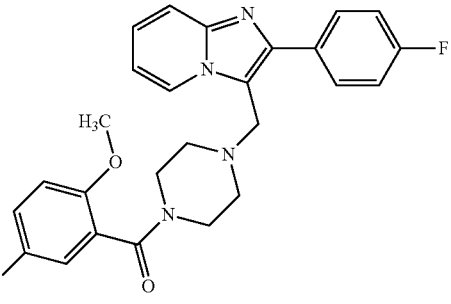<br>from 2-(4-fluorophenyl)-3-(piperazin-1-ylmethyl)imidazo[1,2-a]pyridine and 5-fluoro-2-methoxybenzoic acid (according to Synthesis method 8) | $^1$H-NMR (400 MHz, DMSO-d$_6$): δ [ppm] = 2.26-2.61 (m, 4H, partially hidden by DMSO signal), 3.03-3.14 (m, 2H), 3.45-3.57 (m, 1H), 3.57-3.68 (m, 1H), 3.75 (s, 3H), 4.01 (s, 2H), 6.97 (t, 1H), 7.01-7.12 (m, 2H), 7.16-7.25 (m, 1H), 7.31 (t, 3H), 7.60 (d, 1H), 7.85-7.97 (m, 2H), 8.56 (d, 1H).<br>LC-MS (Method 1):<br>R$_t$ = 0.69 min; m/z = 463 (M + H)$^+$. |
| 51 | (2-chloro-5-fluorophenyl)(4-{[2-(4-fluorophenyl)imidazo[1,2-a]pyridin-3-yl]methyl}piperazin-1-yl)methanone<br>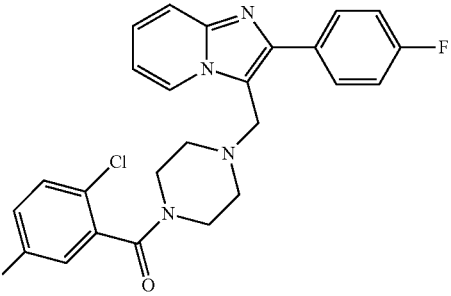<br>from 2-(4-fluorophenyl)-3-(piperazin-1-ylmethyl)imidazo[1,2-a]pyridine and 2-chloro-5-fluorobenzoic acid (according to Synthesis method 8) | $^1$H-NMR (400 MHz, DMSO-d$_6$): δ [ppm] = 2.38-2.46 (m, 2H), 2.46-2.58 (m, 2H, hidden by DMSO signal), 3.06-3.16 (m, 2H), 3.54-3.65 (m, 2H), 4.02 (s, 2H), 6.98 (t, 1H), 7.27-7.36 (m, 5H), 7.53-7.63 (m, 2H), 7.86-7.85 (m, 2H), 8.58 (d, 1H).<br>LC-MS (Method 1):<br>R$_t$ = 0.74 min; m/z = 467/469 (M + H)$^+$. |

| Example | Name/Structure/Starting materials | Analytical data |
|---|---|---|
| 52 | (4-{[2-(4-fluorophenyl)imidazo[1,2-a]pyridin-3-yl]methyl}piperazin-1-yl)(2-methoxyphenyl)methanone<br />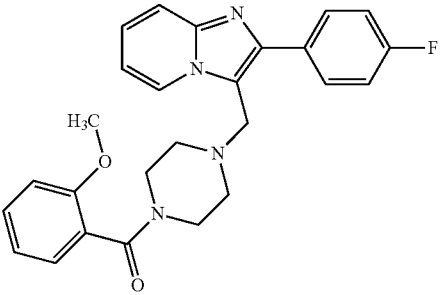<br />from 2-(4-fluorophenyl)-3-(piperazin-1-ylmethyl)imidazo[1,2-a]pyridine and 2-methoxybenzoic acid (according to Synthesis method 8) | $^1$H-NMR (400 MHz, DMSO-$d_6$): δ [ppm] = 2.26-2.36 (m, 1H), 2.36-2.44 (m, 1H), 2.44-2.61 (m, 2H, partially hidden by DMSO signal), 3.04-3.14 (m, 2H), 3.45-3.56 (m, 1H), 3.60-3.70 (m, 1H), 3.76 (s, 3H), 4.00 (s, 2H), 6.98 (t, 2H), 7.05 (d, 1H), 7.15 (d, 1H), 7.31 (t, 3H), 7.34-7.41 (m, 1H), 7.59 (d, 1H), 7.87-7.96 (m, 2H), 8.57 (d, 1H).<br />LC-MS (Method 1):<br />$R_t$ = 0.67 min; m/z = 445 (M + H)$^+$. |
| 53 | (2-fluorophenyl)(4-{[2-(4-isopropylphenyl)imidazo[1,2-a]pyridin-3-yl]methyl}piperazin-1-yl)methanone<br />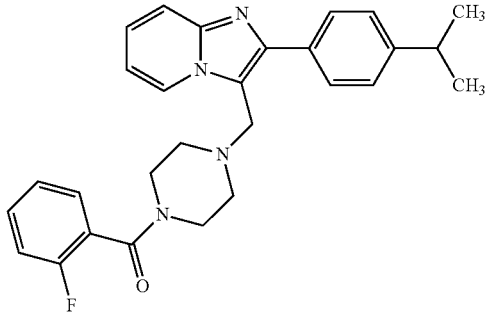<br />from 2-(4-isopropylphenyl)-3-(piperazin-1-ylmethyl)imidazo[1,2-a]pyridine dihydrochloride and 2-fluorobenzoic acid (according to Synthesis method 3) | $^1$H-NMR (400 MHz, DMSO-$d_6$): δ [ppm] = 1.25 (d, 6H), 2.37-2.45 (m, 2H), 2.47-2.57 (m, 2H, partially hidden by DMSO signal), 2.88-3.00 (m, 1H), 3.19 (br. s, 2H), 3.62 (br. s, 2H), 4.03 (s, 2H), 6.95 (t, 1H), 7.22-7.32 (m, 3H), 7.32-7.41 (m, 3H), 7.45-7.53 (m, 1H), 7.59 (d, 1H), 7.80 (d, 2H), 8.56 (d, 1H).<br />LC-MS (Method 1):<br />$R_t$ = 0.80 min; m/z = 457 (M + H)$^+$. |
| 54 | cyclopentyl(4-{[2-(4-isopropylphenyl)imidazo[1,2-a]pyridin-3-yl]methyl}piperazin-1-yl)methanone<br />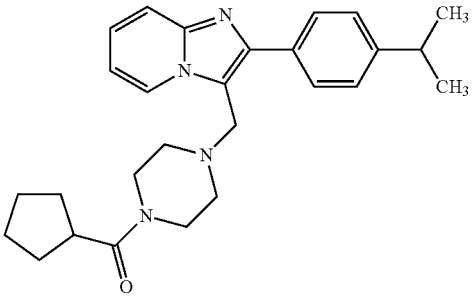<br />from 2-(4-isopropylphenyl)-3-(piperazin-1-ylmethyl)imidazo[1,2-a]pyridine dihydrochloride and cyclopentanecarboxylic acid (according to Synthesis method 3) | $^1$H-NMR (400 MHz, DMSO-$d_6$): δ [ppm] = 1.25 (d, 6H), 1.43-1.78 (m, 8H), 2.35-2.47 (m, 4H), 2.87-3.00 (m, 2H), 3.37-3.50 (m, 4H), 4.01 (s, 2H), 6.96 (t, 1H), 7.29 (t, 1H), 7.34 (d, 2H), 7.59 (d, 1H), 7.81 (d, 2H), 8.56 (d, 1H).<br />LC-MS (Method 1):<br />$R_t$ = 0.83 min; m/z = 431 (M + H)$^+$. |

-continued

| Example | Name/Structure/Starting materials | Analytical data |
|---|---|---|
| 55 | (4-{[2-(4-isopropylphenyl)imidazo[1,2-a]pyridin-3-yl]methyl}piperazin-1-yl)(6-methoxypyridin-2-yl)methanone<br>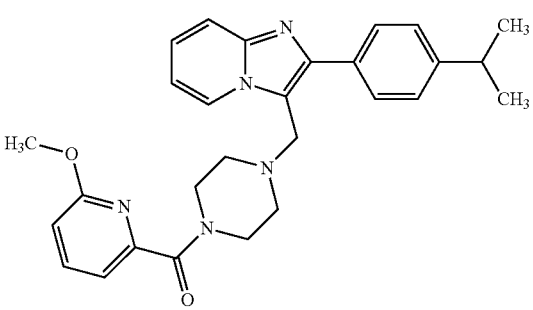<br>from 2-(4-isopropylphenyl)-3-(piperazin-1-ylmethyl)imidazo[1,2-a]pyridine dihydrochloride and 6-methoxypyridine-2-carboxylic acid (according to Synthesis method 3) | $^1$H-NMR (400 MHz, DMSO-d$_6$): δ [ppm] = 1.25 (d, 6H), 2.43-2.53 (m, 2H, partially hidden by DMSO signal), 2.52-2.58 (m, 2H), 2.89-2.99 (m, 1H), 3.42 (br. s, 2H), 3.61 (br. s, 2H), 3.81 (s, 3H), 4.04 (s, 2H), 6.89 (d, 1H), 6.96 (t, 1H), 7.15 (d, 1H), 7.27-7.32 (m, 1H), 7.34 (d, 2H), 7.59 (d, 1H), 7.77-7.83 (m, 3H), 8.56 (d, 1H).<br>LC-MS (Method 2):<br>R$_t$ = 1.42 min; m/z = 470 (M + H)$^+$. |
| 56 | cyclopentyl(4-{[2-(4-methylphenyl)imidazo[1,2-a]pyridin-3-yl]methyl}piperazin-1-yl)methanone<br>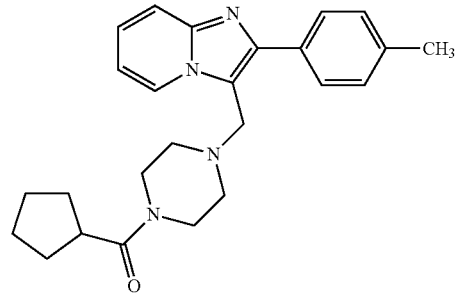<br>from 2-(4-methylphenyl)-3-(piperazin-1-ylmethyl)imidazo[1,2-a]pyridine dihydrochloride and cyclopentanecarboxylic acid (according to Synthesis method 3) | $^1$H-NMR (400 MHz, DMSO-d$_6$): δ [ppm] = 1.42-1.78 (m, 8H), 2.30-2.45 (m, 4H), 2.36 (s, 3H), 2.87-2.99 (m, 1H), 3.36-3.50 (m, 4H), 4.00 (s, 2H), 6.95 (t, 1H), 7.23-7.33 (m, 3H), 7.59 (d, 1H), 7.76 (d, 2H), 8.55 (d, 1H).<br>LC-MS (Method 1):<br>R$_t$ = 0.72 min; m/z = 403 (M + H)$^+$. |
| 57 | cyclohexyl(4-{[2-(4-methylphenyl)imidazo[1,2-a]pyridin-3-yl]methyl}piperazin-1-yl)methanone<br>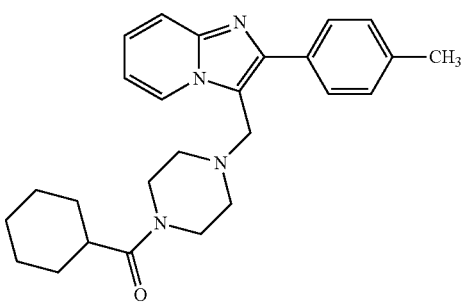<br>from 2-(4-methylphenyl)-3-(piperazin-1-ylmethyl)imidazo[1,2-a]pyridine dihydrochloride and cyclohexanecarboxylic acid (according to Synthesis method 3) | $^1$H-NMR (400 MHz, DMSO-d$_6$): δ [ppm] = 1.04-1.38 (m, 5H), 1.51-1.73 (m, 5H), 2.29-2.44 (m, 4H), 2.35 (s, 3H), 2.45-2.57 (m, 1H, hidden by DMSO signal), 3.41 (br. s, 4H), 4.00 (s, 2H), 6.95 (t, 1H), 7.21-7.32 (m, 3H), 7.59 (d, 1H), 7.76 (d, 2H), 8.55 (d, 1H).<br>LC-MS (Method 1):<br>R$_t$ = 0.76 min; m/z = 417 (M + H)$^+$. |

| Example | Name/Structure/Starting materials | Analytical data |
|---|---|---|
| 58 | (2-methoxyphenyl)(4-{[2-(4-methylphenyl)imidazo[1,2-a]pyridin-3-yl]methyl}piperazin-1-yl)methanone<br>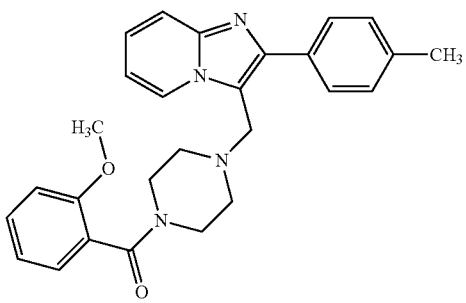<br>from 2-(4-methylphenyl)-3-(piperazin-1-ylmethyl)imidazo[1,2-a]pyridine dihydrochloride and 2-methoxybenzoic acid (according to Synthesis method 3) | $^1$H-NMR (400 MHz, DMSO-$d_6$): δ [ppm] = 2.24-2.56 (m, 4H, partially hidden by DMSO signal), 2.36 (s, 3H), 3.08 (t, 2H), 3.45-3.57 (m, 1H), 3.58-3.68 (m, 1H), 3.78 (s, 3H), 4.01 (s, 2H), 6.92-7.01 (m, 2H), 7.05 (d, 1H), 7.15 (dd, 1H), 7.25-7.32 (m, 3H), 7.34-7.40 (m, 1H), 7.58 (d, 1H), 7.75 (d, 2H), 8.54 (d, 1H).<br>LC-MS (Method 1):<br>$R_t$ = 0.68 min; m/z = 441 (M + H)$^+$. |
| 59 | (6-methoxypyridin-2-yl)(4-{[2-(4-methylphenyl)imidazo[1,2-a]pyridin-3-yl]methyl}piperazin-1-yl)methanone<br>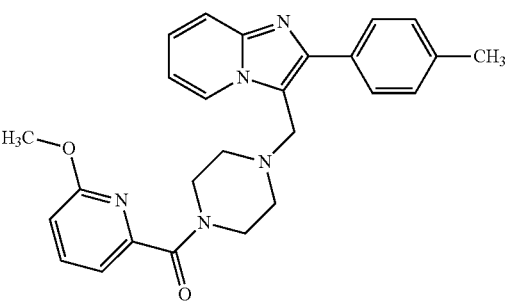<br>from 2-(4-methylphenyl)-3-(piperazin-1-ylmethyl)imidazo[1,2-a]pyridine dihydrochloride and 6-methoxypyridine-2-carboxylic acid (according to Synthesis method 3) | $^1$H-NMR (400 MHz, DMSO-$d_6$): δ [ppm] = 2.36 (s, 3H), 2.44 (br. s, 2H), 2.48-2.58 (m, 2H, hidden by DMSO signal), 3.36-3.46 (m, 2H), 3.60 (br. s, 2H), 3.80 (s, 3H), 4.03 (s, 2H), 6.88 (d, 1H), 6.96 (t, 1H), 7.15 (d, 1H), 7.25-7.33 (m, 3H), 7.59 (d, 1H), 7.72-7.78 (m, 2H), 7.80 (d, 1H), 8.56 (d, 1H).<br>LC-MS (Method 1):<br>$R_t$ = 0.68 min; m/z = 442 (M + H)$^+$. |
| 60 | (4-(3-{[4-(2-fluorobenzoyl)piperazin-1-yl]methyl}imidazo[1,2-a]pyridin-2-yl)benzonitrile<br>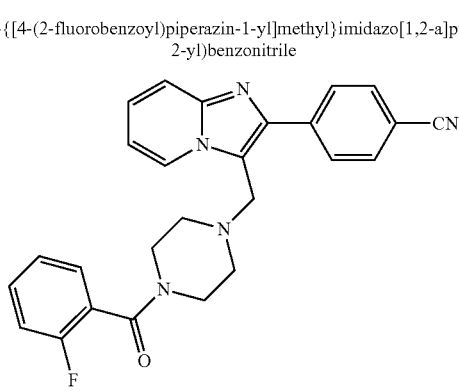<br>from 2-(4-cyanophenyl)-3-(piperazin-1-ylmethyl)imidazo[1,2-a]pyridine dihydrochloride and 2-fluorobenzoic acid (according to Synthesis method 3) | $^1$H-NMR (400 MHz, DMSO-$d_6$): δ [ppm] = 2.38-2.46 (m, 2H), 2.46-2.58 (m, 2H, hidden by DMSO signal), 3.19 (br. s, 2H), 3.62 (br. s, 2H), 4.07 (s, 2H), 7.01 (t, 1H), 7.22-7.41 (m, 4H), 7.44-7.53 (m, 1H), 7.63 (d, 1H), 7.93 (d, 2H), 8.12 (d, 2H), 8.62 (d, 1H).<br>LC-MS (Method 2):<br>$R_t$ = 1.35 min; m/z = 440 (M + H)$^+$. |

-continued

| Example | Name/Structure/Starting materials | Analytical data |
|---|---|---|
| 61 | 4-[3-({4-[(6-methoxypyridin-2-yl)carbonyl]piperazin-1-yl}methyl)imidazo[1,2-a]pyridin-2-yl]benzonitrile<br>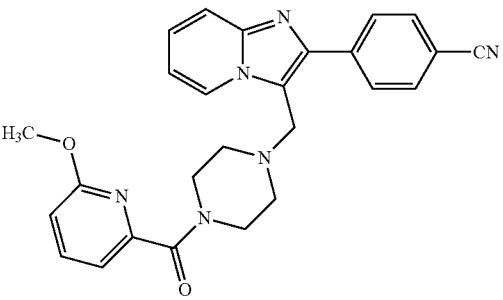<br>from 2-(4-cyanophenyl)-3-(piperazin-1-ylmethyl)imidazo[1,2-a]pyridine dihydrochloride and 6-methoxypyridine-2-carboxylic acid (according to Synthesis method 3) | $^1$H-NMR (400 MHz, DMSO-$d_6$): δ [ppm] = 2.41-2.61 (m, 4H, partially hidden by DMSO signal), 3.42 (br. s, 2H), 3.61 (br. s, 2H), 3.81 (s, 3H), 4.08 (s, 2H), 6.89 (d, 1H), 7.01 (t, 1H), 7.15 (d, 1H), 7.35 (t, 1H), 7.64 (d, 1H), 7.80 (t, 1H), 7.93 (d, 2H), 8.13 (d, 2H), 8.62 (d, 1H).<br>LC-MS (Method 1):<br>$R_t$ = 0.69 min; m/z = 453 (M + H)$^+$. |
| 62 | 4-(3-{[4-(cyclopentylcarbonyl)piperazin-1-yl]methyl}imidazo[1,2-a]pyridin-2-yl)benzonitrile<br>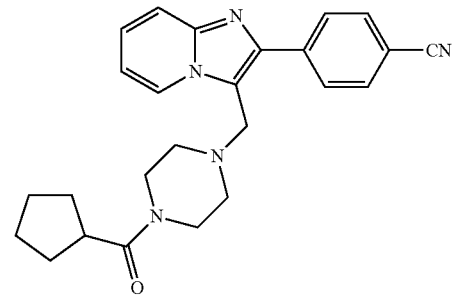<br>from 2-(4-cyanophenyl)-3-(piperazin-1-ylmethyl)imidazo[1,2-a]pyridine dihydrochloride and cyclopentanecarboxylic acid (according to Synthesis method 3) | $^1$H-NMR (400 MHz, DMSO-$d_6$): δ [ppm] = 1.42-1.84 (m, 8H), 2.35-2.47 (m, 4H), 2.88-2.99 (m, 1H), 3.37-3.51 (m, 4H), 4.05 (s, 2H), 7.01 (t, 1H), 7.35 (t, 1H), 7.64 (d, 1H), 7.93 (d, 2H), 8.13 (d, 2H), 8.62 (d, 1H).<br>LC-MS (Method 1):<br>$R_t$ = 0.73 min; m/z = 414 (M + H)$^+$. |
| 63 | 4-(3-{[4-(cyclohexylcarbonyl)piperazin-1-yl]methyl}imidazo[1,2-a]pyridin-2-yl)benzonitrile<br>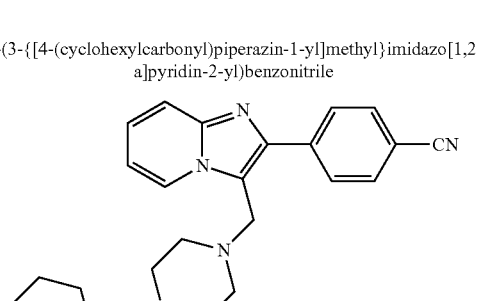<br>from 2-(4-cyanophenyl)-3-(piperazin-1-ylmethyl)imidazo[1,2-a]pyridine dihydrochloride and cyclohexanecarboxylic acid (according to Synthesis method 3) | $^1$H-NMR (400 MHz, DMSO-$d_6$): δ [ppm] = 1.07-1.36 (m, 5H), 1.55-1.72 (m, 5H), 2.36-2.46 (m, 4H), 2.47-2.59 (m, 1H, hidden by DMSO signal), 3.36-3.48 (m, 4H), 4.05 (s, 2H), 7.01 (t, 1H), 7.35 (t, 1H), 7.64 (d, 1H), 7.93 (d, 2H), 8.13 (d, 2H), 8.61 (d, 1H).<br>LC-MS (Method 2):<br>$R_t$ = 1.49 min; m/z = 428 (M + H)$^+$. |

-continued

| Example | Name/Structure/Starting materials | Analytical data |
|---|---|---|
| 64 | (4-{[2-(4-tert-butylphenyl)imidazo[1,2-a]pyridin-3-yl]methyl}piperazin-1-yl)(6-methoxypyridin-2-yl)methanone<br><br>from 2-(4-tert-butylphenyl)-3-(piperazin-1-ylmethyl)imidazo[1,2-a]pyridine dihydrochloride and 6-methoxypyridine-2-carboxylic acid (according to Synthesis method 3) | $^1$H-NMR (400 MHz, DMSO-$d_6$): δ [ppm] = 1.33 (s, 9H), 2.38-2.60 (m, 4H, partially hidden by DMSO signal), 3.43 (br. s, 2H), 3.61 (br. s, 2H), 3.81 (s, 3H), 4.05 (s, 2H), 6.88 (d, 1H), 6.96 (t, 1H), 7.16 (d, 1H), 7.29 (t, 1H), 7.49 (d, 2H), 7.59 (d, 1H), 7.76-7.86 (m, 3H), 8.56 (d, 1H).<br>LC-MS (Method 5):<br>$R_t$ = 1.07 min; m/z = 484 (M + H)$^+$. |
| 65 | (4-{[2-(4-tert-butylphenyl)imidazo[1,2-a]pyridin-3-yl]methyl}piperazin-1-yl)(2-fluorophenyl)methanone<br><br>from 2-(4-tert-butylphenyl)-3-(piperazin-1-ylmethyl)imidazo[1,2-a]pyridine dihydrochloride and 2-fluorobenzoic acid (according to Synthesis method 3) | $^1$H-NMR (400 MHz, DMSO-$d_6$): δ [ppm] = 1.33 (s, 9H), 2.38-2.46 (m, 2H), 2.46-2.58 (m, 2H, hidden by DMSO signal), 3.14-3.24 (m, 2H), 3.56-3.67 (m, 2H), 4.04 (s, 2H), 6.95 (t, 1H), 7.23-7.33 (m, 3H), 7.34-7.42 (m, 1H), 7.44-7.53 (m, 3H), 7.59 (d, 1H), 7.82 (d, 2H), 8.56 (d, 1H).<br>LC-MS (Method 2):<br>$R_t$ = 1.53 min; m/z = 471 (M + H)$^+$. |
| 66 | (4-{[2-(4-tert-butylphenyl)imidazo[1,2-a]pyridin-3-yl]methyl}piperazin-1-yl)(cyclopentyl)methanone<br><br>from 2-(4-tert-butylphenyl)-3-(piperazin-1-ylmethyl)imidazo[1,2-a]pyridine dihydrochloride and cyclopentanecarboxylic acid (according to Synthesis method 3) | $^1$H-NMR (400 MHz, DMSO-$d_6$): δ [ppm] = 1.33 (s, 9H), 1.42-1.78 (m, 8H), 2.34-2.47 (m, 4H), 2.87-2.99 (m, 1H), 3.36-3.50 (m, 4H), 4.02 (s, 2H), 6.96 (t, 1H), 7.29 (t, 1H), 7.49 (d, 2H), 7.60 (d, 1H), 7.83 (d, 2H), 8.56 (d, 1H).<br>LC-MS (Method 5):<br>$R_t$ = 1.11 min; m/z = 445 (M + H)$^+$. |

Example 67

(4-{[2-(4-Chlorophenyl)imidazo[1,2-a]pyridin-3-yl]methyl}piperazin-1-yl)[6-(trifluoromethoxy)pyridin-2-yl]methanone

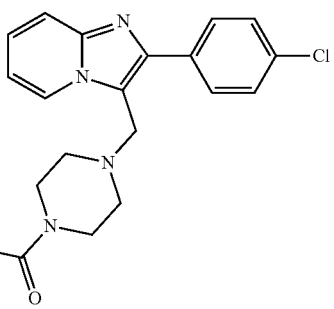

75 mg (0.36 mmol) of 6-(trifluoromethoxy)pyridine-2-carboxylic acid were dissolved in 1.8 ml of DMF, 148 mg (0.39 mmol) of 2-(7-aza-1H-benzotriazol-1-yl)-1,1,3,3-tetramethyluronium hexafluorophosphate (HATU) were added and the mixture was stirred at room temperature for 30 min. 120 mg (0.30 mmol) of 2-(4-chlorophenyl)-3-(piperazin-1-ylmethyl)imidazo[1,2-a]pyridine dihydrochloride and 0.16 ml (0.90 mmol) of N,N-diisopropylethylamine were then added, and the mixture was stirred further at room temperature overnight. The reaction mixture was then separated directly into its components by preparative HPLC (Method 6). This gave 112 mg (0.22 mmol, 73% of theory) of the title compound.

LC-MS (Method 2): $R_t$=1.55 min; m/z=516/518 (M+H)$^+$.

$^1$H-NMR (400 MHz, DMSO-$d_6$): δ [ppm]=2.44 (br. t, 2H), 2.55 (br. t, 2H), 3.37 (br. t, 2H), 3.61 (br. s, 2H), 4.05 (s, 2H), 6.98 (td, 1H), 7.32 (ddd, 1H), 7.38 (d, 1H), 7.53 (d, 2H), 7.58-7.65 (m, 2H), 7.91 (d, 2H), 8.14 (t, 1H), 8.58 (d, 1H).

Example 68

(4-{[2-(4-Chlorophenyl)imidazo[1,2-a]pyridin-3-yl]methyl}piperazin-1-yl)(3-fluoro-6-methoxypyridin-2-yl)methanone

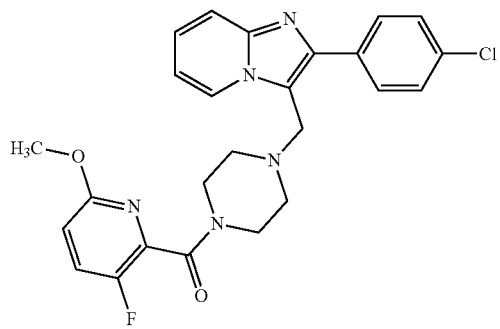 [SMILES: COc1ccc(F)c(C(=O)N2CCN(Cc3c(-c4ccc(Cl)cc4)nc4ccccn34)CC2)n1]

62 mg (0.36 mmol) of 3-fluoro-6-methoxypyridine-2-carboxylic acid were dissolved in 1.8 ml of DMF, 148 mg (0.39 mmol) of 2-(7-aza-1H-benzotriazol-1-yl)-1,1,3,3-tetramethyluronium hexafluorophosphate (HATU) were added and the mixture was stirred at room temperature for 30 min. 120 mg (0.30 mmol) of 2-(4-chlorophenyl)-3-(piperazin-1-ylmethyl)imidazo[1,2-a]pyridine dihydrochloride and 0.16 ml (0.90 mmol) of N,N-diisopropylethylamine were then added, and the mixture was stirred further at room temperature overnight. The reaction mixture was then separated directly into its components by preparative HPLC (Method 6). This gave 118 mg of still contaminated title compound which was re-purified by another preparative HPLC (Method 6). This gave 91 mg (0.19 mmol, 63% of theory) of the title compound.

LC-MS (Method 2): $R_t$=1.36 min; m/z=480/482 (M+H)$^+$.

$^1$H-NMR (400 MHz, DMSO-$d_6$): δ [ppm]=2.42 (br. t, 2H), 2.47-2.59 (m, 2H, partially hidden by DMSO signal), 3.23 (br. t, 2H), 3.62 (br. s, 2H), 3.79 (s, 3H), 4.05 (s, 2H), 6.90-7.02 (m, 2H), 7.32 (ddd, 1H), 7.53 (d, 2H), 7.61 (d, 1H), 7.77 (t, 1H), 7.92 (d, 2H), 8.59 (d, 1H).

Example 69

(4-{[2-(4-Cyclopropylphenyl)imidazo[1,2-a]pyridin-3-yl]methyl}piperazin-1-yl)(2-fluorophenyl)methanone

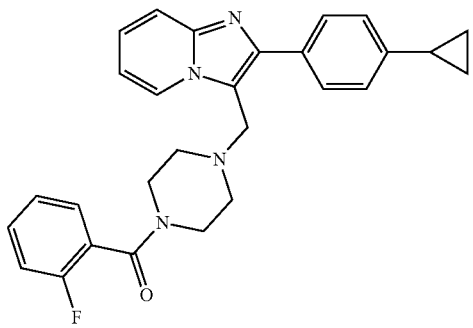 [SMILES: O=C(c1ccccc1F)N1CCN(Cc2c(-c3ccc(C4CC4)cc3)nc3ccccn23)CC1]

100 mg (0.20 mmol) of (4-{[2-(4-bromophenyl)imidazo[1,2-a]pyridin-3-yl]methyl}piperazin-1-yl)(2-fluorophenyl)methanone were taken up in 8 ml of toluene and 0.4 ml of water. 35 mg (0.41 mmol) of cyclopropylboronic acid, 151 mg (0.71 mmol) of potassium phosphate, 4.6 mg (0.02 mmol) of palladium(II) acetate and 11 mg (0.04 mmol) of tricyclohexylphosphine were then added in succession to the reaction solution. The reaction solution was then heated to 80° C. and stirred at this temperature overnight. After cooling to room temperature, the reaction mixture was initially filtered through kieselguhr and then separated into its components by preparative HPLC (Method 6). This gave 41 mg (0.09 mmol, 43% of theory) of the title compound.

LC-MS (Method 2): $R_t$=1.36 min; m/z=455 (M+H)$^+$.

$^1$H-NMR (400 MHz, DMSO-$d_6$): δ [ppm]=0.68-0.76 (m, 2H), 0.94-1.03 (m, 2H), 1.13-1.35 (m, 1H), 1.60-1.85 (m, 1H), 1.91-2.01 (m, 1H), 2.40 (br. s, 2H), 3.18 (br. s, 2H), 3.61 (br. s, 2H), 4.02 (s, 2H), 6.95 (td, 1H), 7.17 (d, 2H), 7.23-7.33 (m, 3H), 7.37 (td, 1H), 7.44-7.52 (m, 1H), 7.58 (d, 1H), 7.74 (d, 2H), 8.55 (d, 1H).

The following compounds were also prepared according to synthesis method 7 described above, using the starting materials stated in each case.

| Example | Name/Structure/Starting materials | Analytical data |
|---|---|---|
| 70 | 4-(3-{[4-(2-fluoro-5-methoxybenzoyl)piperazin-1-yl]methyl}imidazo[1,2-a]pyridin-2-yl)benzonitrile<br><br>from 2-(4-cyanophenyl)-3-(piperazin-1-ylmethyl)-imidazo[1,2-a]pyridine dihydrochloride and 2-fluoro-5-methoxybenzoic acid | $^1$H-NMR (400 MHz, DMSO-$d_6$),: δ [ppm] = 2.43 (br. s, 2H), 2.48-2.58 (m, 2H, partially hidden by DMSO signal), 3.15-3.24 (m, 2H), 3.60 (br. s, 2H), 3.75 (s, 3H), 4.07 (s, 2H), 6.88 (dd, 1H), 6.96-7.05 (m, 2H), 7.20 (t, 1H), 7.35 (ddd, 1H), 7.63 (d, 1H), 7.93 (d, 2H), 8.12 (d, 2H), 8.61 (d, 1H).<br>LC-MS (Method 2):<br>$R_t$ = 1.40 min; m/z = 470 (M + H)$^+$. |
| 71 | 4-[3-({4-[(6-methoxy-3-methylpyridin-2-yl)carbonyl]piperazin-1-yl}methyl)imidazo[1,2-a]pyridin-2-yl]benzonitrile<br><br>from 2-(4-cyanophenyl)-3-(piperazin-1-ylmethyl)-imidazo[1,2-a]pyridine dihydrochloride and 6-methoxy-3-methylpyridine-2-carboxylic acid | $^1$H-NMR (400 MHz, DMSO-$d_6$): δ [ppm] = 2.13 (s, 3H), 2.42 (br. t, 2H), 2.46-2.58 (m, 2H, partially hidden by DMSO signal), 3.10 (br. t, 2H), 3.61 (br. s, 2H), 3.77 (s, 3H), 4.08 (s, 2H), 6.77 (d, 1H), 7.01 (td, 1H), 7.35 (ddd, 1H), 7.62 (dd, 2H), 7.93 (d, 2H), 8.12 (d, 2H), 8.62 (d, 1H).<br>LC-MS (Method 1):<br>$R_t$ = 0.71 min; m/z = 467 (M + H)$^+$. |
| 72 | (4-{[2-(4-chlorophenyl)imidazo[1,2-a]pyridin-3-yl]methyl}piperazin-1-yl)(6-methoxy-3-methylpyridin-2-yl)methanone<br><br>from 2-(4-chlorophenyl)-3-(piperazin-1-ylmethyl)imidazo[1,2-a]pyridine dihydrochloride and 6-methoxy-3-methylpyridine-2-carboxylic acid | $^1$H-NMR (400 MHz, DMSO-$d_6$): δ [ppm] = 2.13 (s, 3H), 2.40 (br. t, 2H), 2.46-2.58 (m, 2H, partially hidden by DMSO signal), 3.10 (br. t, 2H), 3.61 (br. s, 2H), 3.76 (s, 3H), 4.03 (s, 2H), 6.77 (d, 1H), 6.98 (td, 1H), 7.32 (ddd, 1H), 7.53 (d, 2H), 7.60 (d, 2H), 7.92 (d, 2H), 8.59 (d, 1H).<br>LC-MS (Method 1):<br>$R_t$ = 0.75 min; m/z = 476/478 (M + H)$^+$. |

-continued

| Example | Name/Structure/Starting materials | Analytical data |
|---|---|---|
| 73 | (4-{[2-(4-tert-butylphenyl)imidazo[1,2-a]pyridin-3-yl]methyl}piperazin-1-yl)(6-methoxy-3-methylpyridin-2-yl)methanone<br>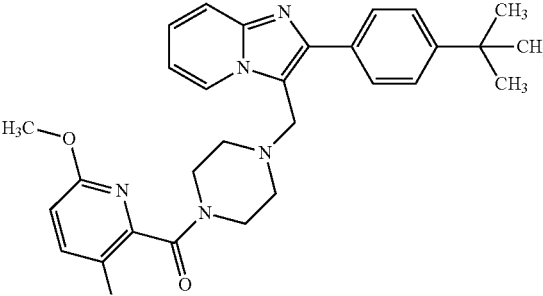<br>from 2-(4-tert.-butylphenyl)-3-(piperazin-1-yl-methyl)imidazo[1,2-a]pyridine dihydrochloride and 6-methoxy-3-methylpyridine-2-carboxylic acid | $^1$H-NMR (400 MHz, DMSO-$d_6$): δ [ppm] = 1.33 (s, 9H), 2.14 (s, 3H), 2.43 (br. t, 2H), 2.46-2.60 (m, 2H, partially hidden by DMSO signal), 3.11 (br. t, 2H), 3.62 (br. s, 2H), 3.77 (s, 3H), 4.04 (s, 2H), 6.77 (d, 1H), 6.95 (t, 1H), 7.29 (t, 1H), 7.49 (d, 2H), 7.60 (dd, 2H), 7.82 (d, 2H), 8.56 (d, 1H).<br>LC-MS (Method 1):<br>$R_t$ = 0.84 min; m/z = 498 (M + H)$^+$. |
| 74 | (4-{[2-(4-bromophenyl)imidazo[1,2-a]pyridin-3-yl]methyl}piperazin-1-yl)(6-methoxy-3-methyl-pyridin-2-yl)methanone<br>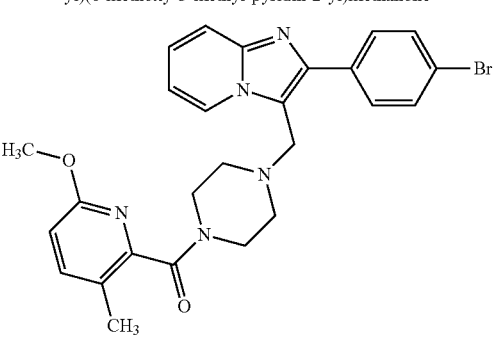<br>from 2-(4-bromophenyl)-3-(piperazin-1-ylmethyl)imidazo[1,2-a]pyridine dihydrochloride and 6-methoxy-3-methylpyridine-2-carboxylic acid | LC-MS (Method 1):<br>$R_t$ = 0.77 min; m/z = 520/522 (M + H)$^+$. |

B. ASSESSMENT OF PHARMACOLOGICAL EFFICACY

The pharmacological activity of the inventive compounds can be demonstrated by in vitro and in vivo studies, as known to the person skilled in the art. The application examples which follow describe the biological action of the inventive compounds, without restricting the invention to these examples.

B-1. In Vitro Electrophysiological Analysis of the Human TASK-1 and TASK-3 Channels Via Two-Electrode Voltage Clamp Technique in *Xenopus laevis* Oocytes

*Xenopus laevis* oocytes were selected as described elsewhere in an exemplary manner [Decher et al., *FEBS Lett.* 492, 84-89 (2001)]. Subsequently, the oocytes were injected with 0.5-5 ng of a cRNA solution coding for TASK-1 or TASK-3. For the electrophysiological analysis of the channel proteins expressed in the oocytes, the two-electrode voltage clamp technique [Stühmer, *Methods Enzymol.* 207, 319-339 (1992)] was used. The measurements were carried out as described [Decher et al., *FEBS Lett.* 492, 84-89 (2001)] at room temperature (21-22° C.) using a Turbo TEC 10CD amplifier (NPI), recorded at 2 kHz and filtered with 0.4 kHz. Substance administration was performed using a gravitation-driven perfusion system. Here, the oocyte is located in a measuring chamber and exposed to the solvent stream of 10 ml/min. The level in the measuring chamber is monitored and regulated by sucking off the solution using a peristaltic pump.

Table 1A below shows the half-maximum inhibition, determined in this test, of human TASK-1 and TASK-3 channels ($IC_{50}$) by representative working examples of the invention:

TABLE 1A

| Example No. | TASK-1 $IC_{50}$ [nM] | TASK-3 $IC_{50}$ [nM] |
|---|---|---|
| 1 | 7.9 ± 0.5 | 1.04 ± 0.23 |
| 2 | 2.8 ± 1.1 | 21.8 ± 2.1 |
| 3 | 4.2 ± 0.6 | 27.9 ± 4.0 |
| 4 | 9.7 ± 0.9 | 15.0 ± 2.1 |
| 39 | 13.4 ± 0.9 | 6.2 ± 1.1 |
| 47 | 4.9 ± 0.4 | 2.3 ± 0.3 |
| 54 | 4.3 ± 1.3 | 38.2 ± 1.4 |
| 55 | 45.0 ± 6.7 | 79.6 ± 10.8 |

From the data in Table 1A it is evident that both TASK-1 and TASK-3 are blocked. Accordingly, the results in Table 1A confirm the mechanism of action of the compounds according to the invention as dual TASK-1/3 inhibitors.

For comparison, some other {4-[(2-phenylimidazo[1,2-a]pyridin-3-yl)methyl]piperazin-1-yl}methanone derivatives which can be considered to be the structurally closest prior art [see the compounds described in WO 2014/187922-A1 as inhibitors of glucose transporters (GLUT)] were also assessed in this test with regard to inhibition of human TASK-1 and TASK-3 channels. The results obtained for these compounds are listed in Table 1B below:

TABLE 1B

| Structure of the comparative compound | TASK-1 % inhibition at 1 µM | TASK-1 % inhibition at 10 µM | TASK-1 IC$_{50}$ [µM] | TASK-3 % inhibition at 1 µM | TASK-3 % inhibition at 10 µM | TASK-3 IC$_{50}$ [µM] |
|---|---|---|---|---|---|---|
| (Example 64 in WO 2014/187922) | 6.3 ± 1.4 | 16.9 ± 3.2 | >30 | 9.3 ± 3.4 | 19.4 ± 4.6 | >30 |
| (Example 178 in WO 2014/187922) | 30.0 ± 3.3 | 59.9 ± 1.7 | >1 | 29.7 ± 2.6 | 56.1 ± 4.6 | >1 |
| (Example 196 in WO 2014/187922) | 47.2 ± 1.5 | 49.9 ± 3.3 | >1 | 12.1 ± 1.8 | 56.1 ± 2.3 | >1 |
| (Example 208 in WO 2014/187922) | 49.6 ± 6.7 | 75.0 ± 3.5 | >1 | 34.6 ± 2.7 | 73.6 ± 3.7 | >1 |

TABLE 1B-continued

| Structure of the comparative compound | TASK-1 % inhibition at 1 μM | TASK-1 % inhibition at 10 μM | TASK-1 IC$_{50}$ [μM] | TASK-3 % inhibition at 1 μM | TASK-3 % inhibition at 10 μM | TASK-3 IC$_{50}$ [μM] |
|---|---|---|---|---|---|---|
| 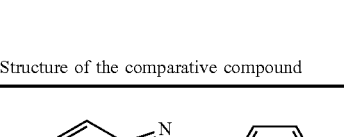<br>(Example 263 in WO 2014/187922) | 27.7 ± 4.5 | 55.2 ± 1.7 | >1 | 8.1 ± 2.6 | 48.2 ± 4.3 | >10 |

Thus, the comparative compounds of the prior art listed in Table 1B have, according to this test, a considerably weaker (lower by about 1 to 3 orders of magnitude) inhibitory activity with regard to TASK-1 and TASK-3 channels.

B-2. Inhibition of Recombinant TASK-1 and TASK-3 In Vitro

The investigations on the inhibition of the recombinant TASK-1 and TASK-3 channels were carried out using stably transfected CHO cells. Here, the compounds according to the invention were tested with administration of 40 mM of potassium chloride in the presence of a voltage-sensitive dye using the method described in detail in the following references [Whiteaker et al., Validation of FLIPR membrane potential dye for high-throughput screening of potassium channel modulators, *J. Biomol. Screen.* 6 (5), 305-312 (2001); Molecular Devices FLIPR Application Note: Measuring membrane potential using the FLIPR® membrane potential assay kit on Fluorometric Imaging Plate Reader (FLIPR®) systems, http://www.moleculardevices.com/reagents-supplies/assay-kits/ion-channels/flipr-membrane-potential-assay-kits]. The activity of the test substances was determined as their ability to inhibit a depolarization induced in the recombinant cells by 40 mM potassium chloride. The concentration which can block half of this depolarization is referred to as IC$_{50}$.

Table 2A below lists the IC$_{50}$ values from this assay determined for the working examples of the invention (some as mean values from multiple independent individual determinations):

TABLE 2A

| Example No. | TASK-1 IC$_{50}$ [nM] | TASK-3 IC$_{50}$ [nM] |
|---|---|---|
| 1 | 77 | 17 |
| 2 | 63 | 20 |
| 3 | 139 | 28 |
| 4 | 172 | 46 |
| 5 | 827 | 380 |
| 6 | 500 | 360 |
| 7 | 350 | 98 |
| 8 | 893 | 2500 |
| 9 | 232 | 200 |
| 11 | 378 | 240 |
| 12 | 409 | 71 |
| 13 | 672 | 350 |
| 14 | 481 | 310 |
| 15 | 1170 | 380 |
| 16 | 304 | 110 |
| 17 | 774 | 510 |
| 18 | 242 | 120 |
| 19 | 515 | 300 |
| 20 | 305 | 52 |
| 21 | 454 | 150 |
| 22 | 387 | 140 |
| 23 | 685 | 160 |
| 24 | 1140 | 810 |
| 25 | 1900 | 820 |
| 26 | 708 | 590 |
| 27 | 590 | 120 |
| 28 | 510 | 14 |
| 29 | 1200 | 99 |
| 30 | 1800 | 400 |
| 31 | 2100 | 1300 |
| 32 | 430 | 130 |
| 33 | 2500 | 2000 |
| 34 | 400 | 63 |
| 35 | 1250 | 790 |
| 36 | 520 | 190 |
| 37 | 370 | 60 |
| 38 | 1000 | 30 |
| 39 | 440 | 56 |
| 40 | 1000 | 770 |
| 41 | 1300 | 190 |
| 42 | 310 | 13 |
| 43 | 220 | 10 |
| 44 | 270 | 17 |
| 45 | 2000 | 63 |
| 46 | 1200 | 240 |
| 47 | 140 | 18 |
| 48 | 551 | 830 |
| 49 | 1830 | 1700 |
| 50 | 1620 | 1400 |
| 51 | 1890 | 1000 |
| 52 | 1160 | 560 |
| 53 | 2840 | 1000 |
| 54 | 479 | 225 |
| 55 | 490 | 141 |
| 56 | 642 | 700 |
| 57 | 962 | 2900 |
| 58 | 1910 | 1900 |
| 59 | 800 | 430 |
| 60 | 1700 | 4600 |
| 61 | 2050 | 1400 |

TABLE 2A-continued

| Example No. | TASK-1 IC$_{50}$ [nM] | TASK-3 IC$_{50}$ [nM] |
|---|---|---|
| 62 | 1200 | 3100 |
| 63 | 1300 | 1600 |
| 64 | 510 | 450 |
| 65 | 1100 | 750 |
| 66 | 1500 | 830 |
| 67 | 42 | 9.4 |
| 68 | 93 | 5.2 |
| 69 | 66 | 11 |
| 70 | 1800 | 350 |
| 71 | 230 | 16 |
| 72 | 71 | 3.0 |
| 73 | 170 | 17 |
| 74 | 67 | 9.1 |

From the data in Table 2A it is evident that both TASK-1 and TASK-3 are blocked. Accordingly, the results in Table 2A confirm the mechanism of action of the compounds according to the invention as dual TASK-1/3 inhibitors.

For comparison, some other {4-[(2-phenylimidazo[1,2-a]pyridin-3-yl)methyl]piperazin-1-yl}methanone derivatives which can be considered to be the structurally closest prior art [see the compounds described in WO 2014/187922-A1 as inhibitors of glucose transporters (GLUT)] were also assessed in this test with regard to inhibition of recombinant TASK-1 and TASK-3 channels. The results obtained for these compounds are listed in Table 2B below:

TABLE 2B

| Structure of the comparative compound | Example No. in WO 2014/187922 | TASK-1 IC$_{50}$ [nM] | TASK-3 IC$_{50}$ [nM] |
|---|---|---|---|
| (6-phenyl-2-(4-chlorophenyl)imidazo[1,2-a]pyridin-3-yl)methyl-4-(2-chlorobenzoyl)piperazine | 64 | 30000 | 2200 |
| (6-cyclopropyl-2-(4-chlorophenyl)imidazo[1,2-a]pyridin-3-yl)methyl-4-(3-fluorobenzoyl)piperazine | 178 | 30000 | 4800 |
| (6-cyclopropyl-2-(4-chlorophenyl)imidazo[1,2-a]pyridin-3-yl)methyl-4-(isonicotinoyl)piperazine | 196 | 30000 | 30000 |

TABLE 2B-continued

| Structure of the comparative compound | Example No. in WO 2014/187922 | TASK-1 IC$_{50}$ [nM] | TASK-3 IC$_{50}$ [nM] |
|---|---|---|---|
| [Structure: imidazo[1,2-a]pyridine with 2-(3-methoxyphenyl) and 3-(piperazinylmethyl) bearing cyclobutanecarbonyl] | 208 | 30000 | 30000 |
| [Structure: 6-cyclopropyl-imidazo[1,2-a]pyridine with 2-(4-chlorophenyl) and 3-(piperazinylmethyl) bearing pyrazine-2-carbonyl] | 263 | 30000 | 5700 |

Thus, in this test the comparative compounds from the prior art listed in Table 2B have no significant activity, which can at best be considered to be unspecific, with regard to TASK-1 and only weak to likewise insignificant inhibitory activity with regard to TASK-3.

B-3. Animal Model of Obstructive Sleep Apnoea in the Pig

Using negative pressure, it is possible to induce collapse and thus obstruction of the upper respiratory tract in anaesthetized, spontaneously breathing pigs [Wirth et al., *Sleep* 36, 699-708 (2013)].

Deutsche Landrasse pigs are used for the model. The pigs are anaesthetized and tracheotomized. One cannula each is inserted into the rostral and the caudal part of the trachea. Using a T connector, the rostral cannula is connected on the one hand to a device generating negative pressures and on the other hand to the caudal cannula. Using a T connector, the caudal cannula is connected to the rostral cannula and to a tube which allows spontaneous breathing circumventing the upper respiratory tract. By appropriate closing and opening of the tubes it is thus possible for the pig to change from normal nasal breathing to breathing via the caudal cannula during the time when the upper respiratory tract is isolated and connected to the device for generating negative pressures. The muscle activity of the *Musculus genioglossus* is recorded by electromyogram (EMG).

At certain points in time, the collapsibility of the upper respiratory tract is tested by having the pig breathe via the caudal cannula and applying negative pressures of −50, −100 and −150 cm water head (cm H$_2$O) to the upper respiratory tract. This causes the upper respiratory tract to collapse, which manifests itself in an interruption of the airflow and a pressure drop in the tube system. This test is carried out prior to the administration of the test substance and at certain intervals after the administration of the test substance. An appropriately effective test substance can prevent this collapse of the respiratory tract in the inspiratory phase.

After changeover from nasal breathing to breathing via the caudal cannula, it is not possible to measure any EMG activity of the *Musculus genioglossus* in the anaesthetized pig. As a further test, the negative pressure at which EMG activity restarts is then determined. This threshold value is, if a test substance is effective, shifted to more positive values. The test is likewise carried out prior to the administration of the test substance and at certain intervals after the administration of the test substance. Administration of the test substance can be intranasal, intravenous, subcutaneous, intraperitoneal or intragastral.

C. WORKING EXAMPLES FOR PHARMACEUTICAL COMPOSITIONS

The compounds of the invention can be converted to pharmaceutical formulations as follows:

Tablet:

Composition:

100 mg of the compound of the invention, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg. Diameter 8 mm, radius of curvature 12 mm.

Production:

The mixture of compound of the invention, lactose and starch is granulated with a 5% solution (w/w) of the PVP in water. The granules are dried and then mixed with the magnesium stearate for 5 minutes. This mixture is compressed in a conventional tabletting press (see above for format of the tablet). The guide value used for the pressing is a pressing force of 15 kN.

Suspension for Oral Administration:

Composition:

1000 mg of the compound of the invention, 1000 mg of ethanol (96%), 400 mg of Rhodigel® (xanthan gum from FMC, Pa., USA) and 99 g of water. 10 ml of oral suspension correspond to a single dose of 100 mg of the compound of the invention.

Production:

The Rhodigel is suspended in ethanol; the compound of the invention is added to the suspension. The water is added while stirring. The mixture is stirred for about 6 h before swelling of the Rhodigel is complete.

Solution for Oral Administration:

Composition:

500 mg of the compound of the invention, 2.5 g of polysorbate and 97 g of polyethylene glycol 400. 20 g of oral solution correspond to a single dose of 100 mg of the compound of the invention.

Production:

The compound of the invention is suspended in the mixture of polyethylene glycol and polysorbate with stirring. The stirring operation is continued until dissolution of the compound of the invention is complete.

i.v. Solution:

The compound of the invention is dissolved in a concentration below the saturation solubility in a physiologically acceptable solvent (e.g. isotonic saline solution, glucose solution 5% and/or PEG 400 solution 30%). The solution is subjected to sterile filtration and dispensed into sterile and pyrogen-free injection vessels.

Solution for Nasal Administration:

The compound of the invention is dissolved in a concentration below the saturation solubility in a physiologically acceptable solvent (e.g. purified water, phosphate buffer, citrate buffer). The solution may contain further additives for isotonization, for preservation, for adjusting the pH, for improvement in the solubility and/or for stabilization.

The invention claimed is:

1. A compound of the formula (I)

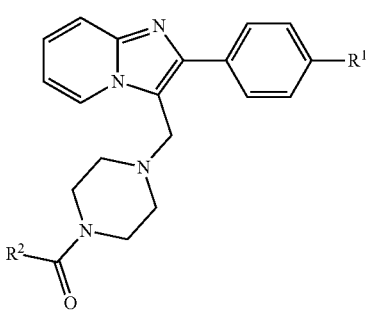

(I)

wherein $R^1$ is halogen, cyano, $(C_1-C_4)$-alkyl, cyclopropyl, or cyclobutyl;

$R^2$ is $(C_4-C_6)$-cycloalkyl, wherein a ring $CH_2$ group may be replaced by —O—, or is a phenyl group of the formula (a) or a pyridyl group of the formula (b)

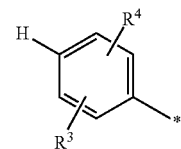

(a)

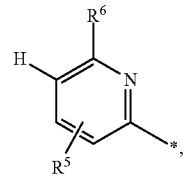

(b)

wherein * marks the bond to the adjacent carbonyl group;

$R^3$ is fluorine, chlorine, bromine, cyano, $(C_1-C_3)$-alkyl, or $(C_1-C_3)$-alkoxy, wherein $(C_1-C_3)$-alkyl and $(C_1-C_3)$-alkoxy may be substituted up to three times by fluorine;

$R^4$ is hydrogen, fluorine, chlorine, bromine, or methyl;

$R^5$ is hydrogen, fluorine, chlorine, bromine or methyl; and $R^6$ is hydrogen, $(C_1-C_3)$-alkoxy, cyclobutyloxy, oxetan-3-yloxy, tetrahydrofuran-3-yloxy, or tetrahydro-2H-pyran-4-yloxy, wherein $(C_1-C_3)$-alkoxy may be substituted up to three times by fluorine, or a salt, a solvate, or a solvate of a salt thereof.

2. The compound of the formula (I) according to claim 1, wherein $R^1$ is fluorine, chlorine, bromine, methyl, isopropyl, tert-butyl, or cyclopropyl;

$R^2$ is cyclobutyl, cyclopentyl, or cyclohexyl, or is a phenyl group of the formula (a) or a pyridyl group of the formula (b)

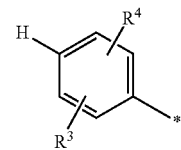

(a)

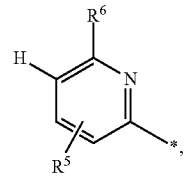

(b)

wherein * marks the bond to the adjacent carbonyl group;

$R^3$ is fluorine, chlorine, cyano, $(C_1-C_3)$-alkyl, $(C_1-C_3)$-alkoxy, or trifluoromethoxy, $R^4$ is hydrogen, fluorine, or chlorine, $R^5$ is hydrogen, fluorine, chlorine, bromine, or methyl; and $R^6$ is hydrogen or $(C_1-C_3)$-alkoxy, which may be substituted up to three times by fluorine, or a salt, a solvate, or a solvate of a salt thereof.

3. The compound of the formula (I) according to claim 1, wherein

R$^1$ is chlorine, bromine, isopropyl, or cyclopropyl;

R$^2$ is cyclobutyl, cyclopentyl, or cyclohexyl, or is a phenyl group of the formula (a) or a pyridyl group of the formula (b)

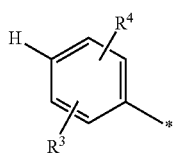

(a)

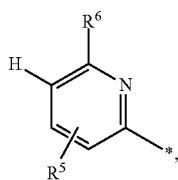

(b)

wherein * marks the bond to the adjacent carbonyl group;

R$^3$ is fluorine, chlorine, cyano, methyl, isopropyl, methoxy, or ethoxy;

R$^4$ is hydrogen, fluorine, or chlorine;

R$^5$ is hydrogen, chlorine, or bromine; and

R$^6$ is methoxy, difluoromethoxy, trifluoromethoxy, or isopropoxy, or a salt, a solvate, or a solvate of a salt thereof.

4. A process for preparing a compound of the formula (I) according to claim 1, comprising reacting a compound of formula (II)

(II)

wherein R$^1$ is as defined in claim 1,
in the presence of a suitable reducing agent either
[A] with a compound of formula (III)

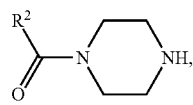

(III)

wherein R$^2$ is as defined in claim 1,
or
[B] with a protected piperazine derivative of formula (IV)

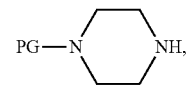

(IV)

wherein PG is a suitable amino protective group
to give a compound of formula (V)

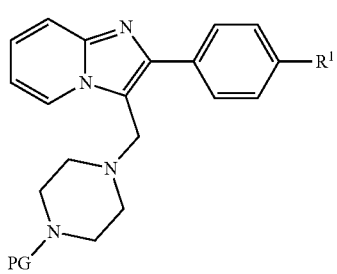

(V)

wherein PG and R$^1$ are as defined above,
removing the protective group PG to give a compound of formula (VI)

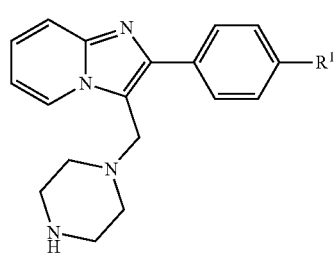

(VI)

wherein R$^1$ is as defined above;
reacting the compound of formula (VI) with a carboxylic acid of formula (VII)

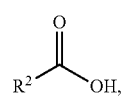

(VII)

wherein R$^2$ is as defined in claim 1,
with activation of the carboxylic acid function in (VII), or
reacting the compound of formula (VI) with the corresponding acid chloride of formula (VIII)

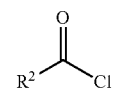

(VIII)

wherein R$^2$ is as defined in claim 1, to give the compound of formula (I), and optionally converting the compound of formula (I) to a solvate, a salt, or a solvate of a salt thereof.

5. A pharmaceutical composition comprising a compound according to claim 1 in combination with one or more inert, nontoxic, pharmaceutically suitable excipients.

6. A pharmaceutical combination comprising a compound according to claim 1 in combination with one or more further active compounds selected from the group consisting of respiratory stimulants, psychostimulating compounds, serotonin reuptake inhibitors, noradrenergic, serotonergic and tricyclic antidepressants, sGC stimulators, mineralocorticoid receptor antagonists, antiinflammatory drugs, immunomodulators, immunosuppressives and cytotoxic drugs.

7. A method for treatment of sleep-related respiratory disorders, obstructive sleep apneas, central sleep apneas, or snoring, comprising administering to a human or animal in need thereof an effective amount of a pharmaceutical composition according to claim 5.

8. A method for treatment of sleep-related respiratory disorders, obstructive sleep apneas, central sleep apneas, or snoring, comprising administering to a human or animal in need thereof an effective amount of at least one compound according to claim 1.

9. A method for treatment of sleep-related respiratory disorders, obstructive sleep apneas, central sleep apneas, or snoring, comprising administering to a human or animal in need thereof an effective amount of a pharmaceutical combination according to claim 6.

10. The compound of claim 1, wherein the compound is a compound of the formula

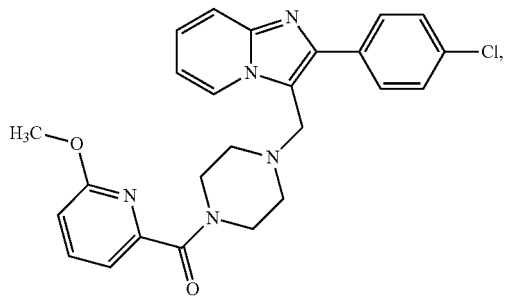

or a salt, a solvate, or a solvate of the salt thereof.

11. The compound of claim 10, wherein the compound is a compound of the formula

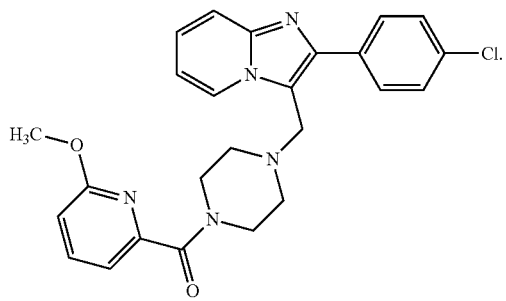 [SMILES: COc1cccc(C(=O)N2CCN(Cc3c(-c4ccc(Cl)cc4)nc4ccccn34)CC2)n1]

12. The compound of claim 1, wherein the compound is a compound of the formula

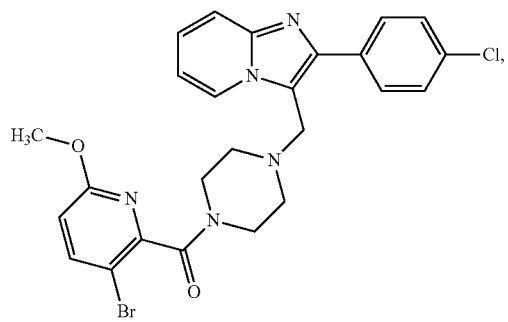 [SMILES: COc1ccc(Br)c(C(=O)N2CCN(Cc3c(-c4ccc(Cl)cc4)nc4ccccn34)CC2)n1]

or a salt, a solvate, or a solvate of the salt thereof.

13. The compound of claim 12, wherein the compound is a compound of the formula

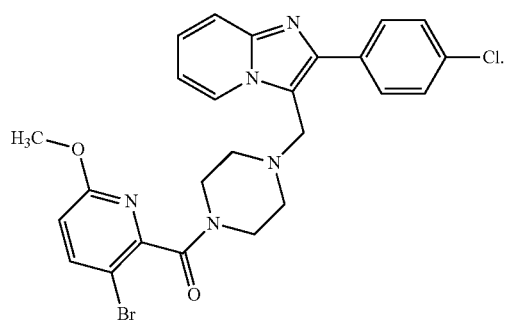

14. The compound of claim 1, wherein the compound is a compound of the formula

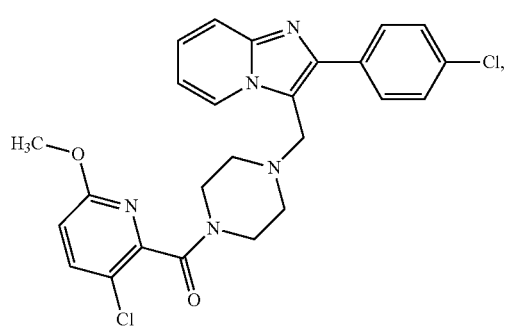

or a salt, a solvate, or a solvate of the salt thereof.

15. The compound of claim 14, wherein the compound is a compound of the formula

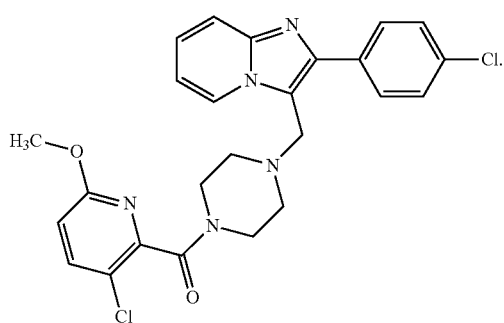 [SMILES: COc1ccc(Cl)c(C(=O)N2CCN(Cc3c(-c4ccc(Cl)cc4)nc4ccccn34)CC2)n1]

16. The compound of claim 1, wherein the compound is a compound of the formula

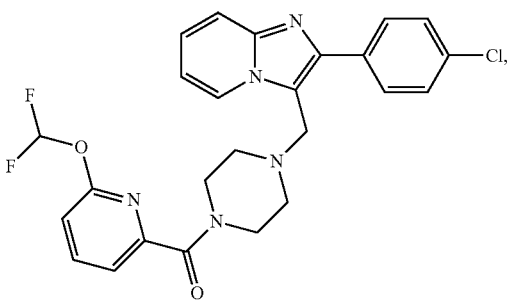 [SMILES: O=C(c1cccc(OC(F)F)n1)N1CCN(Cc2c(-c3ccc(Cl)cc3)nc3ccccn23)CC1]

or a salt, a solvate, or a solvate of the salt thereof.

17. The compound of claim 16, wherein the compound is a compound of the formula

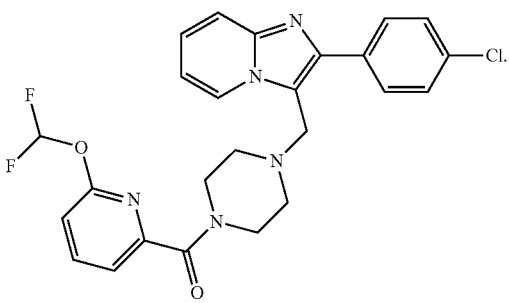 [SMILES: O=C(c1cccc(OC(F)F)n1)N1CCN(Cc2c(-c3ccc(Cl)cc3)nc3ccccn23)CC1]

18. The compound of claim 1, wherein the compound is a compound of the formula

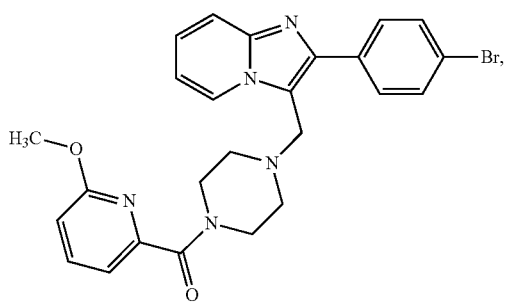 [SMILES: O=C(c1cccc(OC(F)(F)F)n1)N1CCN(Cc2c(-c3ccc(Cl)cc3)nc3ccccn23)CC1]

or a salt, a solvate, or a solvate of the salt thereof.

19. The compound of claim 18, wherein the compound is a compound of the formula

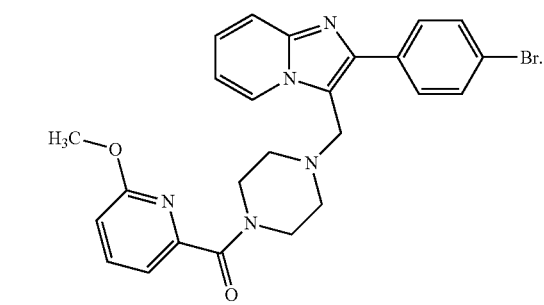 [SMILES: O=C(c1cccc(OC(F)(F)F)n1)N1CCN(Cc2c(-c3ccc(Cl)cc3)nc3ccccn23)CC1]

20. The compound of claim 1, wherein the compound is a compound of the formula

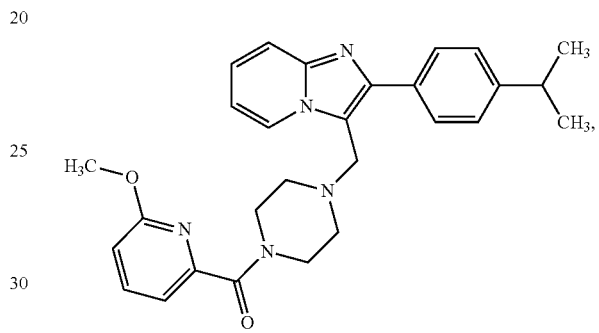

or a salt, a solvate, or a solvate of the salt thereof.

21. The compound of claim 20, wherein the compound is a compound of the formula

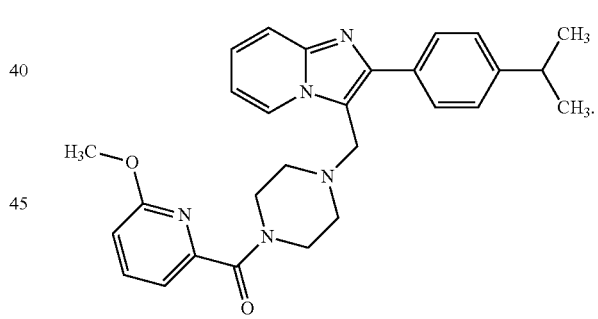

22. The compound of claim 1, wherein the compound is a compound of the formula

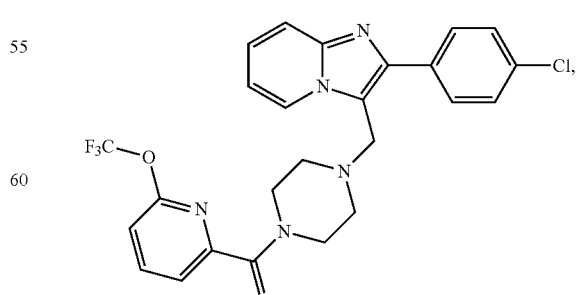

or a salt, a solvate, or a solvate of the salt thereof.

23. The compound of claim 22, wherein the compound is a compound of the formula

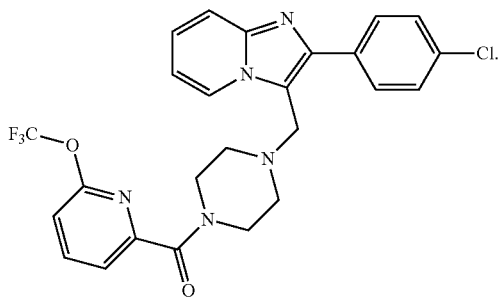

24. The compound of claim 1, wherein the compound is a compound of the formula

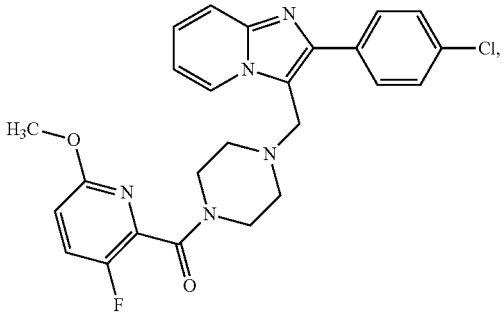

or a salt, a solvate, or a solvate of the salt thereof.

25. The compound of claim 24, wherein the compound is a compound of the formula

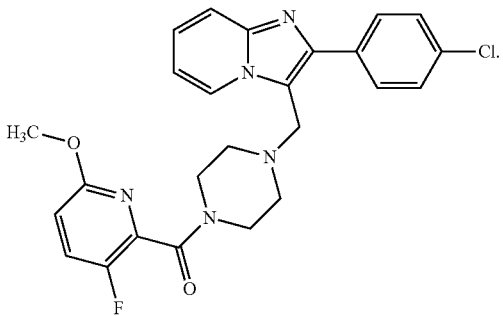 [SMILES: COc1ccc(F)c(C(=O)N2CCN(Cc3c(-c4ccc(Cl)cc4)nc4ccccn34)CC2)n1]

26. The compound of claim 1, wherein the compound is a compound of the formula

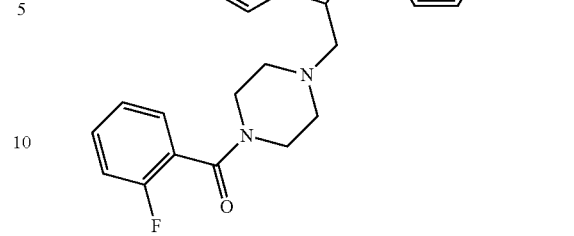

or a salt, a solvate, or a solvate of the salt thereof.

27. The compound of claim 26, wherein the compound is a compound of the formula

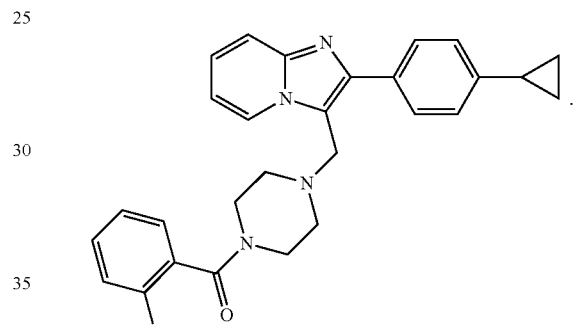

28. The compound of claim 1, wherein the compound is a compound of the formula

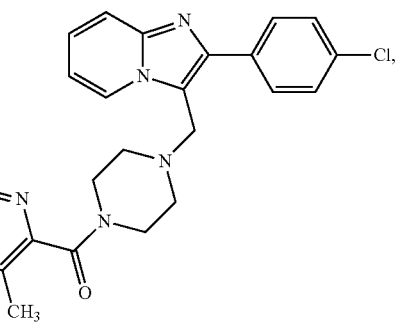

or a salt, a solvate, or a solvate of the salt thereof.

29. The compound of claim 28, wherein the compound is a compound of the formula

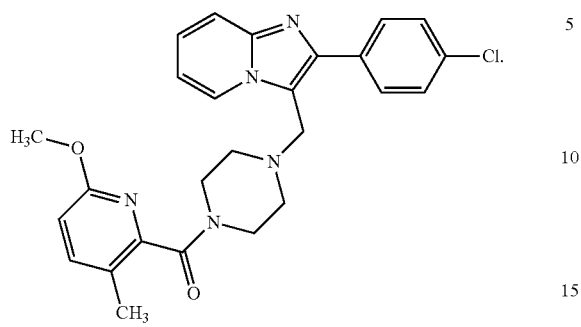

30. A method for treatment of sleep-related respiratory disorders, obstructive sleep apneas, central sleep apneas, or snoring, comprising administering to a human or animal in need thereof an effective amount of a compound, or a salt, a solvate, or a solvate of the salt thereof according to claim 10.

31. A method for treatment of sleep-related respiratory disorders, obstructive sleep apneas, central sleep apneas, or snoring, comprising administering to a human or animal in need thereof an effective amount of a compound according to claim 11.

* * * * *